US009879320B2

(12) United States Patent
Bieche et al.

(10) Patent No.: US 9,879,320 B2
(45) Date of Patent: Jan. 30, 2018

(54) COMBINATION OF BIOMARKERS FOR THE PROGNOSIS OF RESPONSE OR NON-RESPONSE TO AN ANTI-HCV TREATMENT

(76) Inventors: Ivan Bieche, Suresnes (FR); Bénédicte Watelet, Saint Clement de Riviere (FR); Tarik Asselah, Paris (FR); Isabelle Catherine Batxelli, Aigues-vives (FR); Eve Laure Mathieu, Montpellier (FR); Nathalie Jullian, Montrouge (FR); Michel Vidaud, Fontenay Sous Bois (FR); Patrick Marcellin, Paris (FR); Mohammad Afshar, Paris (FR)

( * ) Notice: Subject to any disclaimer, the term of this patent is extended or adjusted under 35 U.S.C. 154(b) by 0 days.

(21) Appl. No.: 13/983,405

(22) PCT Filed: Feb. 9, 2012

(86) PCT No.: PCT/EP2012/052231
§ 371 (c)(1),
(2), (4) Date: Aug. 2, 2013

(87) PCT Pub. No.: WO2012/107528
PCT Pub. Date: Aug. 16, 2012

(65) Prior Publication Data
US 2013/0316332 A1 Nov. 28, 2013

Related U.S. Application Data

(60) Provisional application No. 61/440,980, filed on Feb. 9, 2011, provisional application No. 61/494,470, filed on Jun. 8, 2011.

(30) Foreign Application Priority Data

Feb. 9, 2011 (FR) .................................... 11 51031
Jun. 8, 2011 (FR) .................................... 11 55004

(51) Int. Cl.
| C12Q 1/68 | (2006.01) |
| G01N 33/68 | (2006.01) |
| G01N 33/53 | (2006.01) |
| G01N 33/576 | (2006.01) |
| G06F 19/20 | (2011.01) |
| C12Q 1/70 | (2006.01) |

(52) U.S. Cl.
CPC ......... *C12Q 1/6876* (2013.01); *C12Q 1/6883* (2013.01); *G01N 33/5767* (2013.01); *C12Q 1/707* (2013.01); *C12Q 2600/106* (2013.01); *C12Q 2600/158* (2013.01); *G01N 2800/52* (2013.01)

(58) Field of Classification Search
CPC ................ A61K 2300/00; A61K 45/06; A61K 31/7056; A61K 31/4709
See application file for complete search history.

(56) References Cited

U.S. PATENT DOCUMENTS

| 6,350,601 B1 * | 2/2002 | Aoki .................. C12Q 1/42 424/94.5 |
| 2010/0183555 A1 | 7/2010 | Vidaud et al. |
| 2012/0009148 A1 | 1/2012 | Smith |

FOREIGN PATENT DOCUMENTS

| EP | 1 953 242 | 8/2008 |
| EP | 1 953 242 A1 | 8/2008 |
| WO | WO 2004/108899 A2 | 12/2004 |
| WO | WO2008095907 * | 8/2008 |
| WO | WO 2010/076788 | 7/2010 |
| WO | WO 2010/076788 A2 | 7/2010 |

OTHER PUBLICATIONS

Asselah et al., "Liver gene expression signature to predict response to pegylated interferon plus rivavirin combination therapy i patients with chronic hepatitis C", 2008, Gut, 57:516-524.*
French Search Report dated Dec. 18, 2012, issued in connection with FR 1155004.
French Search Report dated Feb. 7, 2012, issued in connection with FR 1151031.
International Search Report dated May 14, 2012, issued in connection with PCT/EP2012/052231.
Asselah et al, "Liver gene expression signature to predict response to pegylated interferon plus ribavirin combination therapy in patients with chronic hepatitis C", Gut 2008; 57:516-524.
Koutsounaki et al, "Mannose-binding Lectin MBL2 Gene Polymorphisms and Outcome of Hepatitis C Virus-infected Patients", J. Clin Immunol (2008) 28:495-500.
Huang et al, "Serum hs-CRP was correlated with treatment response to pegylated interferon and ribavirin combination therapy in chronic hepatitis C patients", Hepatol Int (2010) 4:621-627.
Kittl et al, "Serum Protein 90K/Mac-2BP Is an Independent Predictor of Disease Severity during Hepatitis C Virus Infection", Clin Chem Lab Med 2000; 38(3):205-208.
Asselah et al, "Liver Gene Expression Signature of Mild Fibrosis in Patients With Chronic Hepatitis C", Gastroenterology 2005; 129:2064-2075.

(Continued)

*Primary Examiner* — Barry A Chestnut
(74) *Attorney, Agent, or Firm* — Saliwanchik, Lloyd & Eisenschenk

(57) ABSTRACT

The application concerns means for predicting whether a subject infected with one or more HCVs has a high probability of responding to an anti-HCV treatment which will comprise the administration of interferon and of ribavirin or whether, in contrast, that subject has a high probability of not responding to that anti-HCV treatment. The means of the invention in particular involve assaying the levels of expression of selected genes, said selected genes being:
at least one gene from among MBL2, LGALS3BP and IL8, and
at least one gene from among G1P2, CCL21 and CXCL10, and
optionally, at least one gene from among AFP, CRP, CXCL11, CXCL6, CXCL9, FGF7, MDK, MMP2, SFN, TGFB2 and VEGFD.

26 Claims, 2 Drawing Sheets

(56) References Cited

OTHER PUBLICATIONS

Bieche et al, "Molecular profiling of early stage liver fibrosis in patients with chronic hepatitis C virus infection", Virology 332 (2005) 130-144.
Chen et al, "Cell-Type Specific Gene Expression Signature in Liver Underlies Response to Interferon Therapy in Chronic Hepatitis C Infection", Gastroenterology 2010; 138:1123-1133.
Abstract Duces et al, No. 684; Journal of Hepatology, Apr. 2010, vol. 52, Supplement 1, p. S267.
Abstract Duces et al, No. T1958; Gastroenterology, May 2010, vol. 138, Issue 5, Supplement 1, p. S-837.
Abstract Duces et al, No. T2000; Gastroenterology, May 2010, vol. 138, Issue 5, Supplement 1, p. S-837.
Poster shown at the Meeting of the American Association of the Study of Liver Diseases (AASLD) on Sep. 2, 2010.
Saito et al, "On-treatment predictions of success in peg-interferon/ribavirin treatment using a novel formula", World J Gastroenterol, Jan. 7, 2010; 16(1):89-97.
International Search Report for PCT/EP2012/052231 dated May 14, 2012.
Written Opinion of the International Searching Authority dated May 14, 2012.
Asselah et al., "Liver Gene Expression Signature to Predict Response to Pegylated Interferon Plus Ribavirin Combination Therapy in Patients with Chronic Hepatitis C", Gut, British Medical Association, vo. 57, No. 4, Apr. 2008, pp. 516-523.
Koutsounaki et al., Mannose-Binding Lectin MBL2 Gene Polymorphisms and Outcome of Hepatitis C Virus-Infected Patients, Journal of Clinical Immunology, vol. 28, No. 5, Jul. 1, 2008, pp. 495-500.
Kittl et al., "Serum Protein 90K/Mac-2BP is an Independent Predictor of Disease Severity During Hepatitis C Virus Infection", Clinical Chemistry and Laboratory Medicine, vol. 38, No. 3, Mar. 1, 2000, pp. 205-208.
Gene List, "Human Genome CGH Microarray 44B G4410B", Agilent Technologies, 2007.

* cited by examiner

SEQUENCE LISTING

<160> NUMBER OF SEQ ID NOS: 36

<210> SEQ ID NO 1
<211> LENGTH: 22
<212> TYPE: DNA
<213> ORGANISM: Homo sapiens

<400> SEQUENCE: 1
ggcacgtatc aaaaagtggc tg                                    22

<210> SEQ ID NO 2
<211> LENGTH: 25
<212> TYPE: DNA
<213> ORGANISM: Homo sapiens

<400> SEQUENCE: 2
atttcaccat tggtcaggaa gaact                                 25

<210> SEQ ID NO 3
<211> LENGTH: 24
<212> TYPE: DNA
<213> ORGANISM: Homo sapiens

<400> SEQUENCE: 3
gaggcagcga actcatcttt gcca                                  24

<210> SEQ ID NO 4
<211> LENGTH: 21
<212> TYPE: DNA
<213> ORGANISM: Homo sapiens

<400> SEQUENCE: 4
ccgccagcat cttcaccgtc a                                     21

<210> SEQ ID NO 5
<211> LENGTH: 19
<212> TYPE: DNA
<213> ORGANISM: Homo sapiens

<400> SEQUENCE: 5
gggcagcgag atgcagcac                                        19

<210> SEQ ID NO 6
<211> LENGTH: 20
<212> TYPE: DNA
<213> ORGANISM: Homo sapiens

<400> SEQUENCE: 6
ccactcagcg cactcgctcc                                       20

<210> SEQ ID NO 7
<211> LENGTH: 20
<212> TYPE: DNA
<213> ORGANISM: Homo sapiens

<400> SEQUENCE: 7
tgacccctcc gaggctcttc                                       20

<210> SEQ ID NO 8
<211> LENGTH: 22
<212> TYPE: DNA
<213> ORGANISM: Homo sapiens

<400> SEQUENCE: 8
atgtcaccat cgttcacgcc tt                                                22

<210> SEQ ID NO 9
<211> LENGTH: 25
<212> TYPE: DNA
<213> ORGANISM: Homo sapiens

<400> SEQUENCE: 9
ctgactctaa gtggcattca aggag                                             25

<210> SEQ ID NO 10
<211> LENGTH: 25
<212> TYPE: DNA
<213> ORGANISM: Homo sapiens

<400> SEQUENCE: 10
ggttgattac taatgctgat gcagg                                             25

<210> SEQ ID NO 11
<211> LENGTH: 25
<212> TYPE: DNA
<213> ORGANISM: Homo sapiens

<400> SEQUENCE: 11
cacagtggta cctgaggatc gataa                                             25

<210> SEQ ID NO 12
<211> LENGTH: 23
<212> TYPE: DNA
<213> ORGANISM: Homo sapiens

<400> SEQUENCE: 12
gccactgtcc tgatttccat gat                                               23

<210> SEQ ID NO 13
<211> LENGTH: 24
<212> TYPE: DNA
<213> ORGANISM: Homo sapiens

<400> SEQUENCE: 13
caccggaagg aaccatctca ctgt                                              24

<210> SEQ ID NO 14
<211> LENGTH: 23
<212> TYPE: DNA
<213> ORGANISM: Homo sapiens

<400> SEQUENCE: 14
tccttggcaa aactgcacct tca                                               23

<210> SEQ ID NO 15
<211> LENGTH: 21
<212> TYPE: DNA
<213> ORGANISM: Homo sapiens

<400> SEQUENCE: 15
agagtgcctg aacaacggat t                                                 21

<210> SEQ ID NO 16
<211> LENGTH: 19
<212> TYPE: DNA
<213> ORGANISM: Homo sapiens

```
<400> SEQUENCE: 16
ccattcgcct tctgctctt                                                    19

<210> SEQ ID NO 17
<211> LENGTH: 24
<212> TYPE: DNA
<213> ORGANISM: Homo sapiens

<400> SEQUENCE: 17
ctccatccca gctatcctgt tctt                                              24

<210> SEQ ID NO 18
<211> LENGTH: 23
<212> TYPE: DNA
<213> ORGANISM: Homo sapiens

<400> SEQUENCE: 18
tctgcacata gctctgcctg aga                                               23

<210> SEQ ID NO 19
<211> LENGTH: 25
<212> TYPE: DNA
<213> ORGANISM: Homo sapiens

<400> SEQUENCE: 19
gtttacgcgt tacgctgaga gtaaa                                             25

<210> SEQ ID NO 20
<211> LENGTH: 21
<212> TYPE: DNA
<213> ORGANISM: Homo sapiens

<400> SEQUENCE: 20
cgttcttcag ggaggctacc a                                                 21

<210> SEQ ID NO 21
<211> LENGTH: 21
<212> TYPE: DNA
<213> ORGANISM: Homo sapiens

<400> SEQUENCE: 21
actgcggttt tctcgaatcc a                                                 21

<210> SEQ ID NO 22
<211> LENGTH: 20
<212> TYPE: DNA
<213> ORGANISM: Homo sapiens

<400> SEQUENCE: 22
ggtatccatc gccatgctcc                                                   20

<210> SEQ ID NO 23
<211> LENGTH: 22
<212> TYPE: DNA
<213> ORGANISM: Homo sapiens

<400> SEQUENCE: 23
cgacaagaag cgcatcattg ac                                                22

<210> SEQ ID NO 24
<211> LENGTH: 22
<212> TYPE: DNA
<213> ORGANISM: Homo sapiens
```

-continued

<400> SEQUENCE: 24
ctgttggcga tctcgtagtg ga                                    22

<210> SEQ ID NO 25
<211> LENGTH: 24
<212> TYPE: DNA
<213> ORGANISM: Homo sapiens

<400> SEQUENCE: 25
gtgtgctaca gttgttcaag gctt                                  24

<210> SEQ ID NO 26
<211> LENGTH: 25
<212> TYPE: DNA
<213> ORGANISM: Homo sapiens

<400> SEQUENCE: 26
ctcaatatct gccactttca ctgct                                 25

<210> SEQ ID NO 27
<211> LENGTH: 24
<212> TYPE: DNA
<213> ORGANISM: Homo sapiens

<400> SEQUENCE: 27
acccgaactt tccaagccat aact                                  24

<210> SEQ ID NO 28
<211> LENGTH: 26
<212> TYPE: DNA
<213> ORGANISM: Homo sapiens

<400> SEQUENCE: 28
ccacatccag gactagtttc tggatt                                26

<210> SEQ ID NO 29
<211> LENGTH: 24
<212> TYPE: DNA
<213> ORGANISM: Homo sapiens

<400> SEQUENCE: 29
cctcgtacat ttccaaacag ctct                                  24

<210> SEQ ID NO 30
<211> LENGTH: 24
<212> TYPE: DNA
<213> ORGANISM: Homo sapiens

<400> SEQUENCE: 30
tggcaagcac ttacaacctg tatg                                  24

<210> SEQ ID NO 31
<211> LENGTH: 23
<212> TYPE: DNA
<213> ORGANISM: Homo sapiens

<400> SEQUENCE: 31
gacgtgacca tggagaagct gtt                                   23

<210> SEQ ID NO 32
<211> LENGTH: 24
<212> TYPE: DNA

```
<213> ORGANISM: Homo sapiens

<400> SEQUENCE: 32
aagccttcct cgacatgtct gtct                                          24

<210> SEQ ID NO 33
<211> LENGTH: 24
<212> TYPE: DNA
<213> ORGANISM: Homo sapiens

<400> SEQUENCE: 33
atccacctac aatccttgaa agac                                          24

<210> SEQ ID NO 34
<211> LENGTH: 26
<212> TYPE: DNA
<213> ORGANISM: Homo sapiens

<400> SEQUENCE: 34
tccattcttc agtgtagcaa tgattt                                        26

<210> SEQ ID NO 35
<211> LENGTH: 20
<212> TYPE: DNA
<213> ORGANISM: Homo sapiens

<400> SEQUENCE: 35
ggcgacctgg aagtccaact                                               20

<210> SEQ ID NO 36
<211> LENGTH: 20
<212> TYPE: DNA
<213> ORGANISM: Homo sapiens

<400> SEQUENCE: 36
ccatcagcac cacagccttc                                               20
```

COMBINATION OF BIOMARKERS FOR THE PROGNOSIS OF RESPONSE OR NON-RESPONSE TO AN ANTI-HCV TREATMENT

This application is the U.S. national phase of International Application No. PCT/EP2012/052231 filed 9 Feb. 2012 which designated the U.S. and claims priority to FR 1151031 filed 9 Feb. 2011, FR 1155004 filed 8 Jun. 2011, U.S. Provisional Application No. 61/440,980 filed 9 Feb. 2011, and U.S. Provisional Application No. 61/494,470 filed 8 Jun. 2011, the entire contents of each of which are hereby incorporated by reference.

FIELD OF THE INVENTION

The application relates to means for establishing a prediction of a high probability of a response or non-response to an anti-hepatitis C virus (HCV) treatment. Advantageously, the means of the invention can be used to establish this prediction before the anti-HCV treatment has even commenced.

BACKGROUND TO THE INVENTION

In the vast majority of cases, an infection with the hepatitis C virus (HCV) leads to chronic hepatitis C. Chronic hepatitis C can develop into cirrhosis of the liver with portal hypertension complications, and can also develop into hepatocellular carcinoma.

One of the aims of treatment against an infection by HCV, more particularly against chronic hepatitis C, is to arrive at the stage where the attacks on the liver tissue induced by the viral infection regress or are even eliminated, or at least that they do not progress. In particular, this means that the risk which arises of complications and hepatocellular carcinoma can be reduced or eliminated.

Currently available treatments for achieving this aim are treatments which are aimed at eradicating the virus. In the first place, these treatments have to induce a significant reduction in the viral HCV load, so as to be able to obtain an undetectable level at the end of treatment.

Current anti-HCV treatments comprise the administration of a combination of pegylated interferon and ribavirin. These treatments are of long duration: they are generally administered over a period of at least 24 weeks and may last up to 48 weeks or even longer.

However, anti-HCV treatments cause major side effects for the patient.

Regarding interferon, the side effects are frequent and numerous. The most frequent side effect is that of influenza-like syndrome (fever, arthralgia, headaches, chills). Other possible side effects are: asthenia, weight loss, moderate hair loss, sleep problems, mood problems and irritability, which may have repercussions on daily life, difficulties with concentrating and skin dryness. Certain rare side effects, such as psychiatric problems, may be serious and have to be anticipated. Depression may occur in approximately 10% of cases. This has to be identified and treated, as it can have grave consequences (attempted suicide). Dysthyroidism may occur. Furthermore, treatment with interferon is counter-indicated during pregnancy.

Regarding ribavirin, the principal side effect is haemolytic anaemia. Anaemia may lead to treatment being stopped in approximately 5% of cases. Decompensation due to an underlying cardiopathy or coronaropathy linked to anaemia may arise.

Neutropenia is observed in approximately 20% of patients receiving a combination of pegylated interferon and ribavirin, and represents the major grounds for reducing the pegylated interferon dose.

The cost of these treatments is also very high.

In order to be able to predict, before having even commenced administration of the anti-HCV treatment, whether a given patient will or will not respond to treatment is thus of major clinical and economic importance.

Research into predictive means of this type has led to various clinical, biological and viral factors being analysed.

Certain clinical factors of the patient, such as age, weight, ethnic origin and hepatic fibrosis score are known to influence the efficacy of anti-HCV treatment.

As an example, the number of patients responding to anti-HCV treatment is lower among patients with a hepatic fibrosis score of F3 or F4 compared with those for whom the hepatic fibrosis score is F1 or F2 (scores using the Metavir F score system).

Of themselves, however, these clinical factors cannot be used to reliably predict, prior to starting a treatment, whether a given patient will or will not respond to an anti-HCV treatment.

Thus, of themselves, these factors are not good pre-therapeutic prognostic indicators.

In order to attempt to predict, before administering any treatment, whether a patient will or will not respond to an anti-HCV treatment, in fact it is viral factors which are currently being used.

It has in fact been shown that patients who are infected with an HCV of genotype 2 or 3 respond better to anti-HCV treatment than those who are infected with HCV of genotype 5 or 6, who in turn respond better to anti-HCV treatment than those who are infected with an HCV of genotype 1 or 4.

However, the distribution of the various genotypes is not homogeneous with respect to geographical locations, and thus simply discerning the viral genotype does not provide a predictive solution which can be applied to all patients.

What is more, there are differences between the viral sub-types.

In fact, knowledge of the nature of the viral genotype can essentially be used to adjust the posology and/or duration of treatment, but cannot per se be used to establish a reliable prediction before starting treatment.

Various combinations of biological and/or clinical and/or viral factors have also been tested in order to attempt to predict, before administering any treatment, whether a patient will or will not respond to an anti-HCV treatment. However, the combinations which have been tested up to now have not achieved satisfactorily predictive performances.

As an example, Hidetsugu Saito et al. 2010 succeeded in identifying combinations of biological, clinical and viral factors which gave reliable predictive performances when they were applied during treatment, but they were not at all able to identify a combination which was sufficiently reliable when applied before starting anti-HCV treatment.

Chen et al. 2005 and Chen et al. 2010 proposed a transcriptome signature for predicting, before any anti-HCV treatment was administered, whether a patient would be a responder or non-responder to this treatment. That signature combined the levels of expression of eighteen genes (G1P2, OAS2, G1P3, OAS3, RPLP2, CEB1, IFIT1, VIPERIN, RPS28, PI3KAP1, MX1, DUSP1, ATF5, LAP3, USP18, LGP1, ETEF1 and STXBP5).

Further, at least two of those genes code for proteins which are exclusively membrane proteins (G1P3 and VIPERIN); thus, the product of the expression thereof cannot be detected in the bloodstream.

Asselah et al. 2008 analysed the level of expression of fifty-eight genes before applying anti-HCV treatment to forty patients with chronic hepatitis C, fourteen of whom were non-responders to anti-HCV treatment. They thus identified two signatures which might be able to predict, before administering any anti-HCV treatment, whether a patient would be a non-responder to that treatment.

The first signature was based on the levels of expression of two genes, namely IF127 and CXCL9, which were analysed using the KNN method (k-nearest neighbour method).

The second signature was based on the levels of expression of three genes, namely IF127, CXCL9 and IFI-6-16, which were analysed using the WV method (weighted voting method).

For each of these two signatures, Asselah et al. 2008 indicated that the fact of adding supplemental genes did not allow the accuracy of the classification to be improved.

Thus, there is still a need for means which could be used to predict, even before commencing to administer the anti-HCV treatment, whether the patient has a high probability of responding or, in contrast, a high probability of not responding to treatment.

SUMMARY OF THE INVENTION

The application relates to means which can be used to establish a high probability prediction of response or non-response to an anti-HCV treatment.

Advantageously, the means of the invention can be used to make this prediction before the anti-HCV treatment has even begun.

The inventors have identified genes the levels of expression of which are predictive biomarkers of a response or non-response to anti-HCV treatment. More particularly, the inventors propose establishing the expression profile of these genes, and of using this profile as a predictive signature of response or non-response to anti-HCV treatment.

The application provides means which are especially suited to this purpose. In particular, the means of the invention implement the measurement or assay of the levels of expression of the selected genes, said selected genes being selected from the following list of genes: MBL2, LGALS3BP and IL8, G1P2, CXCL10, CCL21, AFP, CRP, CXCL11, CXCL6, CXCL9, FGF7, MDK, MMP2, SFN, TGFB2 and VEGFD.

More particularly, said selected genes comprise:
at least one gene from among MBL2, LGALS3BP and IL8, and
at least one gene from among G1P2, CCL21 and CXCL10, and
optionally, at least one gene from among AFP, CRP, CXCL11, CXCL6, CXCL9, FGF7, MDK, MMP2, SFN, TGFB2 and VEGFD.

Optionally, the means of the invention may further employ the measurement or assay of one or more clinical factors and/or one or more other virological factors and/or one or more other biological factors.

In particular, the means of the invention comprise:
methods which comprise the measurement or assay of the levels of expression of selected genes;
products or reagents which are specially adapted to the measurement or assay of these levels of gene expression;
manufactured articles, compositions, pharmaceutical compositions, kits, tubes or solid supports comprising such products or reagents, as well as
computer systems (in particular a computer program product and computer device) which are specially adapted to implementing the means of the invention.

DETAILED DESCRIPTION OF THE INVENTION

Figure 1A:
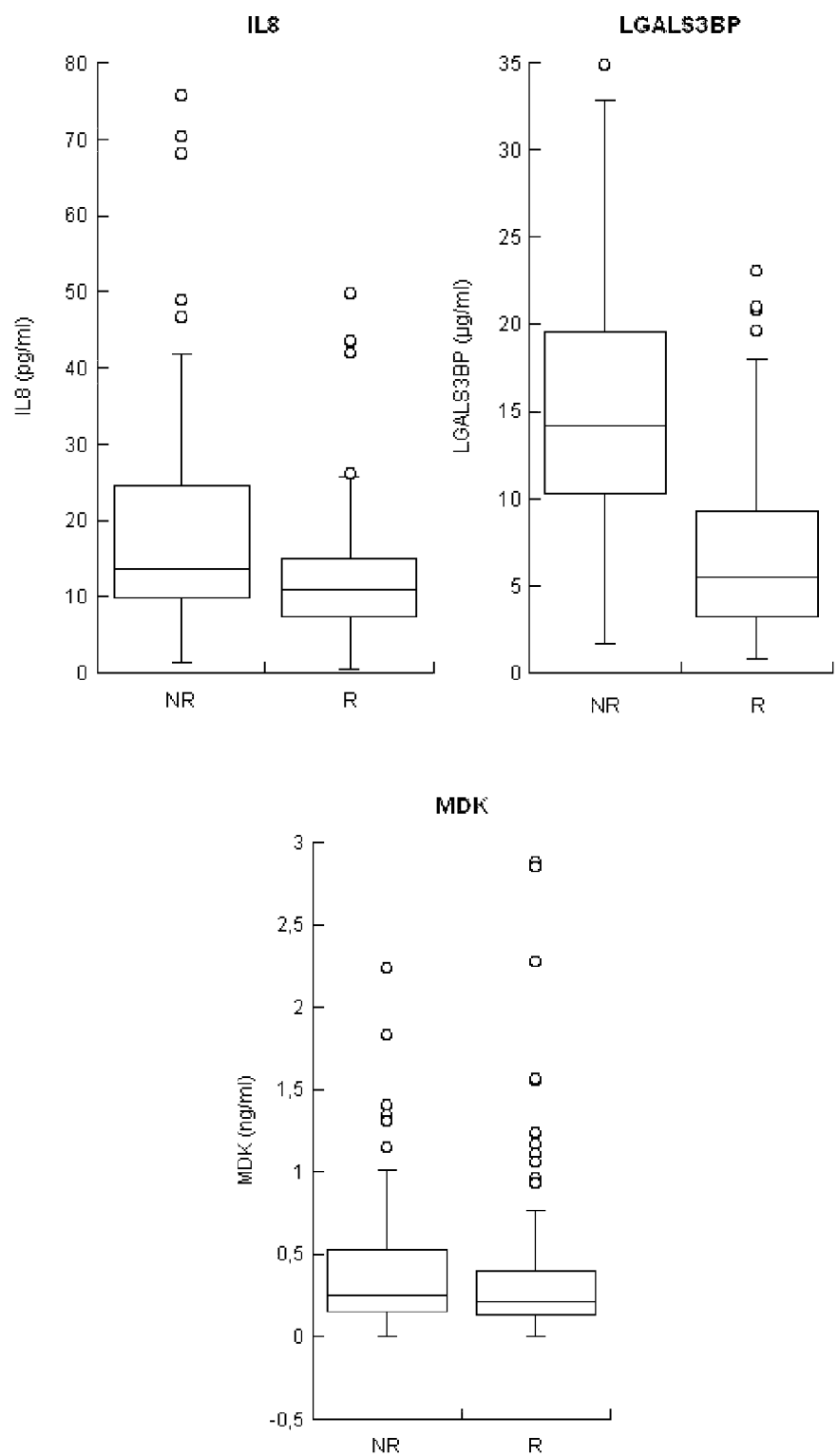
FIGS. 1A and 1B: Distribution of the seric concentrations of the proteins IL8, LGALS3BP, MDK CXCL10 and CCL21 in relation to the patient's status of responder (R) or non-responder (NR).

The stage of liver tissue damage, more particularly the nature and extent of hepatic tissue lesions, is evaluated by a hepatic fibrosis score, in particular using the Metavir F score system, which comprises five stages from F0 to F4.

When the hepatic fibrosis score is at most F1, the clinician may optionally decide not to administer anti-HCV treatment, but when the score is at least F2, the current recommendation is to administer an anti-HCV treatment irrespective of the level of necrotico-inflammatory activity.

Since anti-HCV treatments are of very long duration (generally 6 to 12 months, or even longer), they induce particularly serious side effects and are very expensive; the present application proposes means for assisting in the decision as to whether or not to administer anti-HCV treatment.

The means of the invention can be used to provide a prediction of a high probability of a response or non-response to anti-HCV treatment. Advantageously, the means of the invention can be used to establish this prediction before this treatment has even begun.

The means of the invention comprise assaying or measuring the levels of expression of selected genes. They concern subjects who are infected with one or more hepatitis viruses, at least one of which is an HCV, and more particularly those of these subjects who have a hepatic fibrosis score of at least F1, more particularly at least F2, using the Metavir F score system.

In the application, unless otherwise specified, or unless the context indicates otherwise, all of the terms used have their usual sense in the domain(s) concerned. The expression "anti-HCV treatment", "hepatitis C treatment" or an equivalent expression or the shortened term "treatment" signifies a treatment for therapeutic purposes which is intended to induce a reduction in the HCV load of the patient such that at the end of the treatment, an undetectable level of HCV load, or even eradication of the HCV or HCVs, is obtained. Clinically, the desired therapeutic intention is to stop or cause to regress or even to eliminate liver tissue lesions, i.e. at the very least to prevent the hepatic fibrosis score from increasing, or even for that score to reduce, preferably to a score of at most F1.

The anti-HCV treatment comprises at least one administration of interferon, more particularly alpha interferon, in particularly alpha-2a interferon or alpha-2b interferon, or a prodrug of interferon.

This interferon is generally a version produced by genetic engineering of natural human cytokine. However, this interferon may be an interferon which derives from Chinese hamster ovary cells (CHO cells), such as omega interferon (for example, omega interferon available from Intarcia Therapeutics, Hayward, Calif., USA).

This interferon may in particular be associated with other chemical compounds, groups or molecules, in particular polyethylene glycol (for example, PEG-INTRON® supplied by Schering Plough Corporation, Kenilworth, N.J., USA, or PEGASYS® supplied by F. Hoffmann-La Roche Ltd.; Basel, Switzerland).

The pegylated form of interferon has a longer lifetime in the human body, which means that the frequency of administration can be limited to a single administration per week (in the event, a single injection per week) instead of three administrations per week for the non-pegylated form.

The pegylated form of interferon is thus currently the preferred form of interferon.

A pegylated interferon may, for example, be administered:
in a dose of approximately 1.5 g/kg/week for pegylated alpha-2b interferon (such as PEG-INTRON®),
at a concentration of 180 g/kg/week for pegylated alpha-2a interferon (such as PEGASYS®).

In addition to interferon, an anti-HCV treatment generally includes administering at least one other antiviral agent.

In addition to interferon, current anti-HCV treatment generally includes administering ribavirin.

Ribavirin is a nucleoside analogue of guanosine.

In the context of the application, and in accordance with a particular embodiment of the invention, the anti-HCV treatment comprises administering interferon and administering:
ribavirin (for example, the ribavirin REBETOL® supplied by Plough Corporation, Kenilworth, N.J., USA, or the ribavirin COPEGUS® supplied by Roche Corporation; F. Hoffmann-La Roche Ltd.; Basel, Switzerland), or
an analogue of ribavirin, or
a prodrug of ribavirin or one of its analogues.

Ribavirin prodrugs in particular include taribavirin (for example, the taribavirin which is available from Valeant, Aliso Viejo, Calif., USA).

The ribavirin is preferably administered daily.

The ribavirin may, for example, be administered in an amount of 800 to 1200 mg/kg/day.

An anti-HCV treatment may, for example, comprise the administration of:
pegylated alpha-2b interferon (such as PEG-INTRON®) in a dose of approximately 1.5 g/kg/week, and ribavirin in a dose of 800 to 1 200 mg/kg/day (if the hepatopathy involves an HCV of genotype 2 or 3, a dose of approximately 800 mg/kg/day is generally advised), or
pegylated alpha-2a interferon (such as PEGASYS®) in a concentration of 180 g/kg/week and ribavirin in an amount of 1000 to 1200 mg/kg/day.

In addition to interferon, or interferon and ribavirin, the anti-HCV treatment may also comprise administration of at least one other generic or specific HCV antiviral agent, such as:
at least one HCV protease inhibitor, such as an NS3 protease inhibitor, and/or
at least one HCV polymerase inhibitor, such as a NS5B polymerase inhibitor, more particularly at least one HCV protease inhibitor, such as an NS3 protease inhibitor.

Said NS3 protease inhibitor may, for example be telaprevir (VX-950; Vertex, Cambridge, Mass., USA) or boceprevir (SCH-503034; Schering-Plough, Kenilworth, N.J., USA). The combination of interferon (or an analogue or a prodrug of interferon), ribavirin (or an analogue or a prodrug of ribavirin) and an HCV protease inhibitor such as telaprevir or boceprevir (or an analogue or a prodrug of this protease inhibitor) is a tritherapy which is in particular envisaged for the treatment of patients who are infected with at least one HCV of genotype 1 or 4.

Said NS5B polymerase inhibitor may, for example, be a nucleoside analogue such as R1479, or its prodrug R1626 (Roche, Basel, Switzerland), or the nucleoside analogue PSI-6130, or its prodrug R7128 (Pharmasset, Princeton, N.J., U.S.A.; Roche, Basel, Switzerland).

In addition to the antiviral agent or agents, the anti-HCV treatment may also comprise administering at least one other product with no direct antiviral activity, such as a drug adjuvant, for example a hormone which stimulates the production of erythrocytes and/or leukocytes, such as erythropoietin (EPO).

The anti-HCV treatment period is generally at least approximately 24 weeks, very generally approximately 24 to 48 weeks, but sometimes longer. As an example, it may be:
approximately 24 weeks for hepatopathy due to HCV of genotype 2 or 3,
approximately 48 weeks for hepatopathy due to HCV of genotype 1, 4 or 5, or for a patient who is not responsive to treatment after 24 weeks.

The expressions "responder" or "non-responder" should be understood to have the meanings which are usually attributed to them in the medical field. The expressions "responder" or "non-responder" should be understood to mean "responder to anti-HCV treatment" or "non-responder to anti-HCV treatment", respectively.

A subject is considered to be:
a subject who is a responder to treatment (patient classified as R) when the viral load of HCV has become undetectable in the blood of the patient at the end of an anti-HCV treatment associating the administration of interferon and the administration of ribavirin (or a prodrug or an analogue of these active principles) and that this viral load remains undetectable 6 months after that treatment is stopped;
a subject who is a non-responder to treatment (patient classified as NR) when the viral load of HCV remains undetectable in the blood of the patient at the end of this anti-HCV treatment;
a responder-relapser (patient classified as RR) when the viral load of HCV becomes undetectable in the blood of the patient at the end of this anti-HCV treatment, but it becomes detectable again 6 months after stopping this anti-HCV treatment.

This anti-HCV treatment is generally administered:
over approximately 24 weeks for hepatopathy due to HCV of genotype 2 or 3,
over approximately 48 weeks for hepatopathy due to HCV of genotype 1, 4, 5 or 6.

The treatment may be one of the treatments mentioned above, in particular such as a treatment comprising or consisting of administering ribavirin (or a prodrug or an analogue of this active principle) and alpha-2a interferon or alpha-2b interferon, more particularly pegylated interferon (more particularly, pegylated alpha-2a interferon or pegylated alpha-2b interferon), or a prodrug or an analogue of this active principle.

The interferon is usually administered at a frequency of once a week, while the ribavirin is usually administered at a frequency of twice a day.

Particular examples of treatment include the following: treatment by administration:
- of pegylated alpha-2b interferon (PEG-INTRON®; Schering Plough Corporation; Kenilworth, N.J.; U.S.A.) in a dose of 1.5 g/kg/week, and
- of ribavirin (REBETOL®; Schering Plough Corporation; Kenilworth, N.J.; U.S.A.), as a function of the patient's weight and the HCV genotype(s), in a dose of:
  - 800 to 1200 mg/kg/day for those patients who have been infected with at least one genotype 1 and/or 4 and/or 5 and/or 6 of HCV, or in a dose of
  - 800 mg/kg/day for those patients who have been infected with at least one genotype 2 and/or 3 of HCV, or treatment by administration:
- of pegylated alpha-2a interferon (PEGASYS®; Roche Corporation; F. Hoffmann-La Roche Ltd.; Basel, Switzerland) in a dose of 180 g/kg/week, and
- of ribavirin (COPEGUS®; Roche Corporation; F. Hoffmann-La Roche Ltd.; Basel, Switzerland) in a dose of 1000 to 1200 mg/kg/day.

One or other of these two examples of treatment can be administered for 24 weeks for those of the subjects who have been infected with at least one genotype 2 and/or 3 of HCV, and for 48 weeks for those subjects who have been infected with at least one genotype 1 and/or 4 and/or 5 and/or 6 of HCV.

The viral load of HCV can be considered to be undetectable in the blood of a subject when the measurement of HCV RNA in the serum of a subject has given a value of less than 12 International Units (IU) per mL of serum, as assayed in a test for the quantification of HCV RNA, for example as assayed in a quantification test carried out with the aid of a VERSANT® HCV-RNA 3.0 (bDNA) ASSAY kit from Siemens Healthcare Diagnostics (quantification limit=615–7 690 000 IU/mL), following the recommendations of the manufacturer of this kit.

The inventors have identified genes the level of expression of which constitute biomarkers which, when taken in combination, are pertinent to determining the status of "responder" (R) or "non-responder" (NR) of a subject.

The inventors have also observed that, depending on these expression level combinations, the population of responder-relapser (RR) subjects is very strongly segregated from that of the responders (R): RR subjects are mainly classified as R (see Examples below).

The genes identified thereby are the following seventeen genes: MBL2, LGALS3BP and IL8, G1P2, CXCL10, CCL21, AFP, CRP, CXCL11, CXCL6, CXCL9, FGF7, MDK, MMP2, SFN, TGFB2 and VEGFD.

Particularly advantageously, it has been observed that these seventeen genes are all genes coding for non-membrane proteins, i.e. genes which code for a protein which has an intracellular and/or extracellular location and which thus can be detected in a biological fluid of the subject such as the blood, serum or plasma.

The inventors have also identified that the most pertinent combinations comprise:
- at least one gene from among MBL2, LGALS3BP and IL8, and
- at least one gene from among G1P2, CCL21 and CXCL10, and
- optionally, at least one gene from among AFP, CRP, CXCL11, CXCL6, CXCL9, FGF7, MDK, MMP2, SFN, TGFB2 and VEGFD.

Each of these genes is individually known to the skilled person and should be understood to have the meaning given to it in this field. An indicative reminder of their respective identities is presented in Table 1 below:

TABLE 1

Identity of genes

| Symbol | Name (in French) of coded protein | Name (in English) of coded protein | Alias | NM accession number |
| --- | --- | --- | --- | --- |
| MBL2 | lectine 2 se liant au mannose | mannose-binding lectin 2 | | NM_000242 |
| G1P2 | protéine inductible par l'interféron alpha (clone IFI-15K) | interferon alpha inducible protein (clone IFI-15K) | ISG15, IFI15 | NM_005101.3 |
| MDK | midkine | midkine | NEGF2 | NM_001012334 |
| LGALS3BP | protéine se liant à LGALS3 (lectine, se liant à la galactosidase, soluble, 3) | lectin, galactosidase-binding, soluble, 3 binding protein | 90K, MAB-2-BP | NM_005567.3 |
| CXCL10 | ligand 10 à chémokine (motif CXC) | chemokine (CXC motif) ligand 10 | C7, IFI10, INP10, IP-10, SCYB10, crg-2, gIP-10, mob-1 | NM_001565 |
| FGF7 | facteur de croissance de fibroblastes 7 | fibroblast growth factor 7 | HBGF7, KGF | NM_002009 |
| IL8 | interleukine 8 | interleukin 8 | CXCL8, GCP-1, GCP1, LECT, LUCT, LYNAP, MDNCF, MONAP, NAF, NAP-1, NAP1 | NM_000584 |
| TGFB2 | facteur de croissance transformant beta 2 | transforming growth factor beta 2 | | NM_001135599.1 |
| CCL21 | ligand 21 à chémokine (motif C-C) | chemokine (C-C motif) ligand 21 | ECL, SLC, SCYA21 | NM_002989 |
| CXCL6 | ligand 6 à chémokine (motif CXC) | chemokine (CXC motif) ligand 6 | CKA-3, GCP-2, GCP2, SCYB6 | NM_002993 |
| MMP2 | métallopeptidase 2 de matrice | matrix metallopeptidase2 | CLG4, MONA TBE1 | NM_004530 |
| SFN | stratifine | stratifin | YWHAS | NM_006142.3 |
| CXCL11 | ligand 11 à chémokine (motif CXC) | chemokine (CXC motif) ligand 11 | IP9, SCYB11 | NM_005409.3 |
| AFP | alphafétoprotéine | alphafetoprotein | FETA, HPFAP | NM_001134 |
| VEGFD | factor de croissance induit par C-Fos | C-Fos induced growth factor | FIGF | NM_004469.2 |
| CRP | protéine C-réactive apparentée à la pentaxine | C-reactive protein pentaxin-related | PTX1 | NM_000567.2 |
| CXCL9 | ligand 9 à chémokine (motif CXC) | chemokine (CXC motif) ligand 9 | CMK, Myg, SCYB9 | NM_002416.1 |

TABLE 1-continued

Identity of genes

| Symbol | Name (in French) of coded protein | Name (in English) of coded protein | Alias | NM accession number |
|---|---|---|---|---|
| RPLP0 | phosphoprotéine ribosomale acide P0 human | human acidic ribosomal phosphoprotein P0 | 36B4 | NM_001002 |
| TBP | protéine se liant à la boîte TATA | TATA box binding protein | | NM_003194 |

None of these genes is a gene of the hepatitis virus. They are mammalian genes, more particularly human genes.

Each of these genes codes for a non-membrane protein, i.e. a protein which is not anchored in a cell membrane. The in vivo localization of these proteins is thus intracellular and/or extracellular. These proteins are present in a biological fluid of the subject, such as in the blood, serum, plasma or urine, for example, in particular in the blood or the serum or the plasma.

In addition to the levels of expression of genes selected from the list of the seventeen genes of the invention (MBL2, LGALS3BP and IL8, G1P2, CXCL10, CCL21, AFP, CRP, CXCL11, CXCL6, CXCL9, FGF7, MDK, MMP2, SFN, TGFB2 and VEGFD), the means of the invention may further comprise the measurement of other factors, in particular one or more clinical factors and/or one or more virological factors and/or one or more biological factors other than the level of expression of the genes selected from said list of seventeen genes.

More particularly, in addition to the levels of expression of the genes selected from said list of seventeen genes of the invention, the means of the invention may optionally comprise (see Examples 2c) and 3b) below):

measuring the level of expression of mammalian genes (more particularly human genes) other than those from said list of seventeen genes, for example to measure the level of transcription of genes which are listed below as "other biological factors", such as the gene coding for gamma glutamyl transpeptidase (GGT) and/or the gene coding for alkaline phosphatase (ALP), and/or measuring intracorporal metabolites (for example, cholesterol), and/or measuring elements occurring in the blood (for example platelets), and/or measuring the quantity of iron which is circulating.

However, these measurements are optional.

In accordance with the application, the number of mammalian genes (more particularly human genes) the level of expression of which is measured and which are not genes selected from said list of seventeen genes of the invention (for example GGT and/or ALP), is preferably a maximum of 18, more particularly 14 or fewer, more particularly 11 or fewer, more particularly 6 or fewer, more particularly 4 or 3 or 2 or 1 or 0, more particularly 3 or 2 or 1 or 0, in particular 2 or 1 or 0.

It follows that counting these "other" mammalian genes (more particularly these "other" human genes) the level of expression of which may optionally be assayed, as well as the maximum number of seventeen genes which may be the genes selected in accordance with the invention, the total number of genes the level of expression of which is measured in a method in accordance with the application is preferably 2 to 35 genes, more particularly 2 to 31, more particularly 2 to 28, more particularly 2 to 23, more particularly 2 to 21, more particularly 2 to 20, more particularly 2 to 19, more particularly 2 to 18, in particular 2 to 17, more particularly 2 to 16, more particularly 2 to 15, more particularly 2 to 14, more particularly 2 to 13, more particularly 2 to 12, more particularly 2 to 11, more particularly 2 to 10, more particularly 2 to 9, more particularly 2 to 8, more particularly 2 to 7, more particularly 2 to 6 (for example 2, 3, 4, 5 or 6), more particularly 2 to 5 (for example 2, 3, 4 or 5).

Further, as will be presented in more detail below, and as illustrated in the Examples, the number of genes selected from the list of seventeen genes of the invention (MBL2, LGALS3BP and IL8, G1P2, CXCL10, CCL21, AFP, CRP, CXCL11, CXCL6, CXCL9, FGF7, MDK, MMP2, SFN, TGFB2 and VEGFD) may advantageously be 2, 3, 4 or 5.

In one embodiment, the total number of genes the level of expression of which is measured, is:
2, 3, 4 or 5 genes selected from said list of seventeen genes of the invention, and
0, 1, 2, 3 or 4 "other" mammalian genes, more particularly 0, 1, 2 or 3 "other" mammalian genes, more particularly 0, 1 or 2 "other" mammalian genes.

In one embodiment, the total number of mammalian genes the level of expression of which is measured in a method in accordance with the application is thus 2 to 9, more particularly 2 to 8, more particularly 2 to 7, more particularly 2 to 6, more particularly 2 to 5, more particularly 2 to 4.

The means of the invention may optionally comprise measuring the expression product (RNA or protein) of one or more non-human genes, more particularly one or more viral genes, more particularly one or more genes of the hepatitis virus, more particularly one or more genes of HCV.

The means of the invention may optionally comprise determining the genotype or genotypes of the HCV or HCVs with which the subject is infected.

The means of the invention may optionally comprise determining one or more clinical factors of said subject, such as the viral load before treatment (VLbeforeTTT in the examples below).

One feature of the means of the invention is that they include the fact of measuring (or assaying) the level to which the selected genes are expressed in the organism of said subject.

The expression "level of expression of a gene" or equivalent expression as used here designates both the level to which this gene is transcribed into RNA, more particularly into mRNA, and also the level to which a protein encoded by that gene is expressed.

The term "measure" or "assay" or equivalent term is to be construed as being in accordance with its general use in the field, and refers to quantification.

The level of transcription (RNA) of each of said genes or the level of translation (protein) of each of said genes or the level of transcription for certain of said selected genes and the level of translation for the others of these selected genes can be measured. In accordance with one embodiment of the invention, either the level of transcription or the level of translation of each of said selected genes is measured.

The fact of measuring (or assaying) the level of transcription of a gene includes the fact of quantifying the RNAs transcribed from that gene, more particularly of determining the concentration of RNA transcribed by that gene (for example the quantity of those RNAs with respect to the total quantity of RNA initially present in the sample, such as a value for Ct normalized by the $2^{-\Delta Ct}$ method; see below).

The fact of measuring (or assaying) the level of translation of a gene includes the fact of quantifying proteins encoded by that gene, more particularly of determining the concentration of proteins encoded by this gene, (for example the quantity of that protein per volume of biological fluid).

Certain proteins encoded by a mammalian gene, in particular a human gene, may occasionally be subjected to post-translation modifications such as, for example, cleavage into polypeptides and/or peptides. If appropriate, the fact of measuring (or assaying) the level of translation of a gene may then comprise the fact of quantifying or determining the concentration, not of the protein or proteins themselves, but of one or more post-translational forms of this or these proteins, such as, for example, polypeptides and/or peptides which are specific fragments of this or these proteins.

In order to measure or assay the level of expression of a gene, it is thus possible to quantify:
the RNA transcripts of that gene, or
proteins expressed by this gene or post-translational forms of such proteins, such as polypeptides or peptides which are specific fragments of these proteins, for example.

The application pertains to the subject matter defined in the claims as filed, the subject matter described below and the subject matter illustrated in the "Examples" section.

In particular, the application concerns means for predicting whether a subject infected with one or more HCVs has a high probability of responding to an anti-HCV treatment which will comprise administering interferon and ribavirin or whether, in contrast, that subject has a high probability of not responding to said anti-HCV treatment.

In particular, the means of the invention comprise:
methods which include measuring or assaying the levels of expression of selected genes (level of transcription or translation);
products or reagents which are specifically adapted to measuring or assaying these levels of expression of the genes;
manufactured articles, compositions, pharmaceutical compositions, kits, tubes or solid supports comprising such products or reagents; as well as
computer systems (in particular, a computer program product and computer device) which are specially adapted to implementing the means of the invention.

The means of the invention, more particularly the method of the invention, are deployed before treating the HCV infection, and advantageously may be deployed before the anti-HCV treatment has been commenced, more particularly before any anti-HCV treatment has been commenced.

In accordance with one aspect of the invention, the application thus relates to a method, more particularly an in vitro method, for predicting whether a subject infected with one or more hepatitis C viruses has a high probability of responding to an anti-HCV treatment which will comprise administering interferon and ribavirin or whether, in contrast, this subject has a high probability of not responding to this anti-HCV treatment.

The method includes the fact of measuring the levels to which the selected genes are transcribed or translated, said selected genes being genes selected from the following list of genes: MBL2, LGALS3BP and IL8, G1P2, CXCL10, CCL21, AFP, CRP, CXCL11, CXCL6, CXCL9, FGF7, MDK, MMP2, SFN, TGFB2 and VEGFD.

More particularly, the predictive method of the application comprises the fact of measuring the levels to which the selected genes are transcribed or translated, said selected genes being:
at least one gene from among MBL2, LGALS3BP and IL8, and
at least one gene from among G1P2, CCL21 and CXCL10, and
optionally, at least one gene from among AFP, CRP, CXCL11, CXCL6, CXCL9, FGF7, MDK, MMP2, SFN, TGFB2 and VEGFD.

These measurements may be carried out in a sample which has been obtained from said subject.

In the predictive method of the invention, the total number of genes selected is 2, 3, 4 or 5.

This being the case, as is presented and illustrated in more detail below, the predictive method of the invention may also comprise measuring or assaying one or more factors, in particular one or more virological factors and/or one or more clinical factors and/or one or more biological factors other than the levels of expression of genes selected from MBL2, LGALS3BP and IL8, G1P2, CXCL10, CCL21, AFP, CRP, CXCL11, CXCL6, CXCL9, FGF7, MDK, MMP2, SFN, TGFB2 and VEGFD.

A predictive method of the invention can thus be defined by the fact that it comprises the step of carrying out measurements which comprise or are constituted by the following measurements:
in a sample which has already been obtained from said subject, measuring the levels to which the selected genes have been transcribed or translated, said selected genes being:
at least one gene from among MBL2, LGALS3BP and IL8, and
at least one gene from among G1P2, CCL21 and CXCL10, and
optionally, at least one gene from among AFP, CRP, CXCL11, CXCL6, CXCL9, FGF7, MDK, MMP2, SFN, TGFB2 and VEGFD,
the total number of the genes selected thereby being 2, 3, 4 or 5,
optionally, measuring or determining, for said subject, the value of one or more clinical factors and/or of one or more virological factors and/or of one or more biological factors other than the levels of expression of genes selected from MBL2, LGALS3BP and IL8, G1P2, CXCL10, CCL21, AFP, CRP, CXCL11, CXCL6, CXCL9, FGF7, MDK, MMP2, SFN, TGFB2 and VEGFD.

The application also relates to an anti-HCV therapy method which comprises the fact of predicting the response of a subject to an anti-HCV treatment with the aid of the predictive method of the invention. If said subject is predicted to be a non-responder, the clinician may elect not to administer a treatment which comprises (more particularly which is essentially constituted by) administering interferon and administering ribavirin (or their prodrugs), more particularly of not administering such a treatment as a first line treatment. In such a situation, the clinician may, for example, elect to administer an anti-HCV treatment which does not include (or is not essentially constituted by) administering interferon and administering ribavirin (or their prodrugs), more particularly of administering such a treatment as a first line treatment. The clinician may alternatively elect not to administer the anti-HCV treatment, at least as a first line treatment. If said subject is predicted to be a responder, the clinician may elect to administer an anti-HCV treatment, in particular a treatment which comprises (more particularly is essentially constituted by) administering interferon and administering ribavirin (or their prodrugs), more particularly of administering a first line treatment which comprises (more particularly which is essentially constituted by) administering interferon and administering ribavirin (or their prodrugs).

Measuring (or assaying) the level of expression of said selected genes may be carried out in a sample which has been obtained from said subject, such as:
  a biological sample removed from or collected from said subject, or
  a sample comprising nucleic acids (in particular RNAs) and/or proteins and/or polypeptides and/or peptides of said biological sample, in particular a sample comprising nucleic acids and/or proteins and/or polypeptides and/or peptides which have been or are susceptible of having been extracted and/or purified from said biological sample, or
  a sample comprising cDNAs which have been or are susceptible of having been obtained by reverse transcription of said RNAs.

A biological sample collected or removed from said subject may, for example, be a sample removed or collected or susceptible of being removed or collected from:
  an internal organ or tissue of said subject, in particular from the liver or the hepatic parenchyma, or
  a biological fluid from said subject, in particular an intracorporal fluid such as the blood, serum, plasma or urine.

A biological sample collected or removed from said subject may, for example, be a sample comprising a portion of tissue from said subject, in particular a portion of hepatic tissue, more particular a portion of the hepatic parenchyma.

A biological sample collected or removed from said subject may, for example, be a sample comprising cells which have been or are susceptible of being removed or collected from a tissue of said subject, in particular from a hepatic tissue, more particularly hepatic cells.

A biological sample collected or removed from said subject may, for example, be a sample comprising a sample of biological fluid such as a sample of blood, serum, plasma or urine, more particularly a sample of intracorporal fluid such as a sample of blood or serum or plasma. In fact, the seventeen genes from said list of the invention all code for non-membrane proteins, and the product of their expression in particular have an extracellular localization.

In accordance with an advantageous embodiment of the invention, said biological sample is thus a sample of a biological fluid from said subject, such as a sample of intracorporal fluid, such as a blood, serum, plasma or urine sample, and the levels of expression of said selected genes which are assayed may be levels of protein translation.

Said biological sample may be removed or collected by inserting a sampling instrument, in particular by inserting a needle or a catheter, into the body of said subject. This instrument may, for example be inserted:
  into an internal organ or tissue of said subject, in particular into the liver or into the hepatic parenchyma, for example:
    to remove a sample of liver or hepatic parenchyma, said removal possibly, for example, being carried out by hepatic biopsy puncture (HBP), more particularly by transjugular or transparietal HBP, or
    to remove or collect cells from the hepatic compartment (removal of cells and not of tissue), more particularly from the hepatic parenchyma, in particular to remove hepatic cells, this removal or collection possibly being carried out by hepatic cytopuncture;
  and/or
  into a vein, an artery or a vessel of said subject in order to remove a biological fluid from said subject, such as blood.

The means of the invention are not limited to being deployed on a tissue biopsy, in particular hepatic tissue. They may be deployed on a sample obtained or susceptible of being obtained by taking a sample with a size or volume which is substantially smaller than a tissue sample, namely a sample which is limited to a few cells. In particular, the means of the invention can be deployed on a sample obtained or susceptible of being obtained by hepatic cytopuncture.

The quantity or the volume of material removed by hepatic cytopuncture is much smaller than that removed by HBP. In addition to the immediate gain for the patient in terms of reducing the invasive nature of the technique and reducing the associated morbidity, hepatic cytopuncture has the advantage of being able to be repeated at distinct times for the same patient (for example to determine the change in the hepatic fibrosis between two time periods), while HBP cannot reasonably be repeated on the same patient. Thus, in contrast to HBP, hepatic cytopuncture has the advantage of allowing clinical changes in the patient to be monitored.

Thus, in accordance with the invention, said biological sample may advantageously be:
  cells removed or collected from the hepatic compartment (removal or collection of cells and not of tissue), more particularly from the hepatic parenchyma, i.e. a biological sample obtained or susceptible of being obtained by hepatic cytopuncture;
and/or
  biological fluid removed or collected from said subject, such as blood or urine, in particular blood.

The measurement (or assay) may be carried out in a biological sample which has been collected or removed from said subject and which has been transformed, for example:
  by extraction and/or purification of nucleic acids, in particular RNAs, more particularly mRNAs, and/or by reverse transcription of said RNAs, in particular of said mRNAs, or
  by extraction and/or purification of proteins and/or polypeptides and/or peptides, or by extraction and/or purification of a protein fraction such as serum or plasma extracted from blood.

As an example, when the collected or removed biological sample is a biological fluid such as blood or urine, before carrying out the measurement or the assay, said sample may be transformed:
  by extraction of nucleic acids, in particular RNA, more particularly mRNA, and/or by reverse transcription of said RNAs, in particular of said mRNAs (most generally by extraction of RNAs and reverse transcription of said RNAs), or
  by separation and/or extraction of the seric fraction or by extraction or purification of seric proteins and/or polypeptides and/or peptides.

Thus, in one embodiment of the invention, said sample obtained from said subject comprises (for example in a solution), or is, a sample of biological fluid from said subject, such as a sample of blood, serum, plasma or urine, and/or is a sample which comprises (for example in a solution):
RNAs, in particular mRNAs, which are susceptible of having been extracted or purified from a biological fluid such as blood or urine, in particular blood; and/or
cDNAs which are susceptible of having been obtained by reverse transcription of said RNAs; and/or
proteins and/or polypeptides and/or peptides which are susceptible of having been extracted or purified from a biological fluid, such as blood or urine, in particular blood, and/or susceptible of having been encoded by said RNAs,
preferably
proteins and/or polypeptides and/or peptides which are susceptible of having been extracted or purified from a biological fluid, such as blood or urine, in particular blood, and/or susceptible of having been encoded by said RNAs.

When said sample obtained from said subject comprises a biological sample obtained or susceptible of being obtained by sampling a biological fluid such as blood or urine, or when said sample obtained from said subject is obtained or susceptible of having been obtained from said biological sample by extraction and/or purification of molecules contained in said biological sample, the measurement is preferably a measurement of proteins and/or polypeptides and/or peptides, rather than measuring nucleic acids.

When the biological sample which has been collected or removed is a sample comprising a portion of tissue, in particular a portion of hepatic tissue, more particularly a portion of the hepatic parenchyma such as, for example, a biological sample removed or susceptible of being removed by hepatic biopsy puncture (HBP), or when the biological sample collected or removed is a sample comprising cells obtained or susceptible of being obtained from such a tissue, such as a sample collected or susceptible of being collected by hepatic cytopuncture, for example, said biological sample may be transformed:
by extraction of nucleic acids, in particular RNA, more particularly mRNA, and/or by reverse transcription of said RNAs, in particular said mRNAs (most generally by extraction of said RNAs and reverse transcription of said RNAs), or
by separation and/or extraction of proteins and/or polypeptides and/or peptides.

A step for lysis of the cells, in particular lysis of the hepatic cells contained in said biological sample, may be carried out in advance in order to render nucleic acids or, if appropriate, proteins and/or polypeptides and/or peptides, directly accessible to the analysis.

Thus, in one embodiment of the invention, said sample obtained from said subject is a sample of tissue from said subject, in particular hepatic tissue, more particularly hepatic parenchyma, or is a sample of cells of said tissue and/or is a sample which comprises (for example in a solution):
hepatic cells, more particularly cells of the hepatic parenchyma, for example cells obtained or susceptible of being obtained by dissociation of cells from a biopsy of hepatic tissue or by hepatic cytopuncture; and/or
RNAs, in particular mRNAs, which are susceptible of having been extracted or purified from said cells; and/or
cDNAs which are susceptible of having been obtained by reverse transcription of said RNAs; and/or
proteins and/or polypeptides and/or peptides which are susceptible of having been extracted or purified from said cells and/or susceptible of having been coded for by said RNAs.

In accordance with the invention, said subject is a human being or a non-human animal, in particular a human being or a non-human mammal, more particularly a human being.

Because of the particular selection of genes proposed by the invention, the status of responder or non-responder of said subject may be deduced or determined from values for the measurements obtained for said subject, in particular by statistical inference and/or statistical classification, for example using reference cohorts (pre)-established according to their status of responder or non-responder.

In addition to measuring (or assaying) the level to which the selected genes are expressed in the organism of said subject, a method of the invention may thus further comprise a step for deducing or determining the status of responder or non-responder of said subject from values for measurements obtained for said subject. This step for deduction or determination is a step in which the values for the measurements obtained for said subject are analysed in order to infer therefrom the status of responder or non-responder of said subject.

The status of responder or non-responder of said subject may be deduced or determined by comparing the values for measurements obtained from said subject with their values or the distribution of their values, in reference cohorts which have already been set up as a function of their status as responder or non-responder to anti-HCV treatment, in order to classify said subject into that of those reference cohorts to which it has the highest probability of belonging (i.e. to attribute to said subject its status of responder or non-responder). The individuals composing those cohorts are individuals for whom it has been established that they are responders or non-responders to this treatment by applying that anti-HCV treatment.

The measurements made on said subject and on the individuals of the reference cohorts or sub-populations are measurements of the levels of gene expression (transcription or translation).

In order to measure the level of transcription of a gene, its level of RNA transcription is msd. Such a measurement may, for example, comprise assaying the concentration of transcribed RNA of each of said selected genes, either by assaying the concentration of these RNAs or by assaying the concentration of cDNAs obtained by reverse transcription of these RNAs. The measurement of nucleic acids is well known to the skilled person. As an example, the measurement of RNA or corresponding cDNAs may be carried out by amplifying nucleic acid, in particular by PCR. Some reagents are described below for this purpose (see Example 1 below). Examples of appropriate primers and probes are also given (see, for example, Table 32 below). The conditions for amplification of the nucleic acids may be selected by the skilled person. Examples of amplification conditions are given in the "Examples" section which follows (see Example 1 below).

In order to measure the level of translation of a gene, its level of protein translation is measured. Such a measurement may, for example, comprise assaying the concentration of proteins translated from each of said selected genes (for example, measuring the proteins in the general circulation, in particular in the serum). Protein measurement is well known to the skilled person. As an example, the proteins (and/or polypeptides and/or peptides) may be measured by ELISA or any other immunometric method which is known to the skilled person, or by a method using mass spectrometry which is known to the skilled person.

The measurement values are values of concentration or proportion, or values which represent a concentration or a proportion. The aim is that within a given combination, the measurement values for the levels of expression of each of said selected genes reflect as accurately as possible, at least with respect to each other, the degree to which each of these genes is expressed (degree of transcription or degree of translation), in particular by being proportional to these respective degrees.

As an example, in the case of measurement of the level of expression of a gene by measurement of transcribed RNAs, i.e. in the case of measurement of the level of transcription of this gene, the measurement is generally carried out by amplification of the RNAs by reverse transcription and PCR (RT-PCR) and by measuring values for Ct (cycle threshold).

A value for Ct provides a measure of the initial quantity of amplified RNAs (the smaller the value for Ct, the larger the quantity of these nucleic acids). The Ct values measured for a target RNA ($Ct_{target}$) are generally related to the total quantity of RNA initially present in the sample, for example by deducing, from this $Ct_{target}$, the value for a reference Ct ($Ct_{reference}$), such as the value of Ct which was measured under the same operating conditions for the RNA of an endogenous control gene for which the level of expression is stable (for example, a gene involved in a cellular metabolic cascade, such as RPLP0 or TBP; see Example 1 below).

In one embodiment of the invention, the difference ($Ct_{target}-Ct_{reference}$), or $\Delta Ct$, may also be exploited by the method known as the $2^{-\Delta Ct}$ method (Livak and Schmittgen 2001; Schmittgen and Livak 2008), with the form:

$$2^{-\Delta Ct}=2^{-(Ct\ target-Ct\ reference)}$$

Hence, in one embodiment of the invention, the levels to which each of said selected genes is transcribed are measured as follows:
  by amplification, of a fragment of the RNAs transcribed by each of said selected genes, for example by reverse transcription and PCR of these RNA fragments in order to obtain the Ct values for each of these RNAs,
  optionally, by normalisation of each of these Ct values with respect to the value for Ct obtained for the RNA of an endogenous control gene, such as RPLP0 or TBP, for example by the $2^{-\Delta Ct}$ method,
  optionally, by Box-Cox transformation of said normalized values for Ct.

In the case of measuring the level of expression of a gene by measuring proteins expressed by that gene, i.e. in the case of measuring a level of translation of that gene, the measurement is generally carried out by an immunometric method using specific antibodies, and by expression of the measurements made thereby in quantities by weight or international units using a standard curve. Examples of specific antibodies are indicated in Table 29 below. Examples of protein measurement means are given in Table 44 below. A value for the measurement of the level of translation of a gene may, for example, be expressed as the quantity of this protein per volume of biological fluid, for example per volume of serum (in mg/mL or in µg/mL or in ng/mL or in pg/mL, for example).

If desired or required, the distribution of the measurement values obtained for the individuals of a cohort may be smoothed so that it approaches a Gaussian law.

To this end, the measurement values obtained for individuals of that cohort, for example the values obtained by the $2^{-\Delta t}$ method, may be transformed by a transformation of the Box-Cox type (Box and Cox, 1964; see Tables 5, 10, 15, 19, 23 and 27 below; see Examples 2 to 4 below).

Thus, the application relates to an in vitro method for predicting whether a subject infected with one or more HCVs has a strong probability of being a responder to an anti-HCV treatment which will comprise the administration of interferon and ribavirin or whether, in contrast, that subject has a strong probability of not being a responder to this anti-HCV treatment, said method comprising the following steps:
  i) making the following measurements:
    in a sample which has previously been obtained from said subject, measuring the levels to which selected genes have been transcribed or translated, said selected genes being:
      at least one gene from among MBL2, LGALS3BP and IL8, and
      at least one gene from among G1P2, CCL21 and CXCL10, and
      optionally, at least one gene from among AFP, CRP, CXCL11, CXCL6, CXCL9, FGF7, MDK, MMP2, SFN, TGFB2 and VEGFD,
    the total number of the genes selected thereby being 2, 3, 4 or 5,
    optionally, measuring or determining, for said subject, the value of one or more clinical factors and/or of one or more virological factors and/or of one or more biological factors other than the levels of expression of genes selected from MBL2, LGALS3BP and IL8, G1P2, CXCL10, CCL21, AFP, CRP, CXCL11, CXCL6, CXCL9, FGF7, MDK, MMP2, SFN, TGFB2 and VEGFD,
  ii) comparing the values for the measurements obtained for said subject in step i) with their values, or the distribution of their values, in reference cohorts which have been pre-established as a function of their status of responder or non-responder to anti-HCV treatment, in order to classify said subject into that of those reference cohorts with respect to which it has the highest probability of belonging.

The comparison of step ii) may in particular be made by combining the measurement (or assay) values obtained for said subject in a multivariate classification model.

Such a multivariate classification model compares (in a combined manner) values of measurements obtained for said subject with their values or with the distribution of their values in reference cohorts which have been pre-established as a function of their status of responder or non-responder to anti-HCV treatment, in order to classify said subject into that of those reference cohorts with respect to which it has the strongest probability of belonging, for example by attributing to it an output value which indicates the status of responder or non-responder of said subject.

Such a multivariate classification model may be constructed, in particular constructed in advance, by making an inter-cohort comparison of the values of measurements obtained for said reference cohorts or of distributions of those measurement values.

More particularly, such a multivariate classification model may be constructed, in particular constructed in advance, by measuring or assaying the levels of expression of said genes selected from reference cohorts pre-established as a function of their status of responder or non-responder to anti-HCV treatment, and by analysing these measurement values or their distribution using a multivariate statistical method in order to construct a multivariate classification model which infers or determines a status of responder or non-responder to anti-HCV treatment from the values for the levels of expression of said selected genes.

If in addition to values for the measurement of the levels of transcription or translation of said selected genes, the values measured for said subject comprise the value or values for one or more other factors, such as one or more virological factors and/or one or more clinical factors and/or one or more other biological factors (see below and in the Examples), the classification model is of course constructed, in particular constructed in advance, by measuring or assaying the same values in reference cohorts which have been pre-established as a function of whether they have the status of responder or non-responder to anti-HCV treatment, and by analysing these values or their distribution by means of a multivariate statistical method in order to construct a multivariate classification model which infers or determines a status of responder or non-responder to anti-HCV treatment from these values.

As an example, a model may be constructed by a mathematical function, a non-parametric technique, a heuristic classification procedure or a probabilistic predictive approach. A typical example of classification based on the quantification of the level of expression of biomarkers consists of distinguishing between "healthy" and "sick" subjects. The formalization of this problem consists of m independent samples, described by n random variables. Each individual i (i=1, . . . , m) is characterized by a vector $x_i$ describing the n characteristic values:

$$x_{ij}, i=1, \ldots m\ j=1, \ldots n$$

These characteristic values may, for example, represent gene expression values and/or the intensities of protein data and/or the intensities of metabolic data and/or clinical data.

Each sample $x_i$ is associated with a discreet value $y_i$, representing the clinical status of the individual i. By way of example, $y_i$=0 if the patient i has a status of non-responder to anti-HCV treatment, $y_i$=1 if the patient i has a status of responder to anti-HCV treatment.

A model offers a decision rule (for example a mathematical function, an algorithm or a procedure) which uses the information available from $x_i$ to predict $y_j$ in each sample observed. The aim is to use this model in order to predict the clinical status of a patient p, namely $y_p$, from available biological and/or clinical values, namely $x_p$.

A variety of multivariate classification models is known to the skilled person (see Hastie, Tibishirani and Friedman, 2009; Falissard, 2005; Theodoridis and Koutroumbos 2009). They are generally constructed by processing and interpreting data by means, for example, of:
  a multivariate statistical analysis method, for example:
    a linear or non-linear mathematical function, in particular a linear mathematical function such as a function generated by the mROC method (multivariate ROC method), or
    a ROC (Receiver Operating Characteristics) method;
    a linear or non-linear regression method, such as the logistical regression method, for example;
    a PLS-DA (Partial Least Squares-Discriminant Analysis) method;
    a LDA (Linear Discriminant Analysis) method;
  a machine learning or artificial intelligence method, for example a machine learning or artificial intelligence algorithm, a non-parametric, or heuristic, classification method or a probabilistic predictive method such as:
    a decision tree; or
    a boosting type method based on binary classifiers (example: Adaboost) or a method linked to boosting (bagging); or
    a k-nearest neighbours (or KNN) method, or more generally the weighted k-nearest neighbours method (or WKNN), or
    a Support Vector Machine (or SVM) method (for example an algorithm); or
    a Random Forest (or RF); or
    a Bayesian network; or
    a Neural Network; or
    a Galois lattice or Formal Concept Analysis.

The decision rules for the multivariate classification models may, for example, be based on a mathematical formula of the type $y=f(x_1, x_2, \ldots x_n)$ where f is a linear or non-linear mathematical function (logistic regression, mROC, for example), or on a machine learning or artificial intelligence algorithm the characteristics of which consist of a series of control parameters identified as being the most effective for the discrimination of subjects (for example, KNN, WKNN, SVM, RF).

The multivariate ROC method (mROC) is a generalisation of the ROC (Receiver Operating Characteristic) method (see Reiser and Faraggi 1997; Su and Liu 1993, Shapiro, 1999). It calculates the area under the ROC curve (AUC) relative to a linear combination of biomarkers and/or biomarker transformations (in the case of normalization), assuming a multivariate normal distribution. The mROC method has been described in particular by Kramar et al. 1999 and Kramar et al. 2001. Reference is also made to the examples below, in particular point 2 of Example 1 below (mROC model).

The mROC version 1.0 software, commercially available from the designers (A. Kramar, A. Fortune, D. Farragi and B. Reiser) may, for example, be used to construct a mROC model.

Andrew Kramar and Antoine Fortune can be contacted at or via the Unité de Biostatistique du Centre Régional de Lutte contre le Cancer (CRLC) [Biostatistics Unit, Regional Cancer Fighting Centre], Val d'Aurelle—Paul Lamarque (208, rue des Apothicaires; Parc Euromédecine; 34298 Montpellier Cedex 5; France).

David Faraggi and Benjamin Reiser can be contacted at or via the Department of Statistics, University of Haifa (Mount Carmel; Haifa 31905; Israel).

The family of artificial intelligence or machine learning methods is a family of algorithms which, instead of proceeding to an explicit generalization, compares the examples of a new problem with examples considered to be training examples and which have been stored in the memory. These algorithms directly construct hypotheses from the training examples themselves. A simple example of this type of algorithm is the k-nearest neighbours (or KNN) model and one of its possible extensions, known as the weighted k nearest neighbours (or WKNN) algorithm (Hechenbichler and Schliep, 2004).

In the context of the classification of a new observation x, the simple basic idea is to make the nearest neighbours of this observation count. The class (or clinical status) of x is determined as a function of the major class from among the k nearest neighbours of the observation x.

Libraries of specific KKNN functions are available, for example, from R software (http://www. R-project.org/). R software was initially developed by John Chambers and Bell Laboratories (see Chambers 2008). The current version of this software suite is version 2.11.1. The source code is freely available under the terms of the "Free Software Foundation's GNU" public licence at the website http://www.R-project.org/. This software may be used to construct a WKNN model.

Reference is also made to the examples below, in particular to point 2 of Example 1 below (WKNN model).

A Random Forest (or RF) model is constituted by a set of simple tree predictors each being susceptible of producing a response when it is presented with a sub-set of predictors (Breiman 2001; Liaw and Wiener 2002). The calculations are made with R software. This software may be used to construct RF models.

Reference is also made to the examples below, in particular to point 2 of Example 1 below (RF model).

A neural network is constituted by an orientated weighted graph the nodes of which symbolize neurons. The network is constructed from examples of each class (for example F2 versus F1) and is then used to determine to which class a new element belongs; see Intrator and Intrator 1993, Riedmiller and Braun 1993, Riedmiller 1994, Anastasiadis et al. 2005; see http://cran.r-project.org/web/packages/neuralnet/index.html.

R software, which is freely available from http://www.r-project.org/, (version 1.3 of Neuralnet, written by Stefan Fritsch and Frauke Guenther following the work by Marc Suling) may, for example, be used to construct a neural network.

Reference is also made to the examples below, in particular to point 2 of Example 1 below (NN model).

The comparison of said step ii) may thus in particular be carried out by using the following method and/or by using the following algorithm or software:
  mROC,
  KNN, WKNN, more particularly WKNN,
  RF, or
  NN,
more particularly mROC.

Each of these algorithms, or software or methods, may be used to construct a multivariate classification model from values for measurements of each of said reference cohorts, and to combine the values of the measurements obtained for said subject in this model to deduce therefrom a status of responder or non-responder for the subject.

In one embodiment of the invention, the multivariate classification model implemented in the method of the invention is expressed by a mathematical function, which may be linear or non-linear, more particularly a linear function (for example, a mROC model). The status of responder or of non-responder of said subject is thus deduced by combining said measurement values obtained for said subject in this mathematical function, in particular a linear or non-linear function, in order to obtain an output value, more particularly a numerical output value, which is an indicator of the status of responder or of non-responder of said subject.

In one embodiment of the invention, the multivariate classification model implemented in the method of the invention is a learning or artificial intelligence model, a non-parametric classification model or heuristic model or a probabilistic prediction model (for example, a WKNN, RF or NN model). The status of responder or of non-responder of said subject is thus induced by combining said measurement values obtained for said subject in a non-parametric classification model or heuristic model or a probabilistic prediction model (for example, a WKNN, RF or NN model) in order to obtain an output value, more particularly an output tag, indicative of the status of responder or of non-responder of said subject.

Alternatively or in a complementary manner, said comparison of step ii) may include the fact of comparing the values for the measurements obtained for said subject with at least one reference value which discriminates between a status of responder or of non-responder, in order to classify said subject into the group of responder individuals or into the group of non-responder individuals.

As an example, the values for the measurements may be compared to their reference values in:
  a sub-population of individuals of the same species as said subject, who are infected with the HCV, to whom the anti-HCV treatment has been administered, and who have been shown to be responders to this treatment, and/or
  a sub-population of individuals of subjects of the same species as said subject, infected with the HCV, to whom the anti-HCV treatment has been administered and who have been shown to be non-responders to this treatment,
or to a reference value which represents the combination of these reference values.

A reference value may, for example, be:
  the value for the measurement of the level of expression of each of said selected genes in each of the individuals for each of the sub-populations or reference cohorts, or
  a positional criterion, for example the mean or median, or a quartile, or the minimum, or the maximum of these values in each of these sub-populations or reference cohorts, or
  a combination of these values or means, median, or quartile, or minimum, or maximum.

The reference value or values used must be able to allow the status of responder to be distinguished from that of non-responder.

It may, for example, concern a decision or prediction threshold established as a function of the distribution of the values for the measurements in each of said sub-populations or cohorts, and as a function of the levels of sensitivity (Se) and specificity (Spe) set by the user (Se=TP/(TP+FN) and Sp=TN/(TN+FP), with TP=number of true positives, FN=number of false negatives, TN=number of true negatives, and FP=number of false positives). This decision or prediction threshold may in particular be an optimal threshold which attributes an equal weight to the sensitivity (Se) and to the specificity (Spe), such as the threshold maximizing Youden's index (J) defined by J=Se+Spe−1.

Alternatively or in a complementary manner, several reference values may be compared. This is the case in particular when the values for the measurements obtained for said subject are compared with their values in each of said sub-populations or reference cohorts, for example with the aid of a machine learning or artificial intelligence classification method.

Thus, the comparison of step ii) may, for example, be carried out as follows:
  select the levels of sensitivity (Se) and specificity (Spe) to be given to the method,
  establish a mathematical function, linear or non-linear, in particular a linear mathematical function (for example, by the mROC method), starting from measurement values for said genes in each of said sub-populations or cohorts, and calculate the decision or prediction threshold associated with this function due to the choices of levels of sensitivity (Se) and specificity (Spe) made (for example, by calculating the threshold maximizing Youden's index), combine the measurement values obtained for said subject into this mathematical function, in order to obtain an output value which, compared with said decision or prediction threshold, can be used to attribute a status of responder or a status of non-responder to said subject, i.e. to classify said subject into that of these sub-populations or reference cohorts to which it has the greatest probability of belonging.

In particular, the invention is based on the demonstration that, when taken in combination, the levels of expression of:

at least one gene from among MBL2, LGALS3BP and IL8, and at least one gene from among G1P2, CCL21 and CXCL10, and optionally, at least one gene from among AFP, CRP, CXCL11, CXCL6, CXCL9, FGF7, MDK, MMP2, SFN, TGFB2 and VEGFD, are biomarkers which provide a "signature" which is predictive of the status of responder or of non-responder.

The skilled person having available a combination of genes described by the invention is in a position to construct a multivariate classification model, in particular a multivariate statistical analysis model (for example a linear or non-linear mathematical function) or a machine learning or artificial intelligence model (for example, a machine learning or artificial intelligence algorithm), with the aid of his general knowledge in the field of statistical techniques and means, in particular in the domain of statistical processing and interpretation of data, more particularly biological data.

A multivariate classification model may, for example, be constructed, in particular constructed in advance, as follows:

a) for a population of individuals of the same species as said subject, and who are infected with one or more HCVs, determining for each of these individuals whether or not that individual responds to an anti-HCV treatment which comprises the administration of interferon and of ribavirin, and classifying these individuals into distinct sub-populations depending on whether they have been shown to be responders or non-responders to this treatment, thus constituting reference cohorts established as a function of the response or non-response of these individuals to anti-HCV treatment;

b) in at least one sample which has already been obtained from each of said individuals, the nature of which is identical to that of the sample from said subject, carrying out the same measurements as those carried out for said subject in said step i);

c) carrying out an inter-cohort comparison of the values of the measurements obtained in step b), or the distribution of these values, in order to construct a multivariate classification model which infers a status of responder to anti-HCV treatment or a status of non-responder to said treatment, starting from the combination of said values of the measurements obtained in step b).

If said subject or subjects for whom the status of responder or non-responder is to be determined present this fibrosis due to a particular known chronic hepatic disease, for example due to an infection with a particular HCV genotype, then advantageously, individuals with a comparable clinical situation are used. The individuals are also selected so as to constitute a statistically acceptable cohort having no particular bias, in particular no particular clinical bias. The aim is to construct a multivariate classification model which is as relevant as possible from a statistical point of view.

Preferably, the cohorts or sub-populations of individuals comprise as many individuals as possible. If the number of individuals is too low, the comparison or the constructed model might not be sufficiently reliable and generalizable in view of the envisaged medical applications.

In particular, cohorts or sub-populations will be selected which each comprise at least 30 individuals, for example at least 40 individuals, preferably at least 50 individuals, more particularly at least 70 individuals, and still more particularly at least 100 individuals.

Preferably, a comparable number of individuals is present in each cohort or sub-population. As an example, the number of individuals of a cohort or sub-population does not exceed the threshold of 3 times the number of individuals of another cohort, more particularly the threshold of 2.5 times the number of individuals of another cohort.

When the statistical analysis carried out uses a mathematical function, such as in the case of a mROC method, for example, the number of individuals required per cohort may optionally be of the order of 20 to 40 individuals per reference cohort. In the case of a machine learning analysis method, such as a KNN, WKNN, RF or NN method, it is preferable to have at least 30 individuals per cohort, preferably at least 70 individuals, still more particularly at least 100 individuals. In the examples that follow, the total number of individuals included in the set of cohorts is more than 120.

The individuals who make up the reference cohorts are individuals who have received an anti-HCV treatment and for whom the status of responder or non-responder has been determined after application of that treatment, in particular by measuring the HCV load of these individuals at the end of treatment and if this load has become undetectable, 6 months after treatment.

In order to determine the status of responder or of non-responder of an individual, and consequently of attributing that individual to a reference cohort, the skilled person can employ any means that is judged appropriate. The VERSANT® HCV-RNA 3.0 (bDNA) ASSAY HCV RNA quantification test from Siemens Healthcare Diagnostics (quantification limit=615–7 690 000 IU/mL) is an example of means that can be used to measure the viral load and to determine whether that load has become undetectable at the end of the treatment and remains so 6 months after treatment (responder individuals) or whether said load is still detectable at the end of treatment (non-responder individuals).

Although the number of samples taken from a given individual should of course be limited, in particular in the case of hepatic biopsy puncture, several samples can be collected from the same individual. In this case, the results of measuring the various samples of the same individual are considered as their resultant mean; it is not assumed that they could be equivalent to the measurement values obtained from distinct individuals.

The comparison of the values of the measurements in each of said cohorts may be carried out using any means known to the skilled person. It is generally carried out by statistical treatment and interpretation of those values. This multivariate statistical comparison can be used to construct a multivariate classification model which infers a value for the status of responder or non-responder from the combination of these values.

Once said multivariate classification model has been constructed, it can be used to analyse the values of measurements obtained for said subject, and above all be re-used for the analysis of the values of measurements from other subjects. Thus, said multivariate classification model can be established independently of measurements made for said subject or said subjects and may be constructed in advance.

Should it be necessary, rather than constitute the cohorts and combine the data from the individuals who make them up, in order to construct examples of multivariate classification models in accordance with the invention, the skilled person may use subjects who are described in the Examples section below as individuals of the cohorts and may, in the context of individual cohort data, use the data which are presented for these subjects in the Examples below, more particularly in Tables 34 to 36 below.

Preferably, said multivariate classification model is a particularly discriminating system. Advantageously, said multivariate classification model has a particular area under the ROC curve (or AUC) and/or LOOCV error value.

The acronym "AUC" denotes the Area Under the Curve, and ROC denotes the Receiver Operating Characteristic. The acronym "LOOCV" denotes Leave-One-Out-Cross-Validation, see Hastie, Tibishirani and Friedman, 2009.

The characteristic of AUC is that it can be applied in particular to multivariate classification models which are defined by a mathematical function such as, for example, the models using a mROC classification method.

Multivariate artificial intelligence or machine learning models cannot properly be said to be defined by a mathematical function. Nevertheless, since they involve a decision threshold, they can be understood by means of a ROC curve, and thus by an AUC calculation. This is the case, for example, with models using a RF (random forest) method. In fact, in the case of the RF method, a ROC curve may be calculated from predictions of OOB (out-of-bag) samples.

In contrast, those of the multivariate artificial intelligence or machine learning models which could not be characterized by an AUC value, in common with all other multivariate artificial intelligence or machine learning models, can be characterized by the value of the "classification error" parameter which is associated with them, such as the value for the LOOCV error, for example.

Said particular value for the AUC may in particular be at least 0.76, at least 0.77, at least 0.78, more particularly at least 0.79, still more particularly at least 0.80, at least 0.81, at least 0.82, at least 0.83, at least 0.84, more particularly at least 0.85, still more particularly at least 0.86, still more particularly at least 0.87, for example at least 0.88, 0.89 or 0.90 (preferably, with a 95% confidence interval of at most ±11%, more particularly of less than ±10.5%, still more particularly of less than ±9.5%, in particular of less than ±8.5%); see for example, combination Nos. 1 to No. 43 in Tables 6, 11, 16, 20, 24, 28 below.

Advantageously, said particular LOOCV error value is at most 18%, at most 17%, at most 16%, at most 15%, at most 14%, at most 13%, at most 12%, at most 11%, more than 10%, more than 9%, more than 8%, more than 7%, more than 6%, more than 5%, more than 4%, more than 3%, more than 2%, more than 1% (see for example, combination Nos. 1 to 8, 10 to 14, 16 to 29 in Table 13 below).

The diagnostic performances of a biomarker are generally characterized in accordance with at least one of the following two indices:

the sensitivity (Se), which represents its capacity to detect the population termed "pathological" constituted by individuals termed "cases" (in fact, patients who have a status of non-responders);

the specificity (Sp or Spe), which represents its capacity to detect the population termed "healthy", constituted by patients termed "controls" (in fact, patients who have a status of responders).

When a biomarker generates continuous values (for example concentration values), different positions of the Prediction Threshold (or PT) may be defined in order to assign a sample to the positive class (positive test: y=1). The comparison of the concentration of the biomarker with the PT value means that the subject can be classified into the cohort to which it has the highest probability of belonging.

As an example, if a cohort of individuals which have a status of responders and a cohort of individuals which have a status of non-responders are considered, and if a subject or patient p is considered for whom the status is to be determined and for whom the value of the combination of measurements is V (V being equal to Z in the case of mROC models), the decision rule is as follows:

when the mean value for the combination of measurements in the cohort of "responder" individuals is less than that of the cohort of "non-responder" individuals:
if V≥PT: the test is positive, a status of non-responder is assigned to said patient p,
if V<PT: the test is negative, a status of responder is assigned to said patient p, or when the mean value of the combination of measurements in the cohort of "responder" individuals is higher than that of the cohort of "non-responder" individuals:
if V≥PT: the test is negative, a status of responder is assigned to said patient P,
if V<PT: the test is positive, a status of non-responder is assigned to said patient p.

Since the combination of biomarkers of the invention is effectively discriminate, the distributions, which are assumed to be Gaussian, of the combination of biomarkers in each population of interest are clearly differentiated. Thus, the optimal threshold value which will provide this combination of biomarkers with the best diagnostic performances can be defined.

In fact, for a given threshold PT, the following values may be calculated:
the number of true positives: TP;
the number of false negatives: FN;
the number of false positives: FP;
the number of true negatives: TN.

The calculations of the parameters of sensitivity (Se) and specificity (Sp) are deduced from the following formulae:

$$Se=TP/(TP+FN);$$

$$Sp=TN/(TN+FP).$$

The sensitivity can thus be considered to be the probability that the test is positive, knowing that the status of the subject is a status of non-responder; and the specificity can be considered to be the probability that the test is negative, knowing that the status of the subject is a status of responder.

An ROC curve can be used to visualize the predictive power of the biomarker (or, for the multivariate approach, the predictive power of the combination of biomarkers integrated into the model) for different values of PT (Swets 1988). Each point of the curve represents the sensitivity versus (1-specificity) for a specific PT value.

For example, if the concentrations of the biomarker of interest vary from 0 to 35, different PT values may be successively positioned at 0.5; 1; 1.5; . . . ; 35. Thus, for each PT value, the test samples are classified, the sensitivity and the specificity are calculated and the resulting points are recorded on a graph.

The closer the ROC curve comes to the first diagonal (straight line linking the lower left hand corner to the upper right hand corner), the worse is the discriminating performance of the model. A test with a high discriminating power will occupy the upper left hand portion of the graph. A less discriminating test will be close to the first diagonal of the graph. The area under the ROC curve (AUC) is a good indicator of diagnostic performance. This varies from 0.5 (non-discriminating biomarker) to 1 (completely discriminating biomarker). A value of 0.76 is indicative of a discriminating biomarker.

An ROC curve can be approximated by two principal techniques: parametric and non-parametric (Shapiro 1999). In the first case, the data are assumed to follow a specific statistical distribution (for example Gaussian) which is then adjusted to the observed data to produce a smoothed ROC curve. Non-parametric approaches consider the estimation of Se and (1-Sp) from observed data. The resulting empirical ROC curve is not a smoothed mathematical function but a step function curve.

The choice of threshold or optimal threshold, denoted δ (delta), depends on the priorities of the user in terms of sensitivity and specificity. In the case where equal weights are attributed to sensitivity and specificity, this latter can be defined as the threshold maximizing the Youden's index (J=Se+Sp−1).

Advantageously, the means of the invention can be used to obtain:
 a sensitivity [Se=TP/(TP+FN)] of at least 70% (or more), and/or
 a specificity [Sp=TN/(TN+FP)] of at least 70% (or more).

In accordance with the invention, the sensitivity may be at least 70%, at least 71%, at least 72%, at least 73%, or at least 74%, or at least 75%, or at least 76%, or at least 77%, or at least 78%, or at least 79%, or at least 80%, or at least 81%, or at least 82% (see, for example, combination Nos. 1 to 43 of Tables 5, 7 and 12 below, more particularly the sensitivity characteristics of the combinations of the levels of transcription or translation of these combinations presented in Tables 3, 8, 13, 17, 21 and 25 below).

More particularly, the sensitivity may be at least 72%, at least 73%, or at least 74%, or at least 75%, or at least 76%, or at least 77%, or at least 78%, au at least 79%, or at least 80%, or at least 81%, or at least 82% or a higher threshold (see, for example, combination Nos. 1 to 26, 30, 33 to 35 and 37 to 39 of Tables 5, 7 and 12 below, more particularly the sensitivity characteristics of combination Nos. 1 to 26, 30, 33 to 35 and 37 to 39 presented in Tables 3, 8, 13, 17, 21 and 25 below).

In one particular embodiment of the invention, the levels of expression assayed for the genes selected from said list of seventeen genes of the invention are levels of protein expression (the biological sample then advantageously being a sample of biological fluid, in particular a sample of intracorporal fluid such as blood, serum, plasma) and the sensitivity of the combination of the assayed levels of expression is at least 79%, more particularly at least 80%, more particularly at least 81%, in particular 82% or more (see, for example, combination No. 15 in Table 3 below, combination No. 9 in Table 8 below, combination No. 24 in Table 17 below, and combination No. 24 further combined with two other biological factors (in fact, GGT and/or ALP) and with a virological factor, in Table 25 below).

Alternatively or in a complementary manner, the specificity may be at least 70%, at least 71%, at least 72%, at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 92% (see, for example, combination Nos. 1 to 43 of Tables 5, 7 and 12 below, more particularly the specificity characteristics of combinations of the levels of transcription or translation of these combinations presented in Tables 3, 8, 13, 17, 21 and 25 below).

More particularly, the specificity may be at least 82%, or at least 83%, or at least 84%, or at least 85%, or at least 86%, or at least 87%, or at least 88%, or at least 89%, or at least 90%, or at least 91%, or at least 92%, or at least 92% (see for example, combination Nos. 1 to 5, 7 to 13, 16 to 22, and 27 in Table 13 below).

All combinations of these sensitivity thresholds and these specificity thresholds are explicitly included in the content of the application (see, for example, combination Nos. 1 to 43 of Tables 5, 7 and 12 below).

More particularly, all combinations comprising at least the combination of a sensitivity threshold and a specificity threshold are explicitly included in the content of the application.

Alternatively or in a complementary manner to these characteristics of sensitivity and/or specificity, the negative predictive values (NPV) reached or which might be reached by the means of the invention are particularly high.

The NPV is equal to TN/(TN+FN), with TN=true negatives and FN=false negatives, and thus represents the probability that the test subject is a responder to anti-HCV treatment, knowing that the test of the invention is negative.

In accordance with the invention, the NPV may be at least 78%, or at least 79%, or at least 80%, or at least 81%, or at least 82%, or at least 83%, or at least 84%, or at least 85%, or at least 86%, or at least 87%, or at least 88% (see, for example, combination Nos. 1 to 43 of Tables 5, 7 and 12 below, more particularly the NPV characteristics of combinations of the levels of transcription or of translation of these combinations presented in Tables 3, 8, 13, 17, 21 and 25 below).

All combinations of NPV thresholds and/or sensitivity thresholds and/or specificity thresholds are explicitly included in the content of the application.

More particularly, all combinations comprising at least the combination of a sensitivity threshold and a NPV threshold are explicitly included in the content of the application.

Alternatively or in a complementary manner to these characteristics of sensitivity and/or specificity and/or NPV, the positive predictive values (PPV) obtained or which might be obtained by the means of the invention are particularly high.

The PPV is equal to TP/(TP+FP) with TP=true positives and FP=false positives, and thus represents the probability that the test subject is a non-responder, knowing that the test of the invention is positive.

In accordance with the invention, the PPV may be at least 63%, or at least 64%, or at least 65%, or at least 66%, or at least 67%, or at least 68%, or at least 69%, or at least 70%, or at least 71%, or at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94% (see, for example, combination Nos. 1 to 43 of Tables 5, 7 and 12 below, more particularly the PPV characteristics of combinations of the levels of transcription or of translation of these combinations presented in Tables 3, 8, 13, 17, 21 and 25 below).

More particularly, the PPV may be at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94% (see for example, combination Nos. 1 to 5, 7 to 8, 10 to 14, 16 to 22, 27 and 30 in Table 13 below).

All combinations of PPV and/or NPV thresholds and/or sensitivity thresholds and/or specificity thresholds are explicitly included in the content of the application.

More particularly, all combinations comprising at least the combination of a sensitivity threshold and a PPV threshold are explicitly included in the content of the application.

More particularly, all combinations comprising at least one of said NPV thresholds and/or at least one of said sensitivity thresholds, more particularly at least one of said NPV thresholds and one of said sensitivity thresholds, more particularly at least one of said NPV thresholds and one of said sensitivity thresholds and one of said specificity thresholds are included in the application.

The predictive combinations of the invention comprise combinations of levels of gene expression selected as indicated above.

As will be indicated in more detail below, and as illustrated in the examples below (see Examples 2c) and 3b) below), it may, however, be possible to elect to involve one or more factors in these combinations other than the levels of expression of these genes, in order to combine this or these other factors and the levels of expression of the selected genes into one decision rule.

This or these other factors are preferably selected so as to construct a classification model the predictive power of which is further improved with respect to the model which does not comprise this or these other factors.

In addition to the level of expression of said selected genes, it is thus possible to assay or measure one or more other factors, such as one or more clinical factors and/or one or more virological factors and/or one or more biological factors other than the level of expression of said selected genes (see for example, Tables 21 to 24 and 25 to 28 below, which present therein examples for combination No. 24 assayed in respect of levels of transcriptions or levels of translations).

The value(s) of this (these) other factors may then be taken into account in order to construct the multivariate classification model and may thus result in still further improved classification performances, more particularly in augmented sensitivity and/or specificity and/or NPV and/or PPV characteristics.

As an example, if the values presented for combination No. 24 in Tables 13, 16 and 21, 24 below are compared, it can be seen that the values for AUC, Se and NPV increase when the combination of the levels of transcription of said selected genes are also combined with other factors, in particular at least one biological factor and at least one virological factor (in fact, ALP and VLbeforeTTT).

Similarly, if the values presented for combination No. 24 in Tables 17, 20 and 25, 28 below are compared, it can be seen that several of the values for AUC, Spe and PPV increase when the combination of the levels of translation of said selected genes are also combined with other factors, in particular at least two other biological factors and at least one virological factor (in fact, GGT, ALP and VLbeforeTTT).

Advantageously, when one or more other factors are combined with a combination of genes selected from said list of seventeen genes of the invention, at least one of the AUC characteristics (if appropriate, the LOOCV error), sensitivity, specificity, NPV and PPV, is improved thereby.

As indicated above, and as illustrated below, the means of the invention involve measuring the level of expression of:
  at least one gene from among MBL2, LGALS3BP and IL8, and
  at least one gene from among G1P2, CCL21 and CXCL10, and
  optionally, at least one gene from among AFP, CRP, CXCL11, CXCL6, CXCL9, FGF7, MDK, MMP2, SFN, TGFB2 and VEGFD.

Advantageously, the total number of the genes selected thereby is 2, 3, 4 or 5.

The choice of genes is made as a function of the demands or wishes for the performance to be obtained, for example as a function of the sensitivity and/or specificity and/or NPV and/or PPV which is to be obtained or anticipated. Clearly, the lower the number of selected genes, the simpler the means of the invention are to implement.

All possible choices of genes are explicitly included in the application.

In a manner similar to that indicated above for the sensitivity thresholds, the specificity thresholds, the NPV thresholds, the PPV thresholds and the total number of selected genes, all combinations of genes selected from each of the lists of genes and/or the total numbers of genes selected and/or sensitivity thresholds and/or specificity thresholds and/or NPV thresholds and/or PPV thresholds are explicitly included in the content of the application.

Forty-three Examples of combinations of genes in accordance with the invention are presented in Tables 2, 7 and 12 below.

As an example, said genes selected from said list of seventeen genes of the invention are:
  LGALS3BP and CXCL10 (combination No. 15); or
  LGALS3BP, CXCL10 and MDK (combination No. 9); or
  LGALS3BP, IL8, CXCL10, CCL21 and MDK (combination No. 24); or
  CRP, G1P2, LGALS3BP, MBL2 and TGFB2 (combination No. 1); or
  AFP, CXCL6, CXCL9, G1P2 and MBL2 (combination No. 2); or
  AFP, FGF7, G1P2, MBL2 and MMP2 (combination No. 3); or
  CXCL11, G1P2, IL8, MBL2 and TGFB2 (combination No. 4); or
  G1P2, IL8, MBL2, SFN and TGFB2 (combination No. 5); or
  CCL21, FGF7, IL8, LGALS3BP and MBL2 (combination No. 6); or
  G1P2, LGALS3BP, MBL2, MDK and TGFB2 (combination No. 7); or
  G1P2, LGALS3BP, MBL2, MMP2 and TGFB2 (combination No. 8); or
  G1P2, LGALS3BP, MBL2, SFN and TGFB2 (combination No. 10); or
  CXCL6, CXCL10, G1P2, MBL2 and MMP2 (combination No. 11); or
  CXCL6, CXCL11, G1P2, MBL2 and MMP2 (combination No. 12); or FGF7, G1P2, LGALS3BP, MBL2 and TGFB2 (combination No. 13); or AFP, CXCL6, G1P2, IL8 and MDK (combination No. 14); or CCL21, G1P2, LGALS3BP, MBL2 and SFN (combination No. 16); or CXCL10, G1P2, LGALS3BP, MBL2 and TGFB2 (combination No. 17); or CRP, CXCL6, G1P2, MBL2 and SFN (combination No. 18); or CXCL10, CXCL11, G1P2, MBL2 and MMP2 (combination No. 19); or CXCL11, G1P2, LGALS3BP, MBL2 and MDK (combination No. 20); or G1P2, IL8, LGALS3BP, MBL2 and TGFB2 (combination No. 21); or FGF7, G1P2, IL8, MDK and SFN (combination No. 22); or CCL21, FGF7, LGALS3BP, MBL2 and MDK (combination No. 23); or CCL21, CXCL6, IL8, LGALS3BP and MDK (combination No. 25); or CCL21, FGF7, MBL2, MDK and VEGFD (combination No. 26); or CXCL6, IL8, CCL21, GIP2 and MDK (combination No. 30); or CXCL6, IL8, CXCL10, GIP2 and MDK (combination No. 33); or CCL21, CXCL10, GIP2, LGALS3BP and MDK (combination No. 34); or CXCL6, IL8, CCL21, GIP2 and LGALS3BP (combination No. 35); or IL8, CCL21, CXCL10, GIP2 and LGALS3BP (combination No. 37); or IL8, CXCL10, GIP2, LGALS3BP and MDK (combination No. 38); or CXCL6, IL8, GIP2, LGALS3BP and MDK (combination No. 39); or FGF7, G1P2, LGALS3BP, MBL2 and MDK (combination No. 27); or CXCL10, FGF7, IL8, MDK and VEGFD (combination No. 28); or CCL21, CXCL6, CXCL10, LGALS3BP and MDK (combination No. 29); or IL8, CCL21, GIP2, LGALS3BP and MDK (combination No. 31); or IL8, CCL21, CXCL10, GIP2 and MDK (combination No. 32); or CXCL6, IL8, CXCL10, GIP2 and LGALS3BP (combination No. 36); or CXCL6, IL8, CCL21, CXCL10 and GIP2 (combination No. 40); or CXCL6, CXCL10, GIP2, LGALS3BP and MDK (combination No. 41); or CXCL6, IL8, CCL21, CXCL10 and LGALS3BP (combination No. 42); or CXCL6, CCL21, CXCL10, GIP2 and LGALS3BP (combination No. 43).

In accordance with one aspect of the invention, said genes selected in step i) are not:

FGF7, G1P2, LGALS3BP, MBL2 and MDK (combination No. 27);

CXCL10, FGF7, IL8, MDK and VEGFD (combination No. 28);

CCL21, CXCL6, CXCL10, LGALS3BP and MDK (combination No. 29);

IL8, CCL21, GIP2, LGALS3BP and MDK (combination No. 31);

IL8, CCL21, CXCL10, GIP2 and MDK (combination No. 32);

CXCL6, IL8, CXCL10, GIP2 and LGALS3BP (combination No. 36);

CXCL6, IL8, CCL21, CXCL10 and GIP2 (combination No. 40);

CXCL6, CXCL10, GIP2, LGALS3BP and MDK (combination No. 41);

CXCL6, IL8, CCL21, CXCL10 and LGALS3BP (combination No. 42);

CXCL6, CCL21, CXCL10, GIP2 and LGALS3BP (combination No. 43).

In accordance with one aspect of the invention, said genes selected in step i) are:

LGALS3BP and CXCL10 (combination No. 15); or

LGALS3BP, CXCL10 and MDK (combination No. 9); or

LGALS3BP, IL8, CXCL10, CCL21 and MDK (combination No. 24); or

CRP, G1P2, LGALS3BP, MBL2 and TGFB2 (combination No. 1); or

AFP, CXCL6, CXCL9, G1P2 and MBL2 (combination No. 2); or

AFP, FGF7, G1P2, MBL2 and MMP2 (combination No. 3); or

CXCL11, G1P2, IL8, MBL2 and TGFB2 (combination No. 4); or

G1P2, IL8, MBL2, SFN and TGFB2 (combination No. 5); or

CCL21, FGF7, IL8, LGALS3BP and MBL2 (combination No. 6); or

G1P2, LGALS3BP, MBL2, MDK and TGFB2 (combination No. 7); or

G1P2, LGALS3BP, MBL2, MMP2 and TGFB2 (combination No. 8); or

G1P2, LGALS3BP, MBL2, SFN and TGFB2 (combination No. 10); or

CXCL6, CXCL10, G1P2, MBL2 and MMP2 (combination No. 11); or

CXCL6, CXCL11, G1P2, MBL2 and MMP2 (combination No. 12); or

FGF7, G1P2, LGALS3BP, MBL2 and TGFB2 (combination No. 13); or

AFP, CXCL6, G1P2, IL8 and MDK (combination No. 14); or

CCL21, G1P2, LGALS3BP, MBL2 and SFN (combination No. 16); or

CXCL10, G1P2, LGALS3BP, MBL2 and TGFB2 (combination No. 17); or

CRP, CXCL6, G1P2, MBL2 and SFN (combination No. 18); or

CXCL10, CXCL11, G1P2, MBL2 and MMP2 (combination No. 19); or

CXCL11, G1P2, LGALS3BP, MBL2 and MDK (combination No. 20); or

G1P2, IL8, LGALS3BP, MBL2 and TGFB2 (combination No. 21); or

FGF7, G1P2, IL8, MDK and SFN (combination No. 22); or

CCL21, FGF7, LGALS3BP, MBL2 and MDK (combination No. 23); or

CCL21, CXCL6, IL8, LGALS3BP and MDK (combination No. 25); or

CCL21, FGF7, MBL2, MDK and VEGFD (combination No. 26); or

CXCL6, IL8, CCL21, GIP2 and MDK (combination No. 30); or

CXCL6, IL8, CXCL10, GIP2 and MDK (combination No. 33); or

CCL21, CXCL10, GIP2, LGALS3BP and MDK (combination No. 34); or

CXCL6, IL8, CCL21, GIP2 and LGALS3BP (combination No. 35); or

IL8, CCL21, CXCL10, GIP2 and LGALS3BP (combination No. 37); or

IL8, CXCL10, GIP2, LGALS3BP and MDK (combination No. 38); or

CXCL6, IL8, GIP2, LGALS3BP and MDK (combination No. 39).

Examples of multivariate classification models were constructed for each of these combinations of genes. Tables 2 to 28 below present the Examples.

Tables 2 to 6 (combination No. 15) illustrate the performances of the combination of the levels of expression of two genes (in fact, seric concentrations of two proteins).

Tables 7 to 11 (combination No. 9) illustrate the performances of the combination of the levels of expression of three genes (in fact, seric concentrations of three proteins).

Tables 12 to 16 (combination Nos. 1 to 8, 10 to 14, and 16 to 43) illustrate the performances of the combination of the levels of transcription of five genes (in fact, the value of Ct which was measured for the RNA transcripts of this gene and which has been normalized using the $2^{-\Delta Ct}$ method).

Tables 17 to 20 (combination No. 24) illustrate the performances of the combination of the levels of translation of five genes (in fact, seric concentrations of five proteins).

TABLE 2

Example of combination of the levels of expression of two genes

| No. of combination | Selected genes | |
|---|---|---|
| 15 | CXCL10 | LGALS3BP |

TABLE 3

Values for sensitivity (Se), specificity (Spe), negative predictive value (NPV), positive predictive value (PPV) and LOOCV error which may be associated with the combinations of the levels of translation (more particularly the levels of translation into seric proteins) of selected genes in accordance with the invention

| No. of combination (see Table 2) | Classification model used | Se | Spe | NPV | PPV | LOOCV error |
|---|---|---|---|---|---|---|
| 15 | mROC (*) | 82 | 72 | 82 | 72 | ND |

(*) the values for Se, Spe, NPV, PPV and LOOCV error indicated are those for the corresponding mROC function of Table 4 below
LOOCV error = Leave-One-Out Cross Validation;
ND = not determined

TABLE 4

Examples of mROC models (Z function) combining the levels of protein translation (more particularly into seric proteins) of selected genes in accordance with the invention, and Example of PT threshold for these functions (in fact, threshold maximizing Youden's index δ)

| No. of combination (see Table 2 above) | Z function combining the levels of translation (seric proteins) of the selected genes | Name of function | PT threshold (δ threshold) |
|---|---|---|---|
| 15 | Z = 0.030 × CXCL10$^t$ + 0.447 × LGALS3BP$^t$ | Z15PROT | 2.169 |

TABLE 5 measurList of genes for which it is advised to normalize the assayed measurement values (in particular, the measurement values for the levels of protein translation, more particularly when these proteins are seric proteins), for example by a Box-Cox normalisation, and example of values for the Box-Cox parameter (λ) which can be used in the Z functions indicated in Table 4 above.

| Genes for which it is advised to normalize the value for the level of translation (protein) | Example of values for the Box-Cox parameter (λ) which can be used for the Z functions of Table 4 above (*) |
|---|---|
| CXCL10 | 0.41 |
| LGALS3BP | 0.33 |

(*): lambda, the parameter for Box-Cox transformations [BMK$^t$ = (BMK$^\lambda$ − 1)/λ]

TABLE 6

AUC of Z functions of Table 4

| No. of combination (see Table 2 above) | Name of function (see Table 4 above) | AUC | AUC, lower limit | AUC, upper limit |
|---|---|---|---|---|
| 15 | Z15PROT | 0.831 | 0.760 | 0.885 |

TABLE 7

Example of combination of the levels of expression of three genes

| No. of combination | Selected genes | | |
|---|---|---|---|
| 9 | LGALS3BP | CXCL10 | MDK |

TABLE 8

Values for sensitivity (Se), specificity (Spe), negative predictive value (NPV), positive predictive value (PPV) and LOOCV error which may be associated with the combinations of the levels of translation (more particularly the levels of translation into seric proteins) of selected genes in accordance with the invention

| No. of combination (see Table 7) | Classification model used | Se | Spe | NPV | PPV | LOOCV error |
|---|---|---|---|---|---|---|
| 9 | mROC (*) | 82 | 74 | 83 | 73 | ND |

(*) the values for Se, Spe, NPV, PPV and LOOCV error indicated are those for the corresponding mROC function of Table 9 below
LOOCV error = Leave-One-Out Cross Validation;
ND = not determined

TABLE 9

Examples of mROC models (Z function) combining the levels of protein translation (more particularly into seric proteins) of selected genes in accordance with the invention, and Example of PT threshold for these functions (in fact, threshold maximizing Youden's index $\delta$)

| No. of combination (see Table 7 above) | Z function combining the levels of translation (seric proteins) of the selected genes | Name of function | PT threshold ($\delta$ threshold) |
|---|---|---|---|
| 9 | $Z = 0.029 \times CXCL10^t + 0.472 \times LGALS3BP^t - 0.319 \times MDK$ | Z9PROT | 2.164 |

TABLE 10

List of genes for which it is advised to normalize the assayed measurement values (in particular, the measurement values for the levels of protein translation, more particularly when these proteins are seric proteins), for example by a Box-Cox normalisation, and example of values for the Box-Cox parameter ($\lambda$) which can be used in the Z functions indicated in Table 9 above.

| Genes for which it is advised to normalize the value for the level of translation (protein) | Example of values for the Box-Cox parameter ($\lambda$) which can be used for the Z functions of Table 9 above (*) |
|---|---|
| CXCL10 | 0.41 |
| LGALS3BP | 0.33 |

(*): lambda, the parameter for Box-Cox transformations [$BMK^t = (BMK^\lambda - 1)/\lambda$]

TABLE 11

AUC of Z functions of Table 9

| No. of combination (see Table 7 above) | Name of function (see Table 9 above) | AUC | AUC, lower limit | AUC, upper limit |
|---|---|---|---|---|
| 9 | Z9PROT | 0.836 | 0.766 | 0.888 |

TABLE 12

Examples of combinations of levels of expression of five genes

| No. of combination | Selected genes | | | | |
|---|---|---|---|---|---|
| 1 | CRP | G1P2 | LGALS3BP | MBL2 | TGFB2 |
| 2 | AFP | CXCL6 | CXCL9 | G1P2 | MBL2 |
| 3 | AFP | FGF7 | G1P2 | MBL2 | MMP2 |
| 4 | CXCL11 | G1P2 | IL8 | MBL2 | TGFB2 |
| 5 | G1P2 | IL8 | MBL2 | SFN | TGFB2 |
| 6 | CCL21 | FGF7 | IL8 | LGALS3BP | MBL2 |
| 7 | G1P2 | LGALS3BP | MBL2 | MDK | TGFB2 |
| 8 | G1P2 | LGALS3BP | MBL2 | MMP2 | TGFB2 |
| 10 | G1P2 | LGALS3BP | MBL2 | SFN | TGFB2 |
| 11 | CXCL6 | CXCL10 | G1P2 | MBL2 | MMP2 |
| 12 | CXCL6 | CXCL11 | G1P2 | MBL2 | MMP2 |
| 13 | FGF7 | G1P2 | LGALS3BP | MBL2 | TGFB2 |
| 14 | AFP | CXCL6 | G1P2 | IL8 | MDK |
| 16 | CCL21 | G1P2 | LGALS3BP | MBL2 | SFN |
| 17 | CXCL10 | G1P2 | LGALS3BP | MBL2 | TGFB2 |
| 18 | CRP | CXCL6 | G1P2 | MBL2 | SFN |
| 19 | CXCL10 | CXCL11 | G1P2 | MBL2 | MMP2 |
| 20 | CXCL11 | G1P2 | LGALS3BP | MBL2 | MDK |
| 21 | G1P2 | IL8 | LGALS3BP | MBL2 | TGFB2 |
| 22 | FGF7 | G1P2 | IL8 | MDK | SFN |
| 23 | CCL21 | FGF7 | LGALS3BP | MBL2 | MDK |
| 24 | CCL21 | CXCL10 | IL8 | LGALS3BP | MDK |
| 25 | CCL21 | CXCL6 | IL8 | LGALS3BP | MDK |
| 26 | CCL21 | FGF7 | MBL2 | MDK | VEGFD |
| 27 | FGF7 | G1P2 | LGALS3BP | MBL2 | MDK |
| 28 | CXCL10 | FGF7 | IL8 | MDK | VEGFD |
| 29 | CCL21 | CXCL6 | CXCL10 | LGALS3BP | MDK |
| 30 | CXCL6 | IL8 | CCL21 | GIP2 | MDK |
| 31 | IL8 | CCL21 | GIP2 | LGALS3BP | MDK |
| 32 | IL8 | CCL21 | CXCL10 | GIP2 | MDK |
| 33 | CXCL6 | IL8 | CXCL10 | GIP2 | MDK |
| 34 | CCL21 | CXCL10 | GIP2 | LGALS3BP | MDK |
| 35 | CXCL6 | IL8 | CCL21 | GIP2 | LGALS3BP |
| 36 | CXCL6 | IL8 | CXCL10 | GIP2 | LGALS3BP |
| 37 | IL8 | CCL21 | CXCL10 | GIP2 | LGALS3BP |
| 38 | IL8 | CXCL10 | GIP2 | LGALS3BP | MDK |
| 39 | CXCL6 | IL8 | GIP2 | LGALS3BP | MDK |

TABLE 12-continued

Examples of combinations of levels of expression of five genes

| No. of combination | Selected genes | | | | |
|---|---|---|---|---|---|
| 40 | CXCL6 | IL8 | CCL21 | CXCL10 | GIP2 |
| 41 | CXCL6 | CXCL10 | GIP2 | LGALS3BP | MDK |
| 42 | CXCL6 | IL8 | CCL21 | CXCL10 | LGALS3BP |
| 43 | CXCL6 | CCL21 | CXCL10 | GIP2 | LGALS3BP |

TABLE 13

Values for sensitivity (Se), specificity (Spe), negative predictive value (NPV), positive predictive value (PPV) and LOOCV error which may be associated with the combinations of the levels of transcription of five selected genes in accordance with the invention (RNA transcripts, more particularly RNA from a tissue sample or hepatic cells)

| No. of combination (see Table 12) | Classification model used | Se | Spe | NPV | PPV | LOOCV error |
|---|---|---|---|---|---|---|
| 1 | WKNN | 82 | 92 | 88 | 88 | 12 |
| 2 | RF | 80 | 92 | 87 | 88 | 13 |
| 3 | RF | 80 | 84 | 85 | 78 | 18 |
| 4 | RF | 80 | 84 | 85 | 78 | 18 |
| 5 | RF | 80 | 84 | 85 | 78 | 18 |
| 6 | mROC (*) | 80 | 70 | 83 | 65 | ND |
| 7 | WKNN | 77 | 90 | 85 | 85 | 15 |
| 8 | WKNN | 77 | 90 | 85 | 85 | 15 |
| 10 | WKNN | 75 | 89 | 80 | 94 | 16 |
| 11 | WKNN | 75 | 84 | 84 | 82 | 17 |
| 12 | WKNN | 75 | 84 | 81 | 88 | 17 |
| 13 | WKNN | 75 | 83 | 82 | 86 | 17 |
| 14 | WKNN | 75 | 71 | 81 | 86 | 18 |
| 16 | WKNN | 73 | 92 | 79 | 90 | 18 |
| 17 | WKNN | 73 | 89 | 82 | 82 | 18 |
| 18 | WKNN | 73 | 87 | 80 | 88 | 18 |
| 19 | WKNN | 73 | 86 | 85 | 78 | 18 |
| 20 | WKNN | 73 | 86 | 78 | 93 | 18 |
| 21 | WKNN | 73 | 83 | 80 | 88 | 18 |
| 22 | WKNN | 73 | 83 | 79 | 90 | 18 |
| 23 | mROC (*) | 73 | 75 | 80 | 66 | ND |
| 24 | mROC (*) | 73 | 74 | 80 | 66 | ND |
| 25 | mROC (*) | 73 | 73 | 79 | 65 | ND |
| 26 | mROC (*) | 73 | 70 | 79 | 63 | ND |
| 27 | WKNN | 70 | 90 | 81 | 84 | 18 |
| 28 | mROC (*) | 70 | 78 | 79 | 69 | ND |
| 29 | mROC (*) | 70 | 74 | 78 | 65 | ND |
| 30 | mROC (*) | 73 | 73 | 79 | 79 | ND |
| 31 | mROC (*) | 71 | 76 | 80 | 65 | ND |
| 32 | mROC (*) | 71 | 76 | 79 | 67 | ND |
| 33 | mROC (*) | 73 | 73 | 79 | 65 | ND |
| 34 | mROC (*) | 73 | 73 | 79 | 65 | ND |
| 35 | mROC (*) | 73 | 73 | 79 | 65 | ND |
| 36 | mROC (*) | 71 | 75 | 78 | 66 | ND |
| 37 | mROC (*) | 73 | 76 | 80 | 68 | ND |
| 38 | mROC (*) | 73 | 73 | 79 | 65 | ND |
| 39 | mROC (*) | 73 | 73 | 79 | 64 | ND |
| 40 | mROC (*) | 71 | 75 | 78 | 66 | ND |
| 41 | mROC (*) | 71 | 75 | 78 | 66 | ND |
| 42 | mROC (*) | 71 | 73 | 78 | 65 | ND |
| 43 | mROC (*) | 71 | 73 | 78 | 65 | ND |

(*) the values for Se, Spe, NPV, PPV and LOOCV error indicated are those for the corresponding mROC function of Table 14 below
LOOCV error = Leave-One-Out Cross Validation (Hastie, Tibishirani and Friedman, 2009);
ND = not determined

TABLE 14

Examples of mROC models (Z function) combining the levels of transcription of five selected genes (RNA transcripts, more particularly RNA from a tissue sample or hepatic cells), and Example of PT threshold for these functions (in fact, threshold maximizing Youden's index δ)

| No. of combination (see Table 12 above) | Z function combining the levels of transcription (RNA) of the selected genes | Name of function | PT threshold (δ threshold) |
|---|---|---|---|
| 6 | $Z = 0.428 \times CCL21^r + 0.543 \times FGF7 + 0.029 \times IL8 + 0.281 \times LGALS3BP^r + 0.108 \times (-MBL2)$ | Z6ARN | −2.884 |
| 23 | $Z = 0.417 \times CCL21^r + 0.55 \times FGF7 + 0.198 \times LGALS3BP^r + 0.099 \times (-MBL2) + 0.147 \times MDK^r$ | Z23ARN | −2.842 |
| 24 | $Z = 0.359 \times CCL21^r + 0.028 \times CXCL10^r + 0.055 \times IL8 + 0.107 \times LGALS3BP^r + 0.22 \times MDK^r$ | Z24ARN | −2.309 |
| 25 | $Z = 0.374 \times (CCL21^r) - 0.105 \times CXCL6 + 0.068 \times IL8 + 0.11 \times LGALS3BP^r + 0.225 \times MDK^r$ | Z25ARN | −2.331 |
| 26 | $Z = 0.516 \times CCL21^r + 0.554 \times FGF7 + 0.07 \times (-MBL2) + 0.276 \times MDK^r - 0.092 \times VEGFD$ | Z26ARN | −2.868 |
| 28 | $Z = 0.321 \times CXCL10^r + 0.623 \times FGF7 - 0.018 \times IL8 + 0.352 \times MDK^r - 0.067 \times VEGFD$ | Z28ARN | −1.363 |
| 29 | $Z = 0.356 \times CCL21^r + 0.116 \times CXCL6 + 0.072 \times CXCL10^r + 0.087 \times LGALS3BP^r + 0.244 \times MDK^r$ | Z29ARN | −2.417 |
| 30 | $Z = 0.283 * CCL21^r - 0.108 * CXCL6 + 0.162 * GIP2^r + 0.077 * IL8 + 0.195 * MDK^r$ | Z30ARN | −1.504 |
| 31 | $Z = 0.266 * CCL21^r + 0.155 * GIP2^r + 0.068 * IL8 + 0.050 * LGALS3BP^r + 0.160 * MDK^r$ | Z31ARN | −1.509 |
| 32 | $Z = 0.304 * CCL21^r - 0.034 * CXCL10^r + 0.168 * GIP2^r + 0.069 * IL8 + 0.186 * MDK^r$ | Z32ARN | −1.473 |
| 33 | $Z = -0.125 * CXCL6 + 0.074 * CXCL10^r + 0.198 * GIP2^r + 0.080 * IL8 + 0.241 * MDK^r$ | Z33ARN | −0.554 |
| 34 | $Z = 0.290 * CCL21^r + 0.035 * CXCL10^r + 0.137 * GIP2^r + 0.029 * LGALS3BP^r + 0.214 * MDK^r$ | Z34ARN | −1.782 |

TABLE 14-continued

Examples of mROC models (Z function) combining the levels of transcription of five selected genes (RNA transcripts, more particularly RNA from a tissue sample or hepatic cells), and Example of PT threshold for these functions (in fact, threshold maximizing Youden's index δ)

| No. of combination (see Table 12 above) | Z function combining the levels of transcription (RNA) of the selected genes | Name of function | PT threshold (δ threshold) |
|---|---|---|---|
| 35 | Z = 0.276 * CCL21$^t$ − 0.039 * CXCL6 + 0.175 * GIP2$^t$ + 0.085 * IL8 + 0.126 * LGALS3BP$^t$ | Z35ARN | −1.405 |
| 36 | Z = −0.047 * CXCL6 + 0.026 * CXCL10$^t$ + 0.211 * GIP2$^t$ + 0.095 * IL8 + 0.181 * LGALS3BP$^t$ | Z36ARN | −0.407 |
| 37 | Z = 0.311 * CCL21$^t$ − 0.072 * CXCL10$^t$ + 0.182 * GIP2$^t$ + 0.087 * IL8 + 0.129 * LGALS3BP$^t$ | Z37ARN | −1.386 |
| 38 | Z = 0.050 * CXCL10$^t$ + 0.183 * GIP2$^t$ + 0.073 * IL8 + 0.091 * LGALS3BP$^t$ + 0.177 * MDK$^t$ | Z38ARN | −0.642 |
| 39 | Z = −0.119 * CXCL6 + 0.193 * GIP2$^t$ + 0.091 * IL8 + 0.1 * LGALS3BP$^t$ + 0.179 * MDK$^t$ | Z39ARN | −0.576 |
| 40 | Z = 0.379 * CCL21$^t$ − 0.019 * CXCL6 − 0.059 * CXCL10$^t$ + 0.222 * GIP2$^t$ + 0.09 * IL8 | Z40ARN | −1.282 |
| 41 | Z = 0.162 * CXCL6 + 0.114 * CXCL10$^t$ + 0.166 * GIP2$^t$ + 0.073 * LGALS3BP$^t$ + 0.214 * MDK$^t$ | Z41ARN | −0.802 |
| 42 | Z = 0.409 * CCL21$^t$ − 0.014 * CXCL6 + 0.0004 * CXCL10$^t$ + 0.076 * IL8 + 0.231 * LGALS3BP$^t$ | Z42ARN | −2.33 |
| 43 | Z = 0.322 * CCL21$^t$ + 0.278 * CXCL6 − 0.007 * CXCL10$^t$ + 0.167 * GIP2$^t$ + 0.125 * LGALS3BP$^t$ | Z43ARN | −1.62 |

TABLE 15 measurList of genes for which it is advised to normalize the assayed measurement values (in particular, the measurement values for the levels of RNA transcription, more particularly when these RNAs originate from a tissue sample or hepatic cells), for example by a Box-Cox normalisation, and example of values for the Box-Cox parameter (λ) which can be used in the Z functions indicated in Table 14 above.

| Genes for which it is advised to normalize the value for the level of transcription (RNA) | Example of value of Box-Cox parameter (λ) which can be used for the Z functions of Table 14 above |
|---|---|
| CCL21 | 0.02 |
| MDK | 0.12 |
| LGALS3BP | −0.06 |
| CXCL10 | 0.18 |
| G1P2 | 0.07 |

TABLE 16

AUC of Z functions of Table 14

| No. of combination (see Table 12 above) | Name of function (see Table 14 above) | AUC | AUC, lower limit | AUC, upper limit |
|---|---|---|---|---|
| 6 | Z6ARN | 0.805 | 0.709 | 0.875 |
| 23 | Z23ARN | 0.801 | 0.704 | 0.872 |
| 24 | Z24ARN | 0.771 | 0.665 | 0.851 |
| 25 | Z25ARN | 0.771 | 0.665 | 0.851 |
| 26 | Z26ARN | 0.794 | 0.696 | 0.867 |
| 28 | Z28ARN | 0.795 | 0.693 | 0.869 |
| 29 | Z29ARN | 0.767 | 0.629 | 0.834 |
| 30 | Z30ARN | 0.784 | 0.667 | 862 |
| 31 | Z31ARN | 0.783 | 0.676 | 0.861 |
| 32 | Z32ARN | 0.782 | 0.676 | 0.861 |
| 33 | Z33ARN | 0.78 | 0.674 | 0.859 |
| 34 | Z34ARN | 0.779 | 0.671 | 0.859 |
| 35 | Z35ARN | 0.778 | 0.672 | 0.857 |
| 36 | Z36ARN | 0.778 | 0.673 | 0.857 |
| 37 | Z37ARN | 0.778 | 0.672 | 0.857 |
| 38 | Z38ARN | 0.778 | 0.67 | 0.858 |
| 39 | Z39ARN | 0.777 | 0.669 | 0.857 |
| 40 | Z40ARN | 0.775 | 0.671 | 0.854 |
| 41 | Z41ARN | 0.773 | 0.664 | 0.855 |
| 42 | Z42ARN | 0.768 | 0.662 | 0.848 |
| 43 | Z43ARN | 0.765 | 0.654 | 0.848 |

TABLE 17

Values for sensitivity (Se), specificity (Spe), negative predictive value (NPV), positive predictive value (PPV) and LOOCV error which may be associated with combinations of the levels of translation (more particularly the levels of translation into seric proteins) of five selected genes in accordance with the invention

| No. of combination (see Table 12) | Classification model used | Se | Spe | NPV | PPV | LOOCV error |
|---|---|---|---|---|---|---|
| 24 | mROC (*) | 82 | 74 | 83 | 73 | ND |

(*) the values for Se, Spe, NPV, PPV and LOOCV error indicated are those for the corresponding mROC function of Table 18 below
LOOCV error = Leave-One-Out Cross Validation

TABLE 18

Examples of models of mROC models (Z function) combining the levels of protein translation (more particularly into seric proteins) of five selected genes in accordance with the invention, and Example of PT threshold for these functions (in fact, threshold maximizing Youden's index δ)

| No. of combination (see Table 12 above) | Z function combining the levels of translation (seric proteins) of the selected genes | Name of function | PT threshold (δ threshold) |
|---|---|---|---|
| 24 | Z = 0.025 × CXCL10$^t$ + 0.071 × IL8$^t$ + 0.465 × LGALS3BP$^t$ − 0.341 × MDK − 0.001 × CCL21$^t$ | Z24PROT | 2.231 |

TABLE 19 measurList of genes for which it is advised to normalize the assayed measurement values (in particular, the measurement values for the levels of protein translation, more particularly when these proteins are seric proteins), for example by a Box-Cox normalisation, and example of values for the Box-Cox parameter (λ) which can be used in the Z functions indicated in Table 18 above.

| Genes for which it is advised to normalize the value for the level of translation (protein) | Example of values for the Box-Cox parameter (λ) which can be used for the Z functions of Table 18 above (*) |
|---|---|
| IL8 | 0.23 |
| LGALS3BP | 0.33 |
| CXCL10 | 0.41 |
| CCL21 | −0.01 |

TABLE 19-continued measurList of genes for which it is advised to normalize the assayed measurement values (in particular, the measurement values for the levels of protein translation, more particularly when these proteins are seric proteins), for example by a Box-Cox normalisation, and example of values for the Box-Cox parameter (λ) which can be used in the Z functions indicated in Table 18 above.

| Genes for which it is advised to normalize the value for the level of translation (protein) | Example of values for the Box-Cox parameter (λ) which can be used for the Z functions of Table 18 above (*) |
|---|---|

(*): lambda, the parameter for Box-Cox transformations[$BMK^t = (BMK^\lambda - 1)/\lambda$]

TABLE 20

AUC of Z functions of Table 18

| No. of combination (see Table 12 above) | Name of function (see Table 18 above) | AUC | AUC, lower limit | AUC, upper limit |
|---|---|---|---|---|
| 24 | Z24PROT | 0.838 | 0.769 | 0.890 |

In addition to the levels of expression of said genes selected from the list of seventeen genes of the invention, the means of the invention can also comprise a combination of one or more other factors, such as:

one or more clinical factors, such as:
  sex (female, F or male, M),
  age at the date of sampling (Age), for example, age at the date of HBP, age at the date of hepatic cytopuncture, age at the date of sampling blood, serum, plasma or urine,
  age of patient at the date of contamination,
  age of patient at the start of treatment,
  body mass index (BMI),
  insulin sensitivity index (HOMA),
  diabetes,
  alcohol consumption,
  degree of steatosis,
  mode of contamination,
  Metavir activity,
  hepatic fibrosis score measured using the Metavir system (Metavir F score) or using the Ishak system;
and/or
  one or more virological factors, such as:
    viral genotype, more particularly genotype of the HCV or HCVs,
    duration of infection,
    viral load before treatment, more particularly HCV load before treatment (VLbeforeTTT),
    viral load, more particularly HCV load, measured for the patient at the date of start of treatment (viral load at D0),
    viral load, more particularly HCV load, measured for the patient at the date of sampling (viral load at HBP, viral load at the date of hepatic cytopuncture, viral load at the date of sampling blood, serum, plasma or urine);
and/or
  one or more biological factors other than the levels of expression of said selected genes, which may in particular be selected from the concentrations, contents or quantities of intracorporal proteins, concentrations, contents or quantities of intracorporal metabolites, concentrations, contents or quantities of elements occurring in blood, and assays representative of the quantity of circulating iron, such as:
    concentration of haptoglobin (Hapto),
    concentration of apolipoprotein A1 (ApoA1),
    total quantity of bilirubin (BLT),
    concentration of gamma glutamyl transpeptidase (GGT),
    concentration of aspartate aminotransferase (AST),
    concentration of alanine aminotransferase (ALT),
    platelet count (PLQ),
    quantity of prothrombin (TP),
    quantity of HDL cholesterol (Chol-HDL),
    total quantity of cholesterol,
    concentration of ferritin (Ferritin),
    level of glycaemia (glycaemia),
    concentration of peptide C,
    quantity of insulin (insulinaemia),
    concentration of triglycerides (TG),
    quantity of albumin,
    transferrin saturation (TSAT),
    concentration of alkaline phosphatase (ALP).

Tables 21 to 24 (combination No. 24) illustrate the performances of the combination of the levels of transcription of genes (in fact, the Ct value which was measured for the RNA transcripts of this gene and which was normalized by the $2^{-\Delta Ct}$ method), also combined with one or more other biological, virological or clinical factors (in fact, VLbeforeTTT and ALP).

Tables 25 to 28 (combination No. 24) illustrate the performances of the combination of the levels of translation of genes (in fact, seric concentrations of two to five proteins), also combined with other biological, virological or clinical factors (in fact, VLbeforeTTT, GGT and ALP; or Age, VLbeforeTTT and ALT; or Age, VLbeforeTTT and GGT; or VLbeforeTTT, AST and ALP; or BMI).

This or these other factors may be assayed for a sample with a nature which differs from that used to assay the levels of expression of said selected genes. As an example, the biological sample for assaying the levels of expression of said genes selected from said list of seventeen genes of the invention may be a HBP or hepatic cytopuncture sample, and the biological sample for assaying the values of said other factors may be a sample of a biological fluid such as blood, plasma or serum or urine. Similarly, the nature of the assayed level of expression measure may be different; as an example, to assay the level of expression of said selected genes, it is possible to assay the levels of their transcription into RNA, while for those of said other factors which are biological factors, the assayed level of expression will generally be a protein concentration.

The measurement or assay of certain of these factors may sometimes be considered to be measuring the level of translation (measurement of protein concentration) of a gene other than a selected gene of the invention (for example GGT and/or ALP and/or ALT and/or AST; see Tables 21 to 24 and 25 to 28 below; see Examples 2c) and 3b) below).

The number of genes the level of expression of which is measured, and which are not genes selected from said list of seventeen genes of the invention (for example GGT and/or ALP and/or ALT and/or AST) is preferably a maximum of 18, more particularly 14 or fewer, more particularly 11 or fewer, more particularly 6 or fewer, more particularly 4 or 3 or 2 or 1 or 0, more particularly 3 or 2 or 1 or 0, in particular 2 or 1 or 0.

Advantageously, this or these other factors are or comprise one or more biological factors, in particular one or more factors from the following biological factors:

concentration of alkaline phosphatase (ALP), and/or
concentration of gamma glutamyl transpeptidase (GGT), more particularly at least ALP,
concentration of alanine aminotransferase (ALT) and/or
concentration of aspartate aminotransferase (AST).

Examples 2c), 3b) and 6a) to 6c) above provide an illustration of such combinations.

Alternatively or in a complementary manner, this or these factors may more particularly be or comprise one or more factors from the following virological factors:

viral load before treatment (VLbeforeTTT); and/or
genotype of the HCV or HCVs.

Examples 2c), 3b) and 6a) to 6c) below provide an illustration of such combinations.

Alternatively or in a complementary manner, this or these factors may more particularly be or comprise one or more clinical factors, in particular the hepatic fibrosis clinical factor score, which can be assayed using the Metavir system (Metavir F score) or using the Ishak system, and/or age at the date of sampling (Age), for example, age at the date of HBP, age at the date of hepatic cytopuncture, age at the date of sampling blood, serum, plasma or urine, and/or body mass index (BMI).

Example 6d) above provides an illustration of such combinations.

In one particular embodiment of the invention, in addition to measuring the levels of expression, more particularly the levels of translation, of genes selected from said list of seventeen genes of the invention, the means of the invention may further comprise measuring or assaying the following other factors:

one or more clinical factors which is or comprises the hepatic fibrosis score (which can be assayed using the Metavir system (Metavir F score) or using the Ishak system), and/or age at the date of sampling (Age), for example age at the date of HBP, age at the date of hepatic cytopuncture, age at the date of sampling blood, serum, plasma or urine, and/or body mass index (BMI); and/or one or more virological factors which is or comprises the genotype of the HCV or HCVs and/or the HCV load before treatment; and/or one or more biological factors other than the levels of expression of genes selected from MBL2, LGALS3BP and IL8, G1P2, CXCL10, CCL21, AFP, CRP, CXCL11, CXCL6, CXCL9, FGF7, MDK, MMP2, SFN, TGFB2 and VEGFD, which is or comprises the concentration of gamma glutamyl transpeptidase (GGP) and/or the concentration of alkaline phosphatase (ALP) and/or the concentration of alanine aminotransferase (ALT) and/ or the concentration of aspartate aminotransferase (AST).

Alternatively or in a complementary manner, in addition to assaying the levels of expression, more particularly the levels of translation, of genes selected from said list of seventeen genes of the invention, the means of the invention may further comprise:

determining the hepatic fibrosis score of said subject, more particularly determining whether the hepatic fibrosis score of said subject is a score which, in the Metavir score system, is at most F1 or at least F2, more particularly at least F2; and/or determining whether the HCV or HCVs which has infected said subject comprises an HCV of genotype 1, 4, 5 or 6, more particularly of genotype 1 or 4, more particularly of genotype 1.

These determinations may be made during step i), or be made independently of step i).

TABLE 21

Values for sensitivity (Se), specificity (Spe), negative predictive value (NPV), positive predictive value (PPV) and LOOCV error which may be associated with a combination of the levels of transcription of selected genes in accordance with the invention (RNA transcripts, more particularly when these RNAs are obtained from a tissue or hepatic cell sample), further combined with other biological factors and/or with clinical factors and/or with virological factors

| No. of the combination of selected genes (see Table 12) | Other biological factors and/or clinical factors and/or virological factors, combined with the levels of expression of the combination of selected genes | Classification model used | Se | Spe | NPV | PPV | LOOCV error |
|---|---|---|---|---|---|---|---|
| $24_{RNA(\S)}$ | viral load before treatment (VLbeforeTTT); concentration of alkaline phosphatase (ALP) | mROC (*) | 81 | 71 | 83 | 68 | ND |

(*) the values for Se, Spe, NPV, PPV and LOOCV error indicated are those for the function of Table 22 below $(\S)$ more particularly, RNAs obtained from tissue or hepatic cell sample ND = not determined

TABLE 22

Example of mROC model (Z function) for a combination of selected genes in accordance with the invention (measurement of their levels of transcription into RNA), further combined with other factors (biological factors other than the levels of expression of selected genes in accordance with the invention and/or clinical factors and/or virological factors), and Example of PT threshold for this function (in fact, threshold maximizing Youden's index δ),

| No. of the combination of selected genes (see Table 12) | Other factors | Example of Z function (mROC model) | Name of function | PT threshold (δ threshold) |
|---|---|---|---|---|
| $24_{RNA(\S)}$ | viral load before treatment (VLbeforeTTT); concentration of alkaline phosphatase (ALP) | Z = −0.051 × $CXCL10^t$ + 0.032 × IL8 + 0.357 × $CCL21^t$ + 0.189 × $MDK^t$ + 0.182 × $LGALS3BP^t$ + 0.052 × $VLbeforeTTT^t$ + 2.644 × $PAL^t$ | Z24ARNsupp | 5.454 |

$_{(\S)}$more particularly, RNA obtained from a tissue or hepatic cell sample

TABLE 23

Example of values for the Box-Cox parameter (λ) which can be used in the Z function indicated in Table 23 above.

| Genes for which it is advised to normalize the value for the level of transcription (RNA) | Example of value of the parameter lambda which can be used for the Z functions of Table 22 above (*) |
|---|---|
| CXCL10 | 0.04 |
| CCL21 | 0.02 |
| LGALS3BP | −0.07 |
| MDK | 0.15 |
| VLbeforeTTT | 0.2 |
| ALP | −0.26 |

(*): lambda, the parameter for Box-Cox transformations [$BMK^t = (BMK^\lambda − 1)/\lambda$]

TABLE 24

AUC value for the function of Table 22

| Name of function | AUC | AUC, lower limit | AUC, upper limit |
|---|---|---|---|
| Z24ARNsupp (see Table 22) | 0.827 | 0.730 | 0.894 |

TABLE 25

Values for sensitivity (Se), specificity (Spe), negative predictive value (NPV), positive predictive value (PPV) and LOOCV error which may be associated with a combination of the levels of protein translation (more particularly into seric proteins) of selected genes in accordance with the invention, further combined with other biological factors and/or with clinical factors and/or with virological factors

| No. of the combination of selected genes (see Table 12) | Other biological factors and/or clinical factors and/or virological factors, combined with the levels of expression of the combination of selected genes | Classification model used | Se | Spe | NPV | PPV | LOOCV error |
|---|---|---|---|---|---|---|---|
| $24_{proteins(\$)}$ | Viral load before treatment (VLbeforeTTT); concentration of gamma glutamyl transpeptidase (GGT); concentration of alkaline phosphatase (ALP) | mROC (*) | 82 | 77 | 83 | 75 | ND |
| $15_{proteins1(\$)}$ | Age at the date of sampling (Age); viral load before treatment (VLbeforeTTT); concentration of alanine aminotransferase (ALT) | mROC (*) | 82 | 77 | 83 | 75 | ND |
| $15_{proteins2(\$)}$ | Age at the date of sampling (Age); viral load before treatment (VLbeforeTTT); concentration of gamma glutamyl transpeptidase (GGT) | mROC (*) | 83 | 74 | 84 | 74 | ND |
| $15_{proteins3(\$)}$ | Viral load before treatment (VLbeforeTTT); concentration of aspartate aminotransferase (AST); concentration of alkaline phosphatase (BMI) | mROC (*) | 86 | 77 | 86 | 76 | ND |
| $15_{proteins4(\$)}$ | body mass index (BMI) | mROC (*) | 81 | 78 | 82 | 76 | ND |

(*) the values for Se, Spe, NPV, PPV and LOOCV error indicated are those for the function of Table 26 below
$_{(\$)}$more particularly, proteins contained in a blood sample and/or in the seric portion of that sample
ND = not determined

TABLE 26

Example of mROC model (Z function) for a combination of selected genes in accordance with the invention (measurement of their levels of translation, more particularly into seric proteins), further combined with other factors (biological factors other than the levels of expression of five selected genes in accordance with the invention and/or clinical factors and/or virological factors), and Example of PT threshold for this function (in fact, threshold maximizing Youden's index δ)

| No. of the combination of selected genes (see Table 12) | Other factors | Example of multivariate classification model (mROC model) | Name of function | PT threshold (δ threshold) |
|---|---|---|---|---|
| 24$_{proteins(\$)}$ | Viral load before treatment (VLbeforeTTT); concentration of gamma glutamyl transpeptidase (GGT); concentration of alkaline phosphatase (ALP) | $Z = -0.353 \times MDK + 0.059 \times IL8^t + 0.456 \times LGALS3BP^t + 0.010 \times CXCL10^t - 0.118 \times CCL21^t + 0.058 \times VLbeforeTTT^t + 0.227 \times GGG^t + 0.408 \times PAL^t$ | Z24PROTsupp | 4.516 |
| 15$_{proteins1(\$)}$ | Age at the date of sampling (Age); viral load before treatment (VLbeforeTTT); concentration of alanine aminotransferase (ALT) | $Z = 0.569 \times LGALS3BPt + 0.033 \times CXCL10^t + 0.059 \times VLbeforeTTT^t - 0.899 \times Age^t - 0.538 \times ALT^t$ | Z15PROTsupp1 | −2.345 |
| 15$_{proteins2(\$)}$ | Age at the date of sampling (Age); viral load before treatment (VLbeforeTTT); concentration of gamma glutamyl transpeptidase (GGT) | $Z = 0.492 \times LGALS3BP^t + 0.018 \times CXCL10^t - 0.701 \times Age^t + 0.058 \times VLbeforeTTT^t + 0.202 \times GGT^t$ | Z15PROTsupp2 | 0.696 |
| 15$_{proteins3(\$)}$ | Viral load before treatment (VLbeforeTTT); concentration of aspartate aminotransferase (AST); concentration of alkaline phosphatase (BMI) | $Z = 0.499 \times LGALS3BP^t + 0.028 \times CXCL10^t + 0.06 \times VLbeforeTTT^t - 1.147 \times AST^t + 0.931 \times PAL^t$ | Z15PROTsupp3 | 3.862 |
| 15$_{proteins4(\$)}$ | Body mass index (BMI) | $Z = 0.451 \times LGALS3BP^t + 0.033 \times CXCL10^t - 0.535 \times IMC^t$ | Z15PROTsupp4 | 0.375 |

($)more particularly, proteins contained in a blood sample and/or in the seric portion of this sample

TABLE 27

Example of values for the Box-Cox parameter (λ) which can be used in the Z functions indicated in Table 26 above

| Genes for which it is advised to normalize the value for the level of transcription (RNA) | Example of value of the parameter lambda which can be used for the Z functions of Table 26 above (*) |
|---|---|
| IL8 | 0.23 |
| LGALS3BP | 0.33 |
| CXCL10 | 0.41 |
| CCL21 | −0.01 |
| VLbeforeTTT | 0.20 |
| GGT | −0.01 |
| ALP | −0.11 |
| ALT | −0.09 |
| AST | −0.30 |
| Age | 0.09 |
| BMI | 0.08 |

(*): lambda, the parameter for Box-Cox transformations [$BMK^t = (BMK^\lambda - 1)/\lambda$]

TABLE 28

AUC value for the Z functions of Table 26

| Name of function | AUC | AUC, lower limit | AUC, upper limit |
|---|---|---|---|
| Z24PROTsupp | 0.872 | 0.812 | 0.916 |
| Z15PROTsupp1 | 0.877 | 0.817 | 0.920 |
| Z15PROTsupp2 | 0.872 | 0.810 | 0.916 |
| Z15PROTsupp3 | 0.869 | 0.806 | 0.913 |
| Z15PROTsupp4 | 0.834 | 0.763 | 0.887 |

In one embodiment of the invention, from said optional list of eleven genes (AFP, CRP, CXCL11, CXCL6, CXCL9, FGF7, MDK, MMP2, SFN, TGFB2 and VEGFD), 0, 1 or 2 genes are selected from among MDK, TGFB2, FGF7 and CXCL6, MMP2 and SFN, more particularly from among MDK, TGFB2, FGF7 and CXCL6, from among MDK, TGFB2, FGF7 and CXCL6, more particularly MDK or at least MDK.

In one embodiment of the invention, the number of these selected genes in accordance with the invention (from among said list of seventeen genes of the invention) is 3, 4 or 5, and:
  from among MBL2, LGALS3BP and IL8, at least MBL2 and/or IL8 is selected;
  from among CXCL10, G1P2 and CCL21, at least G1P2 and/or at least CCL21 is selected;
  from among said optional list of eleven genes (AFP, CRP, CXCL11, CXCL6, CXCL9, FGF7, MDK, MMP2, SFN, TGFB2 and VEGFD), at least 1 gene is selected, in particular 1, 2, or 3 genes; more particularly 0, 1 or 2 genes is/are selected from among MDK, TGFB2, FGF7, CXCL6, MMP2 and SFN, more particularly from among MDK, TGFB2, FGF7 and CXCL6, more particularly at least MDK.

In accordance with a particular embodiment, the levels of expression measured for the genes thus selected are levels of transcription.

In one embodiment of the invention, the number of selected genes in accordance with the invention (from among said list of seventeen genes of the invention) is 2, 3 or 4. Advantageously, the biological sample is a sample of biological fluid, in particular a sample of intracorporal fluid such as blood, serum, plasma, or a urine sample. The levels of expression measured for these genes may thus be levels of translations.

From among said optional list of eleven genes (AFP, CRP, CXCL11, CXCL6, CXCL9, FGF7, MDK, MMP2, SFN, TGFB2 and VEGFD), it is thus possible to select 0, 1 or 2 genes from among MDK, TGFB2, FGF7, CXCL6, MMP2 and SFN, more particularly from MDK, TGFB2, FGF7 and CXCL6, more particularly MDK or at least MDK.

Thus, in particular, the following may be selected:
at least LGALS3BP from among MBL2, LGALS3BP and IL8,
at least CXCL10 from among CXCL10, G1P2 and CCL21, and
0, 1 or 2 genes from among said optional list of eleven genes, more particularly 0, 1 or 2 genes from among MDK, TGFB2, FGF7, CXCL6, MMP2 and SFN, more particularly 0, 1 or 2 genes from among MDK, TGFB2, FGF7 and CXCL6, more particularly MDK or at least MDK;

see for example, the combination No. 24 measured for levels of translations in Tables 17 to 20 above.

As indicated above and illustrated below, in addition to the levels of expression, more particularly translations of these selected genes, it is possible to measure or assay one or more virological factors (such as VLbeforeTTT and/or genotype(s) of the HCV or HCVs) and/or one or more other biological factors (such as GGT and/or ALP) and/or one or more clinical factors (such as the hepatic fibrosis score); see for example, the combination No. 24 measured for levels of translations and combined with VLbeforeTTT, GGT and ALP factors, in Tables 25 to 28 above.

It will be observed that the combination No. 24 has the best sensitivity and specificity when it is measured for levels of translations than when it is measured for levels of transcriptions (sensitivity of 82% and specificity of 74% for the measurement of seric proteins, versus sensitivity of 73% and specificity of 74% for the measurement of hepatic RNAs; see Tables 17 and 13 below).

In one embodiment of the invention, the combination of genes selected from said list of seventeen genes of the invention is combination No. 15, or No. 9, or No. 24.

Advantageously, the levels of expression of these selected genes are levels of translations.

As indicated above and illustrated below, in addition to the levels of expression of these selected genes, one or more virological factors (such as VLbeforeTTT and/or genotype (s) of the HCV or HCVs) and/or several other biological factors (such as GGT and/or ALP and/or ALT and/or AST) and/or one or more clinical factors (such as hepatic fibrosis score and/or Age and/or BMI) may be measured or assayed.

In accordance with a complementary aspect of the invention, the application relates to products or reagents for the detection and/or determination and/or measurement of said assays, more particularly for the detection and/or assay of the levels of expression of said selected genes, and to manufactured articles, compositions, pharmaceutical compositions, kits, tubes or solid supports comprising such reagents, as well as to computer systems (in particular, computer program product and computer device), which are specially adapted to carrying out a method of the invention.

The application is in particular relative to a reagent which specifically detects a transcription product (RNA) of one of said genes selected from said list of seventeen genes of the invention, or a translation product of one of said genes selected from said list of seventeen genes of the invention (protein, or post-translational form of this protein, such as a specific fragment of this protein).

The application is in particular relative to reagents which specifically detect each of the transcription products (RNA) of said genes selected from said list of seventeen genes of the invention, or each of the translation products of said genes selected from said list of seventeen genes of the invention (protein, or post-translational form of this protein, as a specific fragment of this protein).

Advantageously, a set of such reagents is formed, each of the reagents detecting said transcription products of said selected genes and/or each of the reagents detecting said translation products of said genes selected from said list of seventeen genes of the invention, i.e. a set of reagents which specifically detects at least one expression product for each of these genes.

Preferably, said reagents not only specifically detect a transcription or translation product, but can also quantify it.

In particular, the application pertains to a manufactured article comprising said reagents as a combination product (or combined form, or combined preparation), in particular for their simultaneous, separate or sequential use. This manufactured article may, for example, be in the form of a set of reagents, or a kit.

Clearly, the characteristics of combinations of selected genes described above and those illustrated below are applicable to the reagents of the invention mutatis mutandis.

Said reagents may, for example, hybridize specifically to the RNA of said selected genes and/or to the cDNA corresponding to these RNAs (under at least stringent hybridization conditions), or bind specifically to proteins encoded by said selected genes (or to specific fragments of these proteins), for example in an antigen-antibody type reaction.

At least stringent hybridization conditions are known to the skilled person. The conditions may, for example, be as follows:
for filter hybridization: in 5×SSC, 2% sodium dodecyl sulphate (SDS), 100 micrograms/mL single strand DNA at 55-65° C. for 8 hours, and washing in 0.2×SSC and 0.2% SDS at 60-65° C. for thirty minutes;
for a hybridization by PCR: the PCR conditions indicated in Example 1 below.

Said reagents of the invention may in particular be:
nucleic acids (DNA, RNA, mRNA, cDNA), including oligonucleotide aptamers, optionally tagged to allow them to be detected, in particular with fluorescent tags which are well known to the skilled person, or
protein ligands such as proteins, polypeptides or peptides, for example aptamers, and/or antibodies or fragments of antibodies.

The nucleic acids of the invention may, for example, be primers and/or probes (see SEQ ID NO: 1 to 34 in Table 32 below), in particular pairs of primers (see the pairs of primers indicated in Table 32 below). For each of said genes selected from said list of seventeen genes of the invention, the skilled person can construct a pair of primers and/or a probe which specifically hybridizes to this gene. A manufactured article of the invention may thus comprise the number of primers and/or probes necessary for the detection of the RNA or cDNA of each of said selected genes.

The sequence of nucleic acids of the invention may, for example, be constituted by 9 to 40 nucleotides, more particularly 10 to 30 nucleotides, more particularly 14 to 29 nucleotides, more particularly 19 to 24 nucleotides.

The primer sequences of one pair may, for example, be the sequences of a fragment of the sequence of one of said selected genes and a fragment of its complementary sequence (see Table 1 indicating the accession numbers of the sequences for these genes). One and/or the other of these two primer sequences might not be strictly identical to the sequence of a gene fragment or its complementary sequence; one and/or the other of these two primer sequences may:
- be derived from one or more nucleotide substitutions and/or additions and/or deletions, more particularly one or more nucleotide substitutions, and/or have a sequence identity of at least 80%, or at least 85%, or at least 90%, or at least 95% with the sequence for this fragment or its complementary sequence (identity calculated over the longest of the two aligned sequences–optimal alignment),
- provided that the resulting pair of primers has conserved the capacity to specifically hybridize to one of said selected genes.

A primer pair of the invention advantageously has a delta Tm of approximately 1° C. or less. In one embodiment of the invention, a primer pair of the invention targets an approximately 70 to 120 bp amplicon (i.e. the sense primer and the anti-sense primer hybridize at such positions on the target nucleic acid that the amplicon produced by elongation of these hybridized primers has a length of approximately 70 to 120 bp).

Examples of such primers and primer pairs are presented in Table 32 below (SEQ ID NO: 1 to 34, forming 17 primer pairs).

The sequence for a probe of the invention may, for example, be:
- the sequence for a fragment of the sequence of one of said selected genes (see Table 1 indicating the accession numbers for sequences for these genes), said fragment hybridizing specifically to the sequence for that gene;
- a sequence:
   - which derives from the sequence for such a fragment by one or more nucleotide substitutions and/or additions and/or deletions, more particularly by one or more nucleotide substitutions, and/or a sequence which has a sequence identity of at least 80%, or at least 85%, or at least 90%, or at least 95% with the sequence for this fragment or its complementary sequence (identity calculated for the longest of the two aligned sequences–optimal alignment), but which has conserved the capacity to hybridize specifically to one of said selected genes;

and/or
- a complementary sequence of such sequences.

A probe of the invention may in particular be a probe for real time amplification, intended for use with a primer pair in accordance with the invention. Alternatively, detection by real time PCR may use molecules known as intercalating (for example; SYB green) which have the ability of interposing themselves into double stranded structures.

The ligands of the invention, which bind specifically to proteins encoded by the genes selected from said list of seventeen genes of the invention (or to specific fragments of these proteins) may, for example, be proteins, polypeptides or peptides, for example aptamers or antibodies or antibody fragments.

The skilled person can produce such a ligand for each of said selected genes.

The antibodies may, for example, be produced by immunization of a non-human mammal (such as a rabbit) with a protein encoded by said selected gene or with an antigenic fragment of such a protein, optionally associated or coupled with an immunization adjuvant (such as a Freund's adjuvant or KLH—keyhole limpet haemocyanin), for example by intraperitoneal or subcutaneous injection, and by collecting the antibodies obtained thereby in the serum of said mammal.

Monoclonal antibodies may be produced using a lymphocyte hybridization technique (hybridomas), for example using the technique by Köhler and Milstein 1975 (see also U.S. Pat. No. 4,376,110), the human B cell hybridoma technique (Kosbor et al. 1983; Cole et al. 1983), or the technique for immortalizing lymphocytes with the aid of the Epstein-Barr virus—EBV—(Cole et al. 1985). Examples of such antibodies are IgG, IgM, IgE, IgA, IgD or any sub-class of these immunoglobulins.

Antibodies modified by genetic engineering may be produced, such as recombinant antibodies or chimeras, humanized by grafting one or more CDRs (Complementary Determining Region).

The antibodies used in the invention may be fragments of antibodies or artificial derivatives of such fragments, provided that these fragments or derivatives have said specific binding property. Such fragments may, for example, be Fab, F(ab')2, Fv, Fab/c or scFv (single chain fragment variable) fragments.

Examples of antibodies are given in Table 29 below.

TABLE 29

Examples of specific antibodies

| Encoding gene | Antibody | Example of supplier | Catalogue reference of Product |
|---|---|---|---|
| MBL2 | anti-human MBL2 polyclonal antibody (rabbit IgG) | Sigma-Aldrich | HPA 002027 |
| G1P2 | anti-human G1P2 polyclonal antibody (goat IgG) | R&D Systems | AF4845 |
| MDK | anti-human MDK polyclonal antibody (rabbit IgG) | Calbiochem | NE1044 |

TABLE 29-continued

Examples of specific antibodies

| Encoding gene | Antibody | Example of supplier | Catalogue reference of Product |
|---|---|---|---|
| LGALS3BP | anti-human LGALS3BP polyclonal antibody (rabbit IgG) | Sigma-Aldrich | AV54779 |
| CXCL10 | anti-human CXCL10/IP-10 polyclonal antibody (goat IgG) | R&D Systems | AB-266-PB |
| FGF7 | anti-FGF7 Monoclonal antibody produced in the mouse (11F1, IgG2b clone) | Novus Biologicals | NB 110-74673 |
| IL8 | anti-human IL8 monoclonal antibody produced in the mouse (6G4 clone) | Sigma-Aldrich | WH0003576M5 |
| TGFB2 | anti-human TGFB2 monoclonal antibody produced in the mouse (Zg-12, IgG2b clone) | Santa Cruz Biotechnology | sc-80347 |
| CCL21 | anti-human CCL21 polyclonal antibody (mouse IgG) | Novus Biologicals | H0006366-B01P |
| CXCL6 | anti-human CXCL6/GCP2 monoclonal antibody (clone 60910), (mouse IgG1) | R&D Systems | MAB333 |
| MMP2 | anti-MMP2 antibody [EP1329Y] | Abcam | ab51127 |
| CXCL11 | anti-human CXCL11/I-TAC monoclonal antibody (clone 87328) (mouse IgG2A) | R&D Systems | MAB672 |
| AFP | anti-AFP monoclonal antibody produced in the mouse (clone 39, IgG1) | Santa Cruz Biotechnology | sc-130302 |
| VEGFD | anti-human VEGFD monoclonal antibody produced in the mouse (clone MM0007-7E79, IgG2) | Novus Biologicals | NB 110-60973 |
| CRP | anti-human CRP monoclonal antibody produced in the mouse (clone 3H109, IgG1) | Santa Cruz Biotechnology | sc-70883 |
| CXCL9 | anti-human CXCL9 monoclonal antibody produced in the mouse (clone 49106, IgG1) | R&D Systems | MAB392 |

Other examples of means for measuring the levels of transcription of selected genes are also presented in Table 44 (immunoassay kits).

Said reagents may also comprise a tag for their detection (for example a fluorophore).

Said reagents may be in the form of composition(s), pharmaceutical composition(s), for example in one or more tube(s) or in (a) well(s) of a nucleic acid amplification plate.

Said reagents may be as a mixture or in distinct forms or physically separated from each other.

Said reagents may be fixed to a solid support, for example a support formed from a polymer, from plastic, in particular polystyrene, from glass or from silicon.

Said reagents may be directly or indirectly attached to said solid support, for example via a binding agent or capture agent which is attached to the solid support. This binding or capture agent may comprise a portion fixed to said solid support and a portion which comprises a ligand which binds specifically to one of said selected genes. Such a ligand may, for example, be an antibody, a monoclonal antibody, in particular a human antibody such as a IgG, IgM or IgA, or a fragment of an antibody of this type which has conserved the binding specificity.

Said solid support may, for example, be a plastic plate, in particular formed from polystyrene, comprising a plurality of analytical wells, such as a protein titre or microtitre plate, for example an ELISA plate.

Said solid support may also be formed by magnetic or non-magnetic microbeads, for microtitration, for example using the technique described by Luminex.

Said solid support may, for example, be a nucleic acid, protein or peptide chip, for example a plastic, glass or silicon chip.

Said reagents do not have to be fixed to a solid support and may, for example, be contained in a solution such as a buffer, for example to store them until use. More particularly, the reagents may be nucleic acids which are not bound to a solid support the nucleotide sequence of which is adapted to specific amplification (the case of primers or primer pairs) and/or to specific hybridization (in the case of probes) of the transcription product (RNA) of one of said genes selected from said list of seventeen genes of the invention.

In addition to reagents which detect the transcription or translation products of mammalian genes, more particularly human genes, and in particular genes selected from said list of seventeen genes of the invention, a manufactured article in accordance with the application may optionally comprise other reagents, for example reagents that can be used to measure or determine one or more virological factors and/or one or more clinical factors.

As an example, an article manufactured in accordance with the application may comprise reagents which specifically detect one or more hepatitis viruses, and/or its or their genotype.

In one embodiment, the application pertains to a manufactured article comprising reagents in a combined preparation for their simultaneous, separate or sequential use, said reagents being constituted by:

reagents which specifically detect (preferably, which specifically detect and can be used for quantification) each of the transcription or translation products of 2 to 35 mammalian genes, more particularly 2 to 35 human genes, (for example, by specifically hybridizing to the RNA of these genes and/or to the cDNA obtained by reverse transcription of these RNA, or by specifically binding to proteins encoded by these genes), said 2 to 35 mammalian genes, or, if appropriate, said 2 to 35 human genes, comprising said genes selected from said list of seventeen genes of the invention, and optionally, reagents which specifically detect (preferably which specifically detect and can be used for quantification) a hepatitis virus and/or the genotype of a hepatitis virus.

In this manufactured article, the number of mammalian genes, more particularly human genes the transcription or translation products of which may be detected is 2 to 35, more particularly 2 to 34, more particularly 2 to 33, more particularly 2 to 28, more particularly 2 to 26, more particularly 2 to 25, more particularly 2 to 24, more particularly 2 to 23, in particular 2 to 22, more particularly 2 to 20, more particularly 2 to 19, more particularly 2 to 10, more particularly 2 to 9, more particularly 2 to 8, more particularly 2 to 7, more particularly 2 to 6 (for example 2, 3, 4, 5 or 6), more particularly 2 to 5 (for example 2, 3, 4 or 5).

The mammalian genes, more particularly the human genes, the transcription or translation products of which may be detected by the reagents contained in the manufactured article of the application comprise said genes selected from said list of seventeen genes of the invention, and optionally other genes, which are not the genes selected from said list of seventeen genes of the invention, but for which the expression product, more particularly of translation, may be of interest, such as the genes listed here as "other biological factors" (for example, the gene coding for gamma glutamyl transpeptidase or GGT and/or the gene coding for alkaline phosphatase or ALP).

In the manufactured article of the application, the number of reagents which specifically detect the expression product of mammalian genes (more particularly human genes) which are not genes selected from said list of seventeen genes of the invention (for example a reagent specifically detecting GGT and a reagent specifically detecting ALP) is preferably a maximum of 5, more particularly 4 or fewer, more particularly 3 or fewer, more particularly 2 or fewer, more particularly 2 or 1 or 0.

Said manufactured article may thus, for example, be:
one or more tubes,
a kit, in particular a kit comprising one or more tubes,
a solid support, for example, formed from plastic, polystyrene, glass, silicon or polymer or comprising a magnetic material such as iron oxide, such as:
   a plate formed from plastic comprising a plurality of analysis wells, such as
      a nucleic acid amplification plate comprising wells for receiving a biological sample and a reaction mixture for nucleic acid amplification,
      a titration or microtitration plate, more particularly an ELISA plate,
   magnetic microbeads (for example microbeads formed from iron oxide and coated with a polymer to which the proteins or polypeptides can adhere or be attached by chemical coupling);
a nucleic acid, protein, polypeptide or peptide chip.

Optionally, the manufactured article of the invention further comprises instructions (for example, an instruction sheet) for measuring the level of expression of said selected genes on a biological sample collected or obtained from said subject, more particularly to carry out a method of the invention.

Said manufactured article may further comprise one or more of the following elements:
an instrument for removing said sample, in particular:
   a needle and/or a syringe, more particularly a needle and/or a syringe for taking a sample of an intracorporal liquid such as blood, and/or
   a needle adapted for hepatic cytopuncture, for example a needle with a diameter of 18 to 22G), and/or
   a needle and/or a catheter and/or a biopsy gun adapted for HBP;
a computer program product or software product, in particular a computer program product or statistical analysis software, for example a computer program product of the invention as described below;
RNA extraction reagents;
a reverse transcriptase;
a polymerase, for example a Taq polymerase;
nucleotides (dNTP).

In particular, the application pertains to said manufactured article or to said reagents for their use in a method for predicting whether a subject infected with one or more HCVs has a high probability of responding to an anti-HCV treatment which is to comprise administering interferon and ribavirin (or their prodrugs) or whether, in contrast, that subject has a high probability of not responding to that anti-HCV treatment, more particularly to said manufactured article or to said reagents for their use in a predictive method of the invention.

In particular, this use may comprise:
taking a biological sample from said subject, in particular by inserting a needle or catheter into the body of said subject, and
using said reagents in said method on this biological sample, or on a sample comprising nucleic acids and/or proteins and/or polypeptides and/or peptides extracted or purified from said biological sample, or on a sample comprising cDNAs which are susceptible of having been obtained by reverse transcription of said nucleic acids.

This use may, for example, comprise:
taking a biological sample of said subject, optionally transformed by:
   extraction or purification of RNAs of said removed sample and optionally by reverse transcription of the extracted RNAs, or by
   extraction or purification of its proteins from said sample, and
using said reagents of the invention on this optionally transformed biological sample.

Said biological sample may be taken by inserting a sampling instrument, in particular by inserting a needle or a catheter, into the body of said subject.

The sampling instrument is primarily inserted in order to remove intracorporal fluid from said subject (such as blood, for example) and/or a portion of hepatic tissue from said subject (for example by HBP) and/or hepatic cells from said subject (for example by hepatic cytopuncture).

This instrument may thus be inserted, for example:
- into a vein, an artery or a blood vessel of said subject to remove blood from said subject; and/or
- into the liver of said subject, in order to take a sample of hepatic parenchyma, i.e. to carry out a hepatic biopsy puncture (HBP), for example transjugularly or transparietally; and/or
- through the skin to the liver of said subject, so as to carry out a hepatic cytopuncture.

The application pertains in particular to said manufactured article or to said reagents for their use in a method for the treatment of hepatopathy which comprises liver tissue damage, more particularly a hepatic fibrosis, more particularly an anti-HCV therapy method.

This use may in particular comprise using said reagents in a method of the invention in order to predict whether a subject infected with one or more HCVs has a strong probability of responding to an anti-HCV treatment which will comprise the administration of interferon and ribavirin or whether, in contrast, that subject has a high probability of not responding to this anti-HCV treatment, more particularly in an anti-HCV therapy method which comprises administering interferon and the administration of ribavirin (or their prodrugs), more particularly in an anti-HCV therapy method which comprises, as a first line treatment, the administration of interferon and the administration of ribavirin (or their prodrugs).

If said subject is predicted to be a non-responder, the clinician may elect not to administer a treatment to the subject which comprises (more particularly which is essentially constituted by) administering interferon and administering ribavirin (or their prodrugs), more particularly not to administer such a treatment as a first line treatment. In such a situation, the clinician may, for example, elect to administer an anti-HCV treatment which does not comprise (or which is not essentially constituted by) the administration of interferon and the administration of ribavirin (or their prodrugs) to the subject, more particularly to administer such a treatment to the subject as a first line treatment. The clinician may alternatively elect not to administer anti-HCV treatment to the subject, at least as a first line treatment. If said subject is predicted to be a responder, the clinician may elect to administer an anti-HCV treatment, in particular a treatment which comprises (more particularly which is essentially constituted by) administering interferon and administering ribavirin (or their prodrugs), more particularly to administer, as a first line treatment, a treatment which comprises (more particularly which is essentially constituted by) administering interferon and administering ribavirin (or their prodrugs).

This use may, for example, comprise:
- using said reagents of the invention on a biological sample which has been taken from said subject, and which optionally has been transformed, for example:
  - by extraction and/or purification of the RNAs of said sample and, optionally, by reverse transcription of the extracted RNAs, or
  - by extraction and/or purification of proteins and/or polypeptides and/or peptides of said sample which has been taken,
- in order to predict whether a subject infected with one or more HCVs has a strong probability of responding to an anti-HCV treatment which will comprise the administration of interferon and ribavirin or whether, in contrast, this subject has a high probability of not responding to this anti-HCV treatment,
- optionally, determining the HCV genotype infecting said patient and/or determining his hepatic fibrosis score (more particularly, determining whether this score is a score of at least F2 using the Metavir system).

If said subject is predicted to be a non-responder, the clinician may elect not to administer a treatment to the subject which comprises (more particularly which is essentially constituted by) administering interferon and administering ribavirin (or their prodrugs), more particularly of not administering such a treatment to the subject as a first line treatment. In such a situation, the clinician may, for example, elect to administer an anti-HCV treatment which does not comprise (or which is not essentially constituted by) administering interferon and administering ribavirin (or their prodrugs), more particularly of administering such a treatment to the subject as a first line treatment. The clinician may alternatively elect not to administer anti-HCV treatment to the subject, at least as a first line treatment. If said subject is predicted to be a responder, the clinician may elect to administer an anti-HCV treatment, in particular a treatment which comprises (more particularly which is essentially constituted by) administering interferon and administering ribavirin (or their prodrugs), more particularly of administering, as a first line treatment, a treatment which comprises (more particularly which is essentially constituted by) administering interferon and administering ribavirin (or their prodrugs).

Said treatment may, for example, be an anti-HCV treatment as described above and illustrated below.

The application also pertains to a drug or combination of drugs for the treatment of a hepatopathy comprising an attack of the tissue of the liver, more particularly a hepatic fibrosis (such as standard interferon or pegylated interferon, in a monotherapy or a polytherapy associating one or more other active principles, in particular ribavirin), in particular an anti-HCV treatment for its use in the treatment method of the invention.

The application also pertains to a computer program product to be stored in a memory of a processing unit or on a removable memory support for cooperation with a reader of said processing unit. The computer program product of the invention comprises instructions for carrying out a method of the invention, in particular for carrying out a statistical analysis adapted to carrying out a method of the invention (in particular adapted for the multivariate statistical analysis of the measurements, and more particularly the levels of expression of said selected genes) and/or for the construction of a multivariate classification model adapted to carrying out a method in accordance with the invention.

The application also pertains to a computer unit, a computer device, or computer, comprising a processing unit with the following stored or recorded in its memory:
- a computer program product of the invention, and, optionally,
- measurements, or measurement values, of the levels of expression (transcription and/or translation) of said selected genes.

The term "comprising", which is synonymous with "including" or "containing", is an open term and does not exclude the presence of one or more additional element(s), ingredient(s) or step(s) of the method which are not explicitly indicated, while the term "consisting" or "constituted" is a closed term which excludes the presence of any other additional element, step or ingredient which is not explicitly disclosed. The term "essentially consisting" or "essentially constituted" is a partially open term which does not exclude the presence of one or more additional element(s), ingredient (s) or step(s) provided that this (these) additional element(s), ingredient(s) or step(s) do not materially affect the basic properties of the invention.

As a consequence, the term "comprising" (or "comprise(s)") includes the terms "consisting", "constituted" as well as the terms "essentially consisting" and "essentially constituted by".

With the aim of facilitating reading of the application, the description has been separated into various paragraphs, sections and embodiments. It should not be assumed that these separations disconnect the substance of one paragraph, section or embodiment from that of another paragraph, section or embodiment. On the contrary, the description encompasses all possible combinations of the various paragraphs, sections, phrases and embodiments which it contains.

The content of the bibliographic references cited in the application is specifically incorporated into the content of the application by reference.

The following examples are given purely by way of illustration. They do not in any way limit the invention.

EXAMPLES

Example 1

Construction of Classification Models

1. Populations and Patients, Measurement of the Level of Gene Expression, Determination of Response to Treatment:

The study was approved by the local Ethics Committee in accordance with the Helsinki Declaration and all of the patients gave their informed written consent.
Presentation of Patients The patients were adult patients infected with the hepatitis C virus (HCV), monitored at the Hôpital Beaujon (Clichy, France).

The clinical diagnosis of infection with the hepatitis C virus of the selected patients was established on the basis of the detection of antibodies directed against HCV proteins and the detection of circulating HCV RNA.

The serology of the HCV to be detected was carried out using the $3^{rd}$ generation Abbott test (AxSYM™ HCV Version 3.0 (Abbott) Technique MEIA; index >1=positive; index <1=negative) and the VERSANT® HCV-RNA 3.0 (bDNA) ASSAY HCV RNA quantification test from Siemens Healthcare Diagnostics (quantification limit=615-7 690 000 IU/mL).

In order to establish a homogeneous cohort which was entirely representative of the exemplified pathology, patients susceptible of presenting chronic hepatic diseases of origins other than the hepatitis C virus (such as a chronic hepatic disease due to an infection with hepatitis B virus) were excluded from the study. Other exclusion criteria were also applied, namely excessive alcohol consumption, haemochromatosis, auto-immune hepatitis, Wilson's disease, $\alpha$-1 antitrypsin deficiency, primary sclerosing cholangitis, primary biliary cirrhosis or subsequent anti-HCV treatment.

One hundred and forty patients were thus selected.

Table 30 below presents the clinical, biological and virological data of the patients who were thus selected. These data were collected before the patient received an antiviral treatment, in this case during a hepatic biopsy puncture (HBP).

In Table 30 below:
IU=International Unit
NR patients=patients not responsive to treatment;
R patients=patients responsive to treatment;
RR patients=responder-relapser patients;
see below for the definition of these three sub-populations or cohorts.

TABLE 30

| Clinical, biological and virological data | | | | |
|---|---|---|---|---|
| Clinical, biological and virological data | Patients | NR patients | R patients | RR patients |
| n | 140 | 51 | 68 | 21 |
| Sex: male (%)/female (%) | 89 (64)/51 (36) | 31 (61)/20 (39) | 43 (63)/25 (37) | 15 (71)/6 (29) |
| Age [mean ± standard deviation (range)] | 45.8 ± 8.5 (27-72) | 47.3 ± 8.6 (33-72) | 44.7 ± 9.0 (27-65) | 44.4 ± 4.9 (34-66) |
| Source of infection [n (%)] | | | | |
| blood transfusion | 30 (21) | 11 (22) | 16 (23) | 3 (14) |
| intravenous administration of an unknown drug | 42 (30) | 17 (33) | 21 (31) | 4 (19) |
|  | 68 (49) | 23 (45) | 31 (46) | 14 (67) |
| Alanine aminotransferase (ALT) IU/L [mean ± standard deviation (range)] | 106 ± 73 (18-459) | 112 ± 81 (30-354) | 102 ± 74 (20-459) | 100 ± 36 (18 176) |
| HCV genotypes [n (%)] | | | | |
| 1 | 76 (54.3) | 40 (78.4) | 28 (41.2) | 8 (38.1) |
| 2 | 13 (9.3) |  | 10 (14.7) | 3 (14.3) |
| 3 | 19 (13.6) | 3 (5.9) | 12 (17.6) | 4 (19.0) |
| 4 | 31 (22.1) | 8 (15.7) | 17 (25.0) | 6 (28.6) |
| 5 | 1 (0.7) | 0 | 1 (1.5) | 0 |
| Fibrosis score (Metavir F score) [n (%)] | | | | |
| 0 | 1 (0.7) | 0 | 1 (1.5) | 0 |
| 1 | 45 (32.1) | 15 (29.5) | 26 (38.2) | 4 (19.0) |
| 2 | 53 (37.9) | 18 (35.3) | 29 (42.7) | 6 (28.6) |

TABLE 30-continued

Clinical, biological and virological data

| Clinical, biological and virological data | Patients | NR patients | R patients | RR patients |
|---|---|---|---|---|
| 3 | 18 (12.9) | 9 (17.6) | 3 (4.4) | 6 (28.6) |
| 4 | 22 (15.7) | 9 (17.6) | 9 (13.2) | 4 (19.0) |
| unknown | 1 (0.7) | 0 | 0 | 1 (4.8) |

Sampling:

A hepatic biopsy puncture (HBP) was carried out on each patient before any antiviral treatment was received. The HBPs were carried out in accordance with good clinical practice. The biopsies were immediately stored at −80° C. with a view to extracting total RNA, and treated with paraffin for the histological studies. A sample of serum was taken from each of the patients included in the study in a period of +/−6 months from the date of the biopsy, but always before the patient received antiviral treatment.

Treatment of Hepatic Biopsy Samples (for Measurement of RNAs):

The levels of expression of the genes (in fact, level of RNA transcription) were measured on each of the 140 biopsies (1 biopsy per patient).

The hepatic biopsies were ground in nitrogen using a ceramic pestle and mortar (100% manual grinding).

The powder was recovered using a scalpel (Swann Morton 22, Reference 0208).

a) Extraction of RNAs

The powder obtained was dissolved in 1 mL of RNAble® Ref. GEXEXT00, Laboratoires Eurobio, France, to which 100 µL of chloroform had been added.

The mixture obtained was placed in ice or at 4° C. for 5 minutes, then was centrifuged at 13 000 g for 15 minutes.

The upper aqueous phase containing the RNAs was recovered into a fresh tube and 1 volume of isopropanol was added to it.

The tube was agitated by repeated inversion and was kept at 4° C. overnight, then was centrifuged at 13 000 g for 15 minutes. The supernatant was eliminated and the pellet containing the RNAs was taken up in a volume of 70% ethanol (extemporaneously prepared) and centrifuged again.

The pellet of RNA precipitate obtained was dried in the open air for approximately 1 hour then dissolved in 15 µL of water and stored at −80° C.

b) Measurement of RNAs

The evaluation of the concentration of extracted RNAs was carried out by measuring the optical density using a spectrometer (Nanodrop), and was verified after a freeze/thaw cycle.

The extracted RNAs were then diluted to obtain a 50 ng/µL solution.

Quality controls of the RNA were carried out by real time PCR (see below) by screening a ubiquitous expression control gene (known as endogenous), to verify that the RNA had not degraded (in fact, screening RPLP0).

Reverse Transcription or RT Step:

The reverse transcription was carried out on 200 ng of RNA in a reaction mixture produced in a volume of 20 µL, comprising the following reagents:

TABLE 31

| Reagent and reference product | Starting solution | Volume |
|---|---|---|
| SUPERSCRIPT II RNase H reverse transcriptase, Invitrogen, ref: 18064014 | 200 U/µL | 0.5 µL |
| SUPER SCRIPT 5X buffer Invitrogen, ref: 18064014 | — | 4.0 µL |
| RNAsin Promega, ref: N2111 | 40 U/µL | 0.5 µL |
| DTT | 100 mM | 2.0 µL |
| The 4 dNTPs GE Healthcare, ref: 28406552 | 10 mM | 1 µL |
| Pd(N) primers RANDOM HEXAMERS 50 (A260) units, 51 Perbio, ref: MB216601 | 0.5 µg/µL | 6.0 µL |
| RNA | 50 ng/µL | 4.0 µL |
| H$_2$O | | qs 20 µL |

The reverse transcription reactions were carried out at the following temperatures:
- at 20° C. for 10 minutes, then
- at 42° C. for 30 minutes, and
- at 99° C. for 5 minutes.

At this stage, the reaction mixtures were frozen or aliquoted or used directly for real time PCR amplification.

Quantitative Real Time PCR Step (qPCR):

The amplification was carried out using a Light Cycler® 480 (Roche Diagnostics, Mannheim, Germany). The results were generated using Light Cycler® Software 4.05/4.1.

Light Cycler® technology can be used to continuously monitor the appearance of the amplification products due to emission of a quantity of fluorescence which is proportional to the quantity of amplified product, which is itself dependent on the quantity of targets initially present in the sample to be analysed. Quantification (in relative values) of the gene expression was carried out using the method which is known by the name $2^{-\Delta Ct}$ ($2^{-\Delta Ct} = 2^{-(Ct_{target}-Ct_{reference})}$; see Livak and Schmittgen 2001; Schmitten and Livak 2008), utilizing the values for "Cycle Threshold", or Ct, determined by the quantitative real time PCR apparatus. The smaller the value of Ct, the higher the initial quantity of transcribed RNA.

The reaction mixtures and the protocol used are described in the instruction leaflet in the LIGHT CYCLER® 480 SYBR GREEN I MASTER MIX kit (Roche Diagnostics, Mannheim, Germany; U.S. Pat. Nos. 4,683,202; 4,683,195; 4,965,188; 6,569,627).

After the reverse transcription step, the reaction mixtures (cDNAs) were diluted to 1/40th (to verify the quality) or to 1/100th (for the target genes) before using them in qPCR.

For each gene, the qPCRs were carried out in a reaction volume of 10 µL on a 384 well plate:
- 5 µL of reverse transcription reaction, diluted to 1/40th (or 1/100th);
- 4.8 µL of reaction mixture from the Light Cycler® 480 SYBR Green I Master mix kit;
- 0.1 µL of a 50 µM solution for each of the two primers, i.e. a final volume of 0.5 µM for each primer.

The reaction mixtures were generally prepared for the 384 well plates.

The following primers were used:

TABLE 32

Examples of primers

| Symbol | Sense primer | SEQ ID NO: | Antisense primer | SEQ ID NO: |
|---|---|---|---|---|
| MBL2 | GGCACGTATCAAAAAGTGGCTG | 1 | ATTTCACCATTGGTCAGGAAGAACT | 2 |
| G1P2 | GAGGCAGCGAACTCATCTTTGCCA | 3 | CCGCCAGCATCTTCACCGTCA | 4 |
| MDK | GGGCAGCGAGATGCAGCAC | 5 | CCACTCAGCGCACTCGCTCC | 6 |
| LGALS3BP | TGACCCCTCCGAGGCTCTTC | 7 | ATGTCACCATCGTTCACGCCTT | 8 |
| CXCL10 | CTGACTCTAAGTGGCATTCAAGGAG | 9 | GGTTGATTACTAATGCTGATGCAGG | 10 |
| FGF7 | CACAGTGGTACCTGAGGATCGATAA | 11 | GCCACTGTCCTGATTTCCATGAT | 12 |
| IL8 | CACCGGAAGGAACCATCTCACTGT | 13 | TCCTTGGCAAAACTGCACCTTCA | 14 |
| TGFB2 | AGAGTGCCTGAACAACGGATT | 15 | CCATTCGCCTTCTGCTCTT | 16 |
| CCL21 | CTCCATCCCAGCTATCCTGTTCTT | 17 | TCTGCACATAGCTCTGCCTGAGA | 18 |
| CXCL6 | GTTTACGCGTTACGCTGAGAGTAAA | 19 | CGTTCTTCAGGGAGGCTACCA | 20 |
| MMP2 | ACTGCGGTTTTCTCGAATCCA | 21 | GGTATCCATCGCCATGCTCC | 22 |
| SFN | CGACAAGAAGCGCATCATTGAC | 23 | CTGTTGGCGATCTCGTAGTGGA | 24 |
| CXCL11 | GTGTGCTACAGTTGTTCAAGGCTT | 25 | CTCAATATCTGCCACTTTCACTGCT | 26 |
| AFP | ACCCGAACTTTCCAAGCCATAACT | 27 | CCACATCCAGGACTAGTTTCTGGATT | 28 |
| VEGFD | CCTCGTACATTTCCAAACAGCTCT | 29 | TGGCAAGCACTTACAACCTGTATG | 30 |
| CRP | GACGTGACCATGGAGAAGCTGTT | 31 | AAGCCTTCCTCGACATGTCTGTCT | 32 |
| CXCL9 | ATCCACCTACAATCCTTGAAAGAC | 33 | TCCATTCTTCAGTGTAGCAATGATTT | 34 |
| RPLP0 | GGCGACCTGGAAGTCCAACT | 35 | CCATCAGCACCACAGCCTTC | 36 |

The qPCRs were carried out using the following temperature conditions:
 a step for initiating denaturing at 95° C. for 10 minutes;
 50 cycles of: —denaturing at 95° C. for 15 seconds;
 hybridization/elongation at 65° C. for 30 seconds.

Each target sample was amplified in duplicate. In order to overcome variations in the initial quantities of total RNA from one sample to another, at the same time a duplicate amplification was carried out of the RNAs of a gene used as an endogenous control, such as a gene involved in cellular metabolic cascades, for example RPLP0 (also known by the name 36B4; GENBANK accession number NM_001002) or TBP (GENBANK accession number NM_003194). In fact, the gene RPLP0 was used here as the endogenous control. The quality of RNA extraction from the 140 biopsies was evaluated on the basis of the value of Ct of the reference gene, RPLP0. The classification was carried out as follows:
 RPLP0 Ct less than 22: very good RNA quality;
 RPLP0 Ct from 22 to 24: good RNA quality;
 RPLP0 Ct more than 24 and less than 26: average RNA quality;
 RPLP0 Ct of 26 or more: poor RNA quality.

In order to increase the reliability of the bio-statistical analyses, only the data from RNA extraction of very good and good quality (RPLP0 Ct<24) were retained; there were 128 biopsies [91.4% of the 140 samples] of which 107 had a status of responder or non-responder strict; see Table 33 below. The quantity of transcripts of a target gene was deduced from the Ct ("Cycle threshold") which corresponded to the number of PCR cycles necessary in order to obtain a significant fluorescence signal. The target samples were normalized on the basis of their RPLP0 (or, if necessary, TBP) content, using the $2^{-\Delta Ct}$ method.

This value for the normalized measurement in this case is in general denoted "BMK" (for biomarker). The BMK values obtained for each of the 128 patients are presented in Tables 34 to 36 below.

Treatment of Serum Samples (for the Measurement of Seric Proteins):

The protein measurements were carried out using the kits indicated in Table 44 below, following the recommendations of the manufacturer.

TABLE 33

Clinical, biological and virological data

| Clinical, biological and virological data | Patients | NR patients | R patients | RR patients |
|---|---|---|---|---|
| n | 128 | 44 | 63 | 21 |
| Sex: male (%)/female (%) | 82 (64)/46 (36) | 25 (57)/19 (43) | 42 (67)/(21 (33) | 15 (71)/6 (29) |

TABLE 33-continued

Clinical, biological and virological data

| Clinical, biological and virological data | Patients | NR patients | R patients | RR patients |
|---|---|---|---|---|
| Age [mean ± standard deviation (range)] | 47.0 ± 8.7 (27-73) | 46.1 ± 8.9 (27-66) | 48.1 ± 8.9 (35-73) | 47.4 ± 7.8 (35-67) |
| Source of infection [n (%)] | | | | |
| blood transfusion | 28 (22) | 10 (23) | 15 (24) | 3 (14) |
| intravenous administration of an unknown drug | 37 (29) | 13 (30) | 20 (32) | 4 (19) |
|  | 63 (49) | 21 (48) | 28 (44) | 14 (67) |
| Alanine aminotransferase (ALT) IU/L [mean ± standard deviation (range)] | 112 ± 82 (18-459) | 114 ± 80 (30-354) | 119 ± 92 (30-459) | 88 ± 37 (18-176) |
| HCV genotypes [n (%)] | | | | |
| 1 | 70 (55) | 37 (84) | 25 (40) | 8 (38) |
| 2 | 12 (9) | 0 (0) | 9 (14) | 3 (14) |
| 3 | 19 (15) | 3 (7) | 12 (19) | 4 (19) |
| 4 | 26 (20) | 4 (9) | 16 (25) | 6 (29) |
| 5 | 1 (1) | 0 (0) | 1 (2) | 0 (0) |
| Fibrosis score (Metavir F score) [n (%)] | | | | |
| 0 | 0 (0) | 0 (0) | 0 (0) | 0 (0) |
| 1 | 41 (32) | 14 (32) | 23 (37) | 4 (19) |
| 2 | 49 (38) | 15 (34) | 28 (44) | 6 (29) |
| 3 | 17 (13) | 8 (18) | 3 (5) | 6 (29) |
| 4 | 20 (16) | 7 (16) | 9 (14) | 4 (19) |
| unknown | 1 (1) | 0 (0) | 0 (0) | 1 (5) |

TABLE 34

Patients' BMK values for the genes MBL2, G1P2, MDK, LGALS3BP and CXCL10 (Ct normalized in accordance with the $2^{-\Delta Ct}$ method)

| Patient | Status (NR, R or RR) | MBL2 | G1P2 | MDK | LGALS3BP | CXCL10 |
|---|---|---|---|---|---|---|
| 59 | R | 0.993 | 0.877 | 0.090 | 0.045 | 0.01 |
| 62 | R | 5.333 | 0.943 | 0.043 | 0.113 | 0.10 |
| 73 | R | 1.440 | 1.064 | 0.055 | 0.060 | 0.23 |
| 125 | R | 1.419 | 1.257 | 0.058 | 0.012 | 0.02 |
| 306 | R | 5.134 | 3.568 | 0.125 | 0.273 | 0.12 |
| 344 | R | 1.047 | 0.646 | 0.045 | 0.037 | 0.06 |
| 346 | R | 4.004 | 0.601 | 0.032 | 0.133 | 0.02 |
| 504 | R | 1.796 | 0.563 | 0.028 | 0.044 | 0.06 |
| 513 | R | 1.510 | 0.280 | 0.034 | 0.035 | 0.04 |
| 528 | R | 2.694 | 1.261 | 0.188 | 0.082 | 0.07 |
| 530 | R | 4.127 | 0.144 | 0.023 | 0.052 | 0.02 |
| 546 | R | 4.317 | 0.236 | 0.039 | 0.056 | 0.02 |
| 569 | R | 2.166 | 0.092 | 0.008 | 0.047 | 0.02 |
| 570 | R | 4.611 | 0.118 | 0.046 | 0.028 | 0.04 |
| 575 | R | 4.563 | 15.348 | 0.525 | 0.360 | 0.44 |
| 577 | R | 6.255 | 0.224 | 0.024 | 0.093 | 0.02 |
| 583 | R | 1.129 | 1.297 | 0.056 | 0.146 | 0.12 |
| 601 | R | 3.758 | 1.053 | 0.125 | 0.069 | 0.03 |
| 613 | R | 1.809 | 0.108 | 0.017 | 0.035 | 0.03 |
| 614 | R | 2.114 | 0.135 | 0.036 | 0.057 | 0.10 |
| 639 | R | 3.306 | 0.109 | 0.031 | 0.021 | 0.03 |
| 45 | R | 7.835 | 0.959 | 0.037 | 0.063 | 0.13 |
| 50 | R | 0.622 | 1.586 | 0.132 | 0.087 | 0.02 |
| 55 | R | 1.828 | 1.275 | 0.054 | 0.046 | 0.03 |
| 63 | R | 1.338 | 12.295 | 0.106 | 0.115 | 0.25 |
| 65 | R | 2.297 | 1.613 | 0.105 | 0.048 | 0.06 |
| 66 | R | 2.780 | 0.308 | 0.054 | 0.028 | 0.05 |
| 71 | R | 0.588 | 0.564 | 0.021 | 0.014 | 0.01 |
| 59 | R | 0.993 | 0.877 | 0.090 | 0.045 | 0.01 |
| 72 | R | 1.532 | 0.176 | 0.001 | 0.015 | 0.01 |
| 76 | R | 3.053 | 0.653 | 0.045 | 0.064 | 0.27 |
| 86 | R | 1.636 | 14.123 | 0.060 | 0.103 | 0.40 |
| 88 | R | 1.516 | 2.042 | 0.024 | 0.034 | 0.08 |
| 90 | R | 2.021 | 1.912 | 0.115 | 0.048 | 0.08 |
| 91 | R | 0.889 | 0.664 | 0.051 | 0.023 | 0.11 |
| 92 | R | 0.618 | 0.049 | 0.001 | 0.008 | 0.03 |
| 222 | R | 1.165 | 5.187 | 0.063 | 0.021 | 0.15 |
| 227 | R | 0.933 | 0.119 | 0.002 | 0.014 | 0.02 |
| 366 | R | 2.901 | 0.159 | 0.012 | 0.015 | 0.05 |
| 501 | R | 1.223 | 1.424 | 0.046 | 0.032 | 0.13 |
| 502 | R | 1.189 | 0.465 | 0.056 | 0.022 | 0.12 |
| 503 | R | 1.320 | 0.755 | 0.014 | 0.024 | 0.01 |
| 506 | R | 1.121 | 0.678 | 0.057 | 0.016 | 0.15 |
| 508 | R | 1.784 | 0.143 | 0.032 | 0.028 | 0.12 |
| 523 | R | 1.113 | 0.134 | 0.045 | 0.028 | 0.08 |
| 529 | R | 0.724 | 1.210 | 0.084 | 0.031 | 0.00 |
| 532 | R | 0.790 | 0.245 | 0.207 | 0.029 | 0.02 |
| 535 | R | 0.676 | 15.348 | 0.057 | 0.053 | 0.12 |
| 536 | R | 1.717 | 0.313 | 0.010 | 0.015 | 0.03 |
| 537 | R | 0.719 | 0.080 | 0.014 | 0.012 | 0.01 |
| 538 | R | 1.193 | 5.152 | 0.108 | 0.068 | 0.04 |
| 556 | R | 1.161 | 6.869 | 0.011 | 0.022 | 0.04 |
| 560 | R | 1.395 | 3.249 | 0.028 | 0.038 | 0.15 |
| 565 | R | 2.136 | 4.857 | 0.049 | 0.022 | 0.26 |
| 567 | R | 4.532 | 2.497 | 0.038 | 0.068 | 0.11 |
| 568 | R | 0.990 | 0.055 | 0.005 | 0.007 | 0.01 |
| 571 | R | 2.196 | 0.609 | 0.050 | 0.057 | 0.59 |
| 572 | R | 1.376 | 2.129 | 0.009 | 0.020 | 0.02 |
| 581 | R | 1.098 | 1.210 | 0.034 | 0.036 | 0.03 |
| 585 | R | 1.636 | 3.411 | 0.063 | 0.121 | 0.19 |
| 598 | R | 0.923 | 0.200 | 0.009 | 0.009 | 0.06 |
| 604 | R | 1.717 | 1.061 | 0.157 | 0.124 | 0.03 |
| 605 | R | 1.939 | 5.315 | 0.173 | 0.048 | 0.04 |
| 629 | R | 2.189 | 0.074 | 0.012 | 0.059 | 0.01 |
| 308 | NR | 1.185 | 6.658 | 0.446 | 0.251 | 0.07 |
| 521 | NR | 0.004 | 4.362 | 1.676 | 0.576 | 0.49 |
| 526 | NR | 3.138 | 5.260 | 0.189 | 0.130 | 0.17 |
| 549 | NR | 5.352 | 2.297 | 0.156 | 0.142 | 0.15 |

TABLE 34-continued

Patients' BMK values for the genes MBL2, G1P2, MDK, LGALS3BP and CXCL10 (Ct normalized in accordance with the $2^{-\Delta Ct}$ method)

| Patient | Status (NR, R or RR) | MBL2 | G1P2 | MDK | LGALS3BP | CXCL10 |
|---|---|---|---|---|---|---|
| 574 | NR | 4.228 | 4.959 | 0.191 | 0.241 | 1.04 |
| 618 | NR | 1.490 | 4.757 | 0.152 | 0.221 | 0.20 |
| 619 | NR | 1.873 | 1.542 | 0.075 | 0.151 | 0.15 |
| 636 | NR | 0.000 | 18.765 | 0.712 | 0.459 | 0.87 |
| 646 | NR | 0.068 | 35.383 | 0.314 | 0.529 | 0.16 |
| 657 | NR | 5.242 | 2.949 | 0.782 | 0.075 | 0.17 |
| 658 | NR | 2.395 | 0.322 | 0.018 | 0.019 | 0.07 |
| 664 | NR | 5.637 | 2.704 | 0.046 | 0.063 | 0.08 |
| 6 | NR | 0.115 | 0.685 | 0.688 | 0.044 | 0.02 |
| 46 | NR | 3.010 | 8.969 | 0.308 | 0.164 | 0.21 |
| 58 | NR | 2.462 | 13.881 | 0.631 | 0.149 | 0.07 |
| 75 | NR | 5.483 | 8.664 | 1.248 | 0.265 | 0.55 |
| 80 | NR | 1.834 | 0.963 | 0.030 | 0.032 | 0.15 |
| 83 | NR | 0.013 | 6.169 | 0.476 | 0.164 | 0.18 |
| 145 | NR | 5.278 | 7.490 | 0.255 | 0.193 | 0.02 |
| 167 | NR | 0.532 | 5.046 | 0.521 | 0.099 | 0.08 |
| 509 | NR | 0.016 | 6.126 | 0.172 | 0.045 | 0.22 |
| 516 | NR | 3.470 | 3.160 | 0.043 | 0.065 | 0.11 |
| 524 | NR | 1.400 | 0.286 | 0.028 | 0.042 | 0.08 |
| 527 | NR | 1.223 | 9.318 | 0.276 | 0.457 | 0.07 |
| 534 | NR | 3.249 | 2.129 | 0.140 | 0.048 | 0.11 |
| 582 | NR | 1.729 | 4.675 | 0.034 | 0.037 | 0.25 |
| 596 | NR | 0.809 | 0.914 | 0.069 | 0.059 | 0.33 |
| 602 | NR | 0.001 | 0.091 | 0.012 | 0.019 | 0.04 |
| 645 | NR | 0.000 | 0.069 | 0.032 | 0.017 | 0.00 |
| 647 | NR | 2.819 | 20.393 | 0.053 | 0.097 | 0.12 |
| 649 | NR | 1.157 | 3.918 | 0.053 | 0.051 | 0.51 |
| 650 | NR | 2.107 | 12.381 | 0.233 | 0.241 | 0.27 |
| 651 | NR | 1.765 | 4.773 | 0.253 | 0.146 | 0.05 |
| 659 | NR | 1.866 | 0.690 | 0.024 | 0.016 | 0.05 |
| 660 | NR | 0.782 | 6.612 | 0.037 | 0.074 | 0.10 |
| 662 | NR | 0.008 | 5.483 | 0.047 | 0.049 | 0.38 |
| 665 | NR | 1.306 | 0.576 | 0.026 | 0.042 | 0.04 |
| 666 | NR | 3.506 | 5.796 | 0.221 | 0.095 | 0.05 |
| 563 | NR | 1.532 | 0.235 | 0.011 | 0.038 | 0.07 |
| 573 | NR | 4.500 | 6.892 | 0.047 | 0.134 | 0.40 |
| 599 | NR | 0.486 | 1.248 | 0.010 | 0.013 | 0.04 |
| 641 | NR | 2.928 | 2.454 | 0.028 | 0.035 | 0.02 |
| 49 | RR | 1.993 | 1.905 | 0.076 | 0.128 | 0.17 |
| 505 | RR | 0.824 | 4.084 | 0.037 | 0.082 | 0.01 |
| 514 | RR | 5.098 | 0.525 | 0.021 | 0.082 | 0.04 |
| 579 | RR | 1.091 | 0.147 | 0.006 | 0.019 | 0.04 |
| 643 | RR | 3.193 | 0.390 | 0.054 | 0.058 | 0.05 |
| 56 | RR | 2.505 | 3.249 | 0.349 | 0.062 | 0.13 |
| 60 | RR | 0.771 | 7.945 | 0.192 | 0.059 | 0.08 |
| 87 | RR | 3.063 | 11.432 | 0.077 | 0.104 | 0.42 |
| 531 | RR | 0.002 | 0.103 | 0.034 | 0.006 | 0.01 |
| 533 | RR | 2.042 | 1.145 | 0.041 | 0.046 | 0.05 |
| 543 | RR | 1.306 | 1.548 | 0.075 | 0.112 | 0.26 |
| 554 | RR | 0.002 | 0.148 | 0.014 | 0.029 | 0.05 |
| 557 | RR | 1.094 | 3.317 | 0.001 | 0.057 | 0.17 |
| 558 | RR | 0.862 | 0.289 | 0.006 | 0.015 | 0.03 |
| 559 | RR | 0.933 | 0.871 | 0.007 | 0.028 | 0.06 |
| 562 | RR | 0.002 | 3.668 | 0.075 | 0.112 | 0.18 |
| 576 | RR | 1.464 | 5.187 | 0.069 | 0.136 | 0.25 |
| 588 | RR | 2.704 | 0.053 | 0.008 | 0.127 | 0.00 |
| 589 | RR | 2.809 | 7.387 | 0.054 | 0.094 | 0.29 |

TABLE 35

Patients' BMK values for the genes FGF7, IL8, TGFB2, CCL21, CXCL6, MMP2 and SFN (Ct normalized in accordance with the $2^{-\Delta Ct}$ method)

| Patient | Status (NR, R or RR) | FGF7 | IL8 | TGFB2 | CCL21 | CXCL6 | MMP2 | SFN |
|---|---|---|---|---|---|---|---|---|
| 59 | R | 0.069 | 0.329 | 1.735 | 0.006 | 0.000 | 0.318 | 1.505 |
| 62 | R | 0.000 | 0.058 | 1.803 | 0.017 | 0.080 | 0.648 | 3.494 |
| 73 | R | 0.133 | 0.191 | 0.000 | 0.004 | 0.027 | 0.078 | 0.939 |
| 125 | R | 0.000 | 0.000 | 0.635 | 0.005 | 0.000 | 0.072 | 0.399 |
| 306 | R | 0.000 | 0.372 | 0.000 | 0.018 | 0.186 | 0.722 | 0.000 |
| 344 | R | 0.231 | 0.923 | 0.401 | 0.067 | 0.330 | 0.476 | 6.275 |
| 346 | R | 0.000 | 0.182 | 1.889 | 0.004 | 0.029 | 0.357 | 0.712 |
| 504 | R | 0.000 | 2.289 | 0.000 | 0.012 | 0.142 | 0.193 | 4.228 |
| 513 | R | 0.936 | 0.538 | 3.694 | 0.006 | 0.000 | 0.347 | 3.021 |
| 528 | R | 0.555 | 4.547 | 3.824 | 0.022 | 1.189 | 1.414 | 2.282 |
| 530 | R | 0.080 | 0.000 | 2.514 | 0.009 | 0.000 | 0.690 | 1.469 |
| 546 | R | 0.165 | 0.000 | 1.177 | 0.012 | 0.062 | 2.742 | 2.809 |
| 569 | R | 0.000 | 0.559 | 0.306 | 0.003 | 0.000 | 0.343 | 0.655 |
| 570 | R | 0.075 | 0.371 | 4.823 | 0.006 | 0.000 | 0.318 | 1.288 |
| 575 | R | 0.000 | 0.892 | 2.969 | 0.036 | 0.226 | 0.609 | 0.449 |
| 577 | R | 0.011 | 0.262 | 1.641 | 0.007 | 0.084 | 0.166 | 0.000 |
| 583 | R | 0.121 | 0.230 | 1.548 | 0.015 | 0.367 | 1.057 | 1.283 |
| 601 | R | 0.205 | 0.459 | 4.874 | 0.005 | 0.077 | 0.260 | 0.883 |
| 613 | R | 0.094 | 0.111 | 2.063 | 0.007 | 0.000 | 0.287 | 15.085 |
| 614 | R | 0.282 | 0.218 | 2.362 | 0.011 | 0.078 | 0.563 | 2.204 |
| 639 | R | 0.151 | 0.399 | 0.000 | 0.005 | 0.000 | 0.365 | 9.126 |
| 45 | R | 0.101 | 1.641 | 1.647 | 0.033 | 0.092 | 0.302 | 0.000 |
| 50 | R | 0.102 | 0.444 | 0.529 | 0.013 | 0.027 | 0.274 | 0.213 |
| 55 | R | 0.060 | 1.395 | 0.000 | 0.006 | 0.053 | 0.087 | 0.365 |
| 63 | R | 0.177 | 0.199 | 0.412 | 0.025 | 0.000 | 0.115 | 0.766 |
| 65 | R | 0.098 | 0.168 | 0.232 | 0.012 | 0.013 | 0.113 | 0.106 |
| 66 | R | 0.120 | 0.420 | 0.793 | 0.013 | 0.119 | 0.342 | 0.465 |
| 72 | R | 0.094 | 0.064 | 1.017 | 0.005 | 0.052 | 0.091 | 0.396 |
| 76 | R | 0.210 | 1.257 | 1.125 | 0.012 | 0.051 | 0.221 | 0.742 |
| 86 | R | 0.266 | 0.451 | 1.193 | 0.023 | 0.102 | 0.211 | 0.507 |
| 88 | R | 0.277 | 0.297 | 1.032 | 0.010 | 0.072 | 0.129 | 0.440 |
| 90 | R | 0.088 | 0.089 | 0.518 | 0.012 | 0.045 | 0.170 | 0.119 |

TABLE 35-continued

Patients' BMK values for the genes FGF7, IL8, TGFB2, CCL21, CXCL6, MMP2 and SFN (Ct normalized in accordance with the $2^{-\Delta Ct}$ method)

| Patient | Status (NR, R or RR) | FGF7 | IL8 | TGFB2 | CCL21 | CXCL6 | MMP2 | SFN |
|---|---|---|---|---|---|---|---|---|
| 91 | R | 0.154 | 0.040 | 2.181 | 0.008 | 0.096 | 0.146 | 0.000 |
| 92 | R | 0.000 | 0.087 | 0.278 | 0.005 | 0.027 | 0.029 | 0.136 |
| 222 | R | 0.083 | 0.330 | 0.844 | 0.016 | 0.023 | 0.082 | 0.497 |
| 227 | R | 0.060 | 0.260 | 0.000 | 0.003 | 0.000 | 0.110 | 0.254 |
| 366 | R | 0.039 | 0.179 | 0.995 | 0.009 | 0.020 | 0.269 | 0.081 |
| 501 | R | 0.112 | 0.601 | 0.141 | 0.016 | 0.070 | 0.175 | 0.278 |
| 502 | R | 0.108 | 2.676 | 1.165 | 0.009 | 0.557 | 0.475 | 5.152 |
| 503 | R | 0.000 | 0.109 | 0.295 | 0.004 | 0.011 | 0.081 | 1.257 |
| 506 | R | 0.241 | 10.483 | 1.210 | 0.019 | 0.343 | 0.578 | 1.564 |
| 508 | R | 0.097 | 0.446 | 0.593 | 0.013 | 0.000 | 0.161 | 0.271 |
| 523 | R | 0.382 | 2.329 | 1.537 | 0.018 | 0.176 | 0.251 | 0.536 |
| 529 | R | 0.119 | 0.354 | 0.277 | 0.012 | 0.053 | 0.248 | 0.452 |
| 532 | R | 0.050 | 0.387 | 0.796 | 0.010 | 0.032 | 0.106 | 1.454 |
| 535 | R | 0.041 | 0.328 | 0.399 | 0.025 | 0.026 | 0.177 | 0.507 |
| 536 | R | 0.037 | 0.119 | 0.705 | 0.010 | 0.180 | 0.123 | 0.148 |
| 537 | R | 0.215 | 0.058 | 0.272 | 0.007 | 0.027 | 0.177 | 1.218 |
| 538 | R | 0.000 | 0.041 | 0.337 | 0.014 | 0.000 | 0.111 | 0.139 |
| 556 | R | 0.033 | 0.063 | 0.540 | 0.008 | 0.000 | 0.124 | 0.168 |
| 560 | R | 0.021 | 0.530 | 0.717 | 0.008 | 0.082 | 0.188 | 0.911 |
| 565 | R | 0.000 | 1.079 | 0.441 | 0.006 | 0.000 | 0.247 | 0.172 |
| 567 | R | 0.076 | 1.297 | 3.227 | 0.006 | 0.356 | 0.578 | 0.295 |
| 568 | R | 0.011 | 0.127 | 0.312 | 0.002 | 0.000 | 0.048 | 0.046 |
| 571 | R | 0.000 | 0.804 | 1.028 | 0.026 | 0.036 | 0.291 | 1.338 |
| 572 | R | 0.008 | 0.064 | 1.110 | 0.005 | 0.005 | 0.068 | 0.078 |
| 581 | R | 0.173 | 2.549 | 4.084 | 0.006 | 0.129 | 0.642 | 1.145 |
| 585 | R | 0.032 | 0.818 | 1.248 | 0.017 | 0.112 | 0.370 | 0.306 |
| 598 | R | 0.118 | 0.660 | 0.940 | 0.008 | 0.033 | 0.093 | 0.128 |
| 604 | R | 0.051 | 0.084 | 0.829 | 0.011 | 0.082 | 0.239 | 0.263 |
| 605 | R | 0.023 | 0.178 | 0.688 | 0.009 | 0.000 | 0.082 | 0.398 |
| 629 | R | 0.071 | 0.152 | 0.927 | 0.003 | 0.000 | 0.293 | 1.366 |
| 308 | NR | 0.000 | 0.853 | 1.569 | 0.022 | 0.115 | 0.415 | 1.357 |
| 521 | NR | 1.231 | 3.732 | 12.168 | 0.052 | 0.170 | 2.732 | 0.000 |
| 526 | NR | 0.075 | 2.370 | 1.279 | 0.028 | 0.169 | 0.362 | 1.137 |
| 549 | NR | 0.000 | 0.979 | 0.616 | 0.023 | 0.080 | 1.828 | 7.835 |
| 574 | NR | 0.000 | 5.756 | 3.824 | 0.031 | 0.139 | 0.710 | 0.000 |
| 618 | NR | 0.104 | 1.035 | 1.329 | 0.025 | 0.294 | 0.607 | 1.419 |
| 619 | NR | 0.000 | 0.301 | 5.081 | 0.011 | 0.064 | 0.225 | 3.519 |
| 636 | NR | 0.109 | 0.270 | 2.144 | 0.048 | 0.081 | 0.774 | 0.880 |
| 646 | NR | 0.418 | 0.518 | 1.729 | 0.018 | 0.087 | 0.547 | 1.952 |
| 657 | NR | 1.741 | 4.840 | 0.000 | 0.013 | 2.412 | 1.075 | 1.444 |
| 658 | NR | 0.559 | 0.557 | 0.000 | 0.009 | 0.000 | 0.195 | 0.000 |
| 664 | NR | 0.536 | 0.953 | 0.856 | 0.029 | 0.139 | 1.098 | 0.719 |
| 6 | NR | 0.000 | 2.648 | 5.296 | 0.004 | 0.000 | 1.505 | 0.345 |
| 46 | NR | 0.394 | 0.911 | 0.269 | 0.021 | 0.115 | 0.478 | 0.366 |
| 58 | NR | 0.136 | 0.616 | 0.613 | 0.016 | 0.152 | 0.266 | 1.753 |
| 75 | NR | 0.125 | 0.908 | 1.404 | 0.033 | 0.082 | 0.755 | 2.274 |
| 80 | NR | 0.270 | 0.745 | 1.032 | 0.018 | 0.096 | 0.124 | 1.490 |
| 83 | NR | 0.322 | 0.231 | 1.173 | 0.073 | 0.154 | 0.325 | 0.730 |
| 145 | NR | 0.333 | 0.755 | 1.905 | 0.023 | 0.196 | 0.895 | 0.323 |
| 167 | NR | 0.037 | 0.923 | 3.215 | 0.018 | 0.112 | 0.228 | 0.000 |
| 509 | NR | 0.131 | 1.157 | 1.235 | 0.025 | 0.218 | 0.378 | 0.236 |
| 516 | NR | 0.069 | 0.844 | 0.895 | 0.017 | 0.049 | 0.323 | 0.145 |
| 524 | NR | 0.296 | 0.949 | 0.927 | 0.009 | 0.025 | 0.262 | 0.129 |
| 527 | NR | 0.172 | 0.657 | 1.619 | 0.045 | 0.060 | 0.529 | 0.367 |
| 534 | NR | 0.065 | 1.828 | 0.237 | 0.017 | 0.194 | 0.437 | 0.584 |
| 582 | NR | 0.094 | 2.949 | 4.014 | 0.012 | 0.409 | 0.732 | 0.277 |
| 596 | NR | 0.018 | 0.883 | 2.049 | 0.017 | 0.080 | 0.384 | 0.078 |
| 602 | NR | 0.019 | 0.936 | 1.021 | 0.010 | 0.059 | 0.115 | 0.241 |
| 645 | NR | 2.479 | 0.000 | 0.078 | 0.004 | 0.000 | 2.085 | 0.000 |
| 647 | NR | 0.299 | 0.192 | 0.927 | 0.028 | 0.110 | 0.356 | 0.384 |
| 649 | NR | 0.409 | 2.742 | 1.959 | 0.034 | 0.167 | 0.311 | 0.563 |
| 650 | NR | 0.216 | 5.816 | 1.042 | 0.022 | 0.446 | 0.398 | 1.177 |
| 651 | NR | 0.000 | 0.940 | 0.868 | 0.009 | 0.150 | 0.115 | 1.173 |
| 659 | NR | 0.212 | 4.423 | 0.838 | 0.006 | 0.237 | 0.191 | 0.300 |
| 660 | NR | 0.229 | 1.113 | 1.602 | 0.021 | 0.308 | 0.224 | 0.000 |
| 662 | NR | 0.161 | 0.046 | 0.244 | 0.022 | 0.051 | 0.233 | 0.099 |
| 665 | NR | 0.126 | 0.949 | 0.821 | 0.014 | 0.061 | 0.177 | 0.835 |
| 666 | NR | 0.000 | 2.799 | 0.832 | 0.028 | 0.000 | 0.222 | 0.226 |
| 642 | NR | 2.099 | 13.408 | 2.158 | 0.046 | 1.682 | 1.699 | 1.459 |
| 67 | NR | 0.084 | 0.104 | 0.380 | 0.006 | 0.036 | 0.191 | 0.184 |
| 563 | NR | 0.000 | 0.330 | 0.871 | 0.005 | 0.06 | 0.21 | 1.11 |
| 573 | NR | 0.038 | 0.323 | 1.306 | 0.028 | 0.06 | 0.41 | 0.85 |
| 599 | NR | 0.000 | 0.262 | 0.536 | 0.005 | 0.01 | 0.03 | 0.00 |
| 641 | NR | 0.478 | 0.657 | 0.362 | 0.012 | 0.15 | 0.29 | 0.21 |

TABLE 35-continued

Patients' BMK values for the genes FGF7, IL8, TGFB2, CCL21, CXCL6, MMP2 and SFN (Ct normalized in accordance with the $2^{-\Delta Ct}$ method)

| Patient | Status (NR, R or RR) | FGF7 | IL8 | TGFB2 | CCL21 | CXCL6 | MMP2 | SFN |
|---|---|---|---|---|---|---|---|---|
| 49 | RR | 0.054 | 0.284 | 1.032 | 0.018 | 0.00 | 0.19 | 2.91 |
| 505 | RR | 0.000 | 0.410 | 1.098 | 0.006 | 0.00 | 0.12 | 0.00 |
| 514 | RR | 0.000 | 1.053 | 1.376 | 0.011 | 0.07 | 0.40 | 1.20 |
| 579 | RR | 0.622 | 0.483 | 2.685 | 0.004 | 0.07 | 0.23 | 2.97 |
| 643 | RR | 1.959 | 15.835 | 4.627 | 0.014 | 1.20 | 1.78 | 1.18 |
| 56 | RR | 0.000 | 0.363 | 0.943 | 0.011 | 0.00 | 0.15 | 0.00 |
| 60 | RR | 0.000 | 0.145 | 0.272 | 0.015 | 0.00 | 0.12 | 0.45 |
| 87 | RR | 0.099 | 1.608 | 2.242 | 0.021 | 0.12 | 0.36 | 0.28 |
| 531 | RR | 0.904 | 0.053 | 8.340 | 0.002 | 0.00 | 2.79 | 0.12 |
| 533 | RR | 0.116 | 3.084 | 1.840 | 0.008 | 0.19 | 0.33 | 0.18 |
| 543 | RR | 0.611 | 0.597 | 1.193 | 0.040 | 0.06 | 0.66 | 1.04 |
| 554 | RR | 0.000 | 1.072 | 1.439 | 0.005 | 0.12 | 0.26 | 0.95 |
| 557 | RR | 0.074 | 0.700 | 0.898 | 0.007 | 0.06 | 0.22 | 0.32 |
| 558 | RR | 0.094 | 0.983 | 1.343 | 0.002 | 0.10 | 0.28 | 0.20 |
| 559 | RR | 0.005 | 0.536 | 1.173 | 0.005 | 0.07 | 0.15 | 0.20 |
| 562 | RR | 0.104 | 1.380 | 2.445 | 0.007 | 0.14 | 0.69 | 0.51 |
| 576 | RR | 0.065 | 1.064 | 1.500 | 0.010 | 0.13 | 0.55 | 0.75 |
| 588 | RR | 0.114 | 0.255 | 1.424 | 0.002 | 0.04 | 0.29 | 0.18 |
| 589 | RR | 0.082 | 0.315 | 2.204 | 0.012 | 0.03 | 0.41 | 1.63 |
| 591 | RR | 0.204 | 0.113 | 1.244 | 0.013 | 0.05 | 0.47 | 0.17 |
| 592 | RR | 0.294 | 7.781 | 6.566 | 0.020 | 1.09 | 1.60 | 0.53 |

TABLE 36

Patients' BMK values for the genes CXCL11, AFP, VEGFD, CRP and CXCL9 (Ct normalized in accordance with the $2^{-\Delta Ct}$ method)

| Patient | Status (NR, R or RR) | CXCL11 | AFP | VEGFD | CRP | CXCL9 |
|---|---|---|---|---|---|---|
| 59 | R | 0.111 | 0.026 | 0.000 | 1.390 | 0.166 |
| 62 | R | 0.454 | 0.024 | 1.705 | 0.710 | 1.526 |
| 73 | R | 0.518 | 0.005 | 0.867 | 0.707 | 0.264 |
| 125 | R | 0.095 | 0.030 | 0.000 | 0.197 | 0.092 |
| 306 | R | 1.753 | 0.045 | 1.017 | 1.834 | 1.464 |
| 344 | R | 0.186 | 0.053 | 2.141 | 3.719 | 1.386 |
| 346 | R | 0.123 | 0.007 | 0.962 | 337.775 | 0.225 |
| 504 | R | 0.132 | 0.023 | 0.000 | 7.387 | 0.349 |
| 513 | R | 0.062 | 0.031 | 0.705 | 0.519 | 0.129 |
| 528 | R | 0.291 | 0.004 | 2.099 | 40.085 | 0.613 |
| 530 | R | 0.121 | 0.161 | 0.376 | 14.774 | 0.174 |
| 546 | R | 0.167 | 0.049 | 0.000 | 0.269 | 0.148 |
| 569 | R | 0.140 | 0.048 | 0.261 | 9.190 | 0.246 |
| 570 | R | 0.253 | 0.113 | 0.107 | 1.945 | 0.572 |
| 575 | R | 1.329 | 0.050 | 0.437 | 0.809 | 0.969 |
| 577 | R | 0.102 | 0.058 | 0.747 | 0.737 | 0.236 |
| 583 | R | 0.824 | 0.038 | 0.162 | 1.866 | 0.620 |
| 601 | R | 0.208 | 0.008 | 0.420 | 1.227 | 0.129 |
| 613 | R | 0.158 | 0.014 | 0.251 | 1.670 | 1.091 |
| 614 | R | 0.459 | 0.019 | 0.207 | 3.745 | 0.804 |
| 639 | R | 0.095 | 0.108 | 0.760 | 0.940 | 0.168 |
| 45 | R | 0.597 | 0.032 | 0.182 | 1.575 | 0.793 |
| 50 | R | 0.043 | 0.010 | 0.147 | 0.480 | 0.174 |
| 55 | R | 0.168 | 0.033 | 0.207 | 0.747 | 0.076 |
| 63 | R | 0.376 | 0.036 | 0.419 | 1.765 | 0.235 |
| 65 | R | 0.219 | 0.024 | 0.299 | 0.874 | 0.275 |
| 66 | R | 0.192 | 0.013 | 0.255 | 2.420 | 0.386 |
| 72 | R | 0.024 | 0.005 | 0.118 | 2.321 | 0.107 |
| 76 | R | 0.399 | 0.034 | 0.221 | 1.548 | 0.844 |
| 86 | R | 0.329 | 0.025 | 0.077 | 2.107 | 0.316 |
| 88 | R | 0.127 | 0.047 | 0.239 | 0.207 | 0.183 |
| 90 | R | 0.233 | 0.014 | 0.272 | 0.633 | 0.493 |
| 91 | R | 0.285 | 0.021 | 0.197 | 0.605 | 0.835 |
| 92 | R | 0.091 | 0.011 | 0.015 | 1.747 | 0.283 |
| 222 | R | 0.300 | 0.067 | 0.116 | 0.946 | 0.185 |
| 227 | R | 0.082 | 0.042 | 0.046 | 0.693 | 0.085 |
| 366 | R | 0.108 | 0.040 | 0.680 | 2.918 | 0.430 |
| 501 | R | 0.538 | 0.047 | 0.090 | 3.864 | 0.320 |
| 502 | R | 0.193 | 0.014 | 0.135 | 5.836 | 0.702 |
| 503 | R | 0.059 | 0.027 | 0.126 | 2.848 | 0.091 |
| 506 | R | 0.714 | 0.014 | 0.835 | 0.566 | 1.619 |
| 508 | R | 0.620 | 0.049 | 0.130 | 8.311 | 0.838 |
| 523 | R | 0.312 | 0.018 | 0.086 | 0.159 | 1.270 |
| 529 | R | 0.262 | 0.025 | 0.083 | 0.859 | 0.523 |
| 532 | R | 0.074 | 0.035 | 0.148 | 0.099 | 0.330 |
| 535 | R | 0.191 | 0.006 | 0.229 | 0.850 | 0.050 |
| 536 | R | 0.129 | 0.006 | 0.100 | 17.509 | 0.344 |
| 537 | R | 0.053 | 0.019 | 0.122 | 1.429 | 0.200 |
| 538 | R | 0.134 | 0.006 | 0.178 | 0.189 | 0.071 |
| 556 | R | 0.088 | 0.021 | 0.000 | 0.880 | 0.058 |
| 560 | R | 0.611 | 0.012 | 0.082 | 0.326 | 0.946 |
| 565 | R | 0.536 | 0.049 | 0.337 | 3.918 | 0.156 |
| 567 | R | 0.463 | 0.005 | 0.273 | 2.056 | 0.429 |
| 568 | R | 0.027 | 0.002 | 0.068 | 3.238 | 0.107 |
| 571 | R | 2.370 | 0.088 | 0.624 | 1.414 | 2.603 |
| 572 | R | 0.092 | 0.018 | 0.053 | 4.908 | 0.087 |
| 581 | R | 0.100 | 0.007 | 0.355 | 2.014 | 0.132 |
| 585 | R | 0.976 | 0.012 | 0.334 | 0.874 | 1.185 |
| 598 | R | 0.235 | 0.018 | 0.126 | 1.064 | 0.249 |
| 604 | R | 0.451 | 0.043 | 0.151 | 0.622 | 0.238 |
| 605 | R | 0.156 | 0.026 | 0.114 | 0.838 | 0.089 |
| 629 | R | 0.064 | 0.013 | 0.618 | 3.824 | 0.108 |
| 308 | NR | 4.942 | 0.100 | 0.293 | 1.636 | 0.096 |
| 521 | NR | 1.459 | 0.117 | 0.601 | 0.336 | 0.712 |
| 526 | NR | 0.597 | 0.012 | 0.294 | 2.129 | 1.352 |
| 549 | NR | 0.838 | 0.062 | 0.350 | 0.809 | 1.248 |
| 574 | NR | 4.516 | 0.095 | 2.136 | 1.993 | 0.584 |
| 618 | NR | 0.503 | 0.025 | 0.580 | 1.157 | 0.236 |
| 619 | NR | 0.516 | 0.000 | 0.804 | 4.976 | 0.459 |
| 636 | NR | 2.042 | 0.128 | 0.236 | 0.312 | 0.432 |
| 646 | NR | 1.072 | 0.014 | 0.000 | 1.039 | 0.470 |
| 657 | NR | 0.405 | 0.041 | 0.518 | 0.367 | 0.149 |
| 658 | NR | 0.081 | 0.044 | 0.000 | 15.725 | 0.304 |
| 664 | NR | 0.114 | 0.110 | 0.976 | 38.452 | 0.284 |
| 6 | NR | 0.018 | 0.002 | 0.125 | 0.010 | 0.018 |
| 46 | NR | 0.180 | 0.007 | 0.000 | 0.758 | 0.073 |
| 58 | NR | 0.263 | 0.050 | 0.289 | 0.194 | 0.070 |
| 75 | NR | 1.087 | 0.068 | 1.227 | 0.112 | 0.500 |
| 80 | NR | 0.410 | 0.041 | 0.209 | 3.411 | 0.283 |
| 83 | NR | 1.053 | 0.043 | 0.365 | 0.635 | 0.476 |
| 145 | NR | 0.204 | 0.047 | 0.149 | 1.636 | 0.307 |
| 167 | NR | 0.155 | 0.012 | 0.184 | 3.811 | 0.153 |

TABLE 36-continued

Patients' BMK values for the genes CXCL11, AFP, VEGFD, CRP and CXCL9 (Ct normalized in accordance with the $2^{-\Delta Ct}$ method)

| Patient | Status (NR, R or RR) | CXCL11 | AFP | VEGFD | CRP | CXCL9 |
|---|---|---|---|---|---|---|
| 509 | NR | 0.983 | 0.008 | 0.286 | 0.263 | 1.102 |
| 516 | NR | 0.382 | 0.063 | 0.435 | 12.252 | 0.660 |
| 524 | NR | 0.258 | 0.018 | 0.000 | 2.612 | 0.642 |
| 527 | NR | 0.198 | 0.031 | 0.460 | 1.315 | 0.179 |
| 534 | NR | 1.347 | 0.069 | 0.115 | 3.494 | 0.369 |
| 582 | NR | 1.007 | 0.031 | 0.232 | 2.099 | 0.351 |
| 596 | NR | 0.564 | 0.005 | 0.267 | 0.635 | 1.240 |
| 602 | NR | 0.124 | 0.024 | 0.048 | 1.177 | 0.328 |
| 645 | NR | 0.013 | 0.000 | 3.458 | 0.017 | 0.006 |
| 647 | NR | 0.402 | 0.018 | 0.480 | 1.495 | 0.212 |
| 649 | NR | 0.376 | 0.049 | 0.423 | 1.479 | 0.603 |
| 650 | NR | 0.321 | 0.052 | 1.227 | 0.351 | 0.241 |
| 651 | NR | 0.257 | 0.035 | 0.279 | 0.809 | 0.133 |
| 659 | NR | 0.092 | 0.067 | 0.090 | 0.576 | 0.286 |
| 660 | NR | 0.098 | 0.035 | 0.127 | 0.717 | 0.207 |
| 662 | NR | 0.230 | 0.040 | 0.111 | 0.315 | 0.237 |
| 665 | NR | 0.070 | 0.009 | 0.710 | 1.847 | 0.280 |
| 666 | NR | 0.158 | 0.037 | 0.415 | 0.543 | 0.186 |
| 642 | NR | 2.488 | 0.049 | 0.117 | 0.768 | 2.780 |
| 67 | NR | 0.044 | 0.021 | 0.078 | 3.972 | 0.278 |
| 563 | NR | 0.233 | 0.007 | 0.000 | 1.597 | 1.444 |
| 573 | NR | 0.740 | 0.064 | 0.339 | 0.355 | 0.319 |
| 599 | NR | 0.200 | 0.007 | 0.164 | 0.763 | 0.104 |
| 641 | NR | 0.134 | 0.010 | 0.163 | 0.607 | 0.204 |
| 49 | RR | 0.382 | 0.111 | 1.007 | 0.570 | 1.343 |
| 505 | RR | 0.029 | 0.054 | 0.384 | 0.234 | 0.045 |
| 514 | RR | 0.017 | 0.089 | 0.000 | 23.344 | 0.476 |
| 579 | RR | 0.193 | 0.024 | 0.441 | 5.856 | 0.314 |
| 643 | RR | 0.222 | 0.011 | 4.500 | 6.751 | 0.626 |
| 56 | RR | 0.372 | 0.027 | 0.000 | 0.428 | 0.388 |
| 60 | RR | 0.272 | 0.021 | 0.361 | 0.187 | 0.078 |
| 87 | RR | 0.361 | 0.020 | 0.135 | 0.338 | 0.171 |
| 531 | RR | 0.007 | 0.001 | 0.576 | 0.064 | 0.009 |
| 533 | RR | 0.274 | 0.015 | 0.061 | 0.107 | 0.346 |
| 543 | RR | 0.712 | 0.025 | 0.468 | 1.227 | 2.014 |
| 554 | RR | 0.168 | 0.031 | 0.274 | 4.993 | 0.578 |
| 557 | RR | 0.384 | 0.010 | 0.133 | 0.722 | 0.208 |
| 558 | RR | 0.067 | 0.023 | 0.235 | 0.208 | 0.111 |
| 559 | RR | 0.230 | 0.009 | 0.209 | 1.094 | 0.425 |
| 562 | RR | 0.306 | 0.035 | 0.266 | 0.818 | 0.245 |
| 576 | RR | 1.419 | 0.041 | 0.216 | 2.211 | 1.366 |
| 588 | RR | 0.024 | 0.020 | 0.351 | 1.676 | 0.034 |
| 589 | RR | 0.399 | 0.050 | 0.287 | 0.034 | 0.197 |
| 591 | RR | 0.425 | 0.016 | 0.112 | 0.186 | 0.674 |
| 592 | RR | 0.930 | 0.034 | 0.299 | 0.908 | 0.976 |

TABLE 44

| Tags | IL8 | LGALS3BP | MDK | CXCL10/IP-10 | CCL21 |
|---|---|---|---|---|---|
| | Kits for protein measurements | | | | |
| EIA kit | QUANTIKINE HUMAN CXCL8/IL-8 IMMUNOASSAY | 90K/MAb-2 BP ELISA | HUMAN MIDKINE ELISA | QUANTIKINE HUMAN CXCL10/IP10 IMMUNOASSAY | HUMAN CCL21/6Ckine IMMUNOASSAY |
| Supplier | R&D Systems | Abnova | Abnova | R&D Systems | R&D Systems |
| Reference | D8000C | KA0140 | KA0028 V.02 | DIP100 | D6C00 |
| ELISA type | Sandwich | Sandwich | Sandwich | Sandwich | Sandwich |
| Types of samples | Serum, plasma, cell culture medium | serum, cell culture supernatant | Serum, plasma, tissue, cell culture medium | Serum, plasma, saliva, cell culture medium | serum, plasma |
| Test volume | 50 µL | 20 µL | 25 µL | 75 µL | 100 µL |
| Solid phase | MAb anti-IL8 | MAb anti-LGALS3BP | PAb anti MDK | MAb anti-IP10 | MAb anti-CCL21 |
| Conjugate | PAb-HRP anti-IL8 | MAb-HRP anti-LGALS3BP | PAb-biotin anti-MDK | PAb-HRP anti-IP10 | PAb-HRP anti-CCL21 |
| Sensitivity | 3.5 pg/mL | 0.92 ng/mL | 0.33 ng/mL | 1.67 pg/mL | 9.9 pg/mL |
| Detection range | 31.2-2000 pg/mL | 12.5 to 200 ng/mL | 2-10 ng/mL | 7.8-500 pg/mL | 91-371 pg/mL |
| | Kits for protein assays | | | | |
| Specificity | Human recombinant IL8,, no cross reaction with ANG, AR, CNTF, b-ECGF, EGF, Epo, acidic FGF, basic FGF, FGF-4, FGF-5, FGF-6, GCSF, GM-CSF, GROa, GROb, GROg, sgp130, HBEGF, HGF, I-309, IFN-g, IGF-I, IGF-II, IL-1a, IL-1b, IL-1ra, IL-1 sRI | Human LGALS3BP | Human MIDKINE | Native recombinant IP10, no cross reaction with BLC/BCA-1, ENA-78, GCP-2, GROa, GROg, IFN-g, IL-8, IL-8 (endothelial cell-derived), I-TAC, MIG, NAP-2, SDF-1a, human recombinant SDF-1b, BLC/BCA-1, CRG-2 (IP-10), GCP-2, KC, MIG, mouse recombinant SDF-1a and pig recombinant Il-8 | Human CCL21 |

PAb = polyclonal antibody
MAb = monoclonal antibody

Administration of Antiviral Treatment and Analysis of Patient's Response:

After HBP and removing serum, each patient received an antiviral treatment which is currently considered to be the standard treatment for hepatitis C, namely a treatment based on a combination of two antiviral agents, namely alpha interferon and ribavirin.

In the context of the test described here, all of the patients received the following treatment:
either:
  pegylated alpha-2b interferon (PEG-INTRON®; Schering Plough Corporation; Kenilworth, N.J.; U.S.A.) in a dose of 1.5 g/kg/week, and
  ribavirin (REBETOL®; Schering Plough Corporation; Kenilworth, N.J.; U.S.A.) in a dose of:
    800 to 1200 mg/kg/day for those patients who had been infected with at least one genotype 1 and/or 4 and/or 5 of HCV, or in a dose of
    800 mg/kg/day for those patients who had been infected with at least one genotype 2 and/or 3 of HCV,
or:
  pegylated alpha-2a interferon (PEGASYS®; Roche Corporation; F. Hoffmann-La Roche Ltd.; Basel, Switzerland) in a dose of 180 g/kg/week, and
  ribavirin (COPEGUS®; Roche Corporation; F. Hoffmann-La Roche Ltd.; Basel, Switzerland) in a dose of 1000 to 1200 mg/kg/day.

The treatment was administered for 24 weeks for those patients who had been infected with at least one genotype 2 and/or 3 of HCV, and for 48 weeks for those patients who had been infected with at least one genotype 1 and/or 4 and/or 5 of HCV.

The viral load was measured in week 24, at the end of treatment and 6 months after treatment had ended by quantification of the HCV RNAs present in the serum from each patient, with the aid of the VERSANT® HCV RNA 3.0 (bDNA) ASSAY HCV RNA quantification test from Siemens Healthcare Diagnostics (quantification limit=615–7 690 000 IU/mL).

Each patient was classified as a function of their response to treatment as measured by the test for assaying the seric viral load of HCV.

A patient was considered to be:
  a patient who was a responder to treatment (patient classified as R), when the viral load of HCV had become undetectable in the patient's blood at the end of treatment and it remained undetectable for 6 months after treatment had been stopped;
  a patient who was a non-responder to treatment (patient classified as NR), when the viral load of HCV remained detectable in the patient's blood at the end of treatment;
  a patient who was a responder-relapser (patient classified as RR), when the viral load of HCV had become undetectable in the patient's blood at the end of treatment, but which became detectable again 6 months after treatment had been stopped.

The viral load of HCV was considered to be undetectable in the patient's blood when the measurement of the HCV RNAs in the serum of patient gave a value of less than 12 International Units (IU) per mL of serum, as measured with the aid of the VERSANT® HCV RNA 3.0 (bDNA) ASSAY kit from Siemens Healthcare Diagnostics as indicated above.

Three sub-populations, or cohorts, were thus formed (sub-population of R patients, sub-population of NR patients and sub-population of RR patients).

2. Comparison of Measurement Values for the Sub-Populations NR and R in Order to Set Up a Multivariate Classification Model The measurement values obtained in §1 above for the sub-populations "responders" (R) and "non-responders" (NR) were compared in order to construct a multivariate classification model which, starting from the combination of these values, classifies the test patient among the patients who have a high probability of responding to anti-HCV treatment (class R) or among the class of patients who have a high probability of not responding to anti-HCV treatment (NR class).

The measurement values obtained at §1 above for the "responders-relapsers" (RR) sub-population were also compared with measurement values obtained for the R and NR sub-populations. It was observed that the RR sub-population was very distinct from that of R; RR patients are primarily classified as R.

A classification model may, for example, be obtained by following a multivariate statistical analysis method or a multivariate mathematical analysis method.

mROC Models:

A suitable multivariate mathematical analysis method is the mROC method (multivariate Receiver Operating Characteristic method).

By using the measurement values obtained in §1 above for the R and NR sub-populations, mROC models were constructed as described in Kramar et al. 1999 and Kramar et al. 2001. To this end, the mROC version 1.0 software, available commercially from the designers (Andrew Kramar, Antoine Fortune, David Farragi and Benjamin Reiser), was used.

Andrew Kramar and Antoine Fortune may be contacted at or via the Unité de Biostatistique du Centre Régional de Lutte contre le Cancer (CRLC) [Biostatistics Unit, Regional Cancer Fighting Centre] Val d'Aurelle—Paul Lamarque (208, rue des Apothicaires; Parc Euromédecine; 34298 Montpellier Cedex 5; France).

David Faraggi and Benjamin Reiser may be contacted at or via the Department of Statistics, University of Haifa (Mount Carmel; Haifa 31905; Israel).

Starting from the input measurement data, the mROC method generates a decision rule in the form of a linear function $[Z=f(BMK_1, BMK_2, BMK_3, \ldots)]$ of the type $Z=\alpha.BMK_1+\beta.BMK_2+\gamma.BMK_3 \ldots$,
where $BMK_1, BMK_2, BMK_3 \ldots$ are the measurement values for the levels of expression of each of the selected genes, and
  the user identifies the reference or threshold value ($\delta$) which provides this combination with the best performance.

This function and this threshold constitute a multivariate classification model.

The function $f$ calculated by the mROC method was then applied to the measurement values of the level of expression of the genes $BMK_1, BMK_2, BMK_3 \ldots$ measured for a test subject p. The value Z calculated for a test subject p was then compared with the threshold $\delta$.

For example, when the mean value of the combination of the levels of expression of said selected genes in the cohort of "R" individuals is lower than that of the cohort of individuals "NR":
  if $Z \geq \delta$, the test is positive: the subject p is declared to be a NR patient (the subject is predicted to be a non-responder to treatment); and
  if $Z < \delta$, the test is negative: the subject p is declared to be a R patient (the subject is predicted to be a responder to treatment).

Conversely, when the mean value of the combination of the levels of expression of said selected genes in the cohort of "R" individuals is higher than that of the cohort of "NR" individuals:

if Z≥δ, the test is negative: the subject p is declared to be a R patient (the subject is predicted to be a responder to treatment); and if Z<δ, the test is positive: the subject p is declared to be a NR patient (the subject is predicted to be a non-responder to treatment).

WKNN Models:

A suitable multivariate statistical analysis method is the WKNN (Weighted k Nearest Neighbours) method.

WKNN models were constructed as described by Hechenbichler and Schliep, 2004 using the measurement values obtained in §1 above for the sub-populations R and NR.

In outline, a WKNN method attributes each new case (y,x) to the class l of maximum weight in a neighbourhood of k neighbours in accordance with the formula:

$$l = max_r \left( \sum_{i=1}^{k} K(D(x, x_{(i)})) I(y_{(i)} = r) \right)$$

where r represents the index of the clinical classes of interest (in fact, sub-population R or sub-population NR), and is equal to 0 or 1.

In order to construct the WKNN models, R software (WKNN library), which is freely available from http://www.r-project.org/, was used. The following control parameters were used:

Kernel (K): biweight;
Parameter of Minkowski distance (D): 2;
Number of neighbours (k): 3;
or
Kernel (K): triweight;
Parameter of Minkowski distance (D): 1;
Number of neighbours (k): 4;
or
Kernel (K): biweight;
Parameter of Minkowski distance (D): 2;
Number of neighbours (k): 3.

The WKNN models constructed in this manner were then used to determine the status, R or NR, of the subjects by inputting the measurement values for these subjects into the WKNN models constructed in this manner.

The measurement values for the levels of expression of the selected genes of a test subject p were compared with those of these neighbours (k). The WKNN model calculates the weight which has to be attributed to the "R sub-population" class and that which has to be attributed to the "NR sub-population" for this subject p. The subject p is then classified by the WKNN model into the major class, for example into the "NR sub-population" class if the weight of the "R sub-population" and "NR sub-population" classes calculated by the WKNN method are 0.3 and 0.7 respectively.

The LOOCV ("Leave-One-Out-Cross-Validation") error is as defined by Hastie, Tibishirani and Friedman, 2009.

Random Forest or RF Models:

Random Forest or RF models were constructed using the measurement values obtained in §1 above for the R and NR sub-populations as described in Breiman in 2001, Liaw and Wiener in 2002.

To this end, R software, which is freely available from http://www.r-project.org/, was used.

The following parameters were used:
NumberOfTrees=500;
NumberOfDescriptors=sqrt(D).

The digital data listed in the output file from R could be used to evaluate the signatures by calculating the following parameters: calculation of the True Positive (TP), False Positive (FP), True Negative (TN) and False Negative (FN) values, see below.

The data extracted from the output file for the RF models constructed thereby had the following form:
"OOB estimate of error rate:
Confusion matrix:

|    | NR | R  | Classification error        |
|----|----|----|-----------------------------|
| NR | TP | FN | NR classification, error rate |
| R  | FP | TN | R classification, error rate  |

ROC score (out-of-bag data): ROC score for predicted samples"

OOB is the acronym for Out-Of-Bag, and represents an evaluation of the error.

These output data directly indicate the values for the parameters TP (number of NR patients who have been classified as NR), FP (number of R patients who have been classified as NR), TN (number of R patients who have been classified as R) and FN (number of NR patients who have been classified as R).

The formulae below can be used to calculate the values for sensitivity (Se), specificity (Spe), positive predictive value (PPV), and negative predictive value (NPV):

Se=TP/(TP+FN);

Sp=TN/(TN+FP);

PPV=TP/(TP+FP);

NPV=TN/(TN+FN).

The output data also directly indicate the error rate and the ROC score of the constructed model.

The RF models constructed in this manner were then used to determine the hepatic fibrosis score of test subjects. The measurement values of the levels of expression of the genes of these test subjects were input into a RF model, which generated output data as presented above and classified the test subject into the "R sub-population" or "NR sub-population" class.

The LOOCV error was as defined by Hastie, Tibishirani and Friedman, 2009.

Neural Network Models

Another appropriate method for multivariate statistical analysis is a neural network method. In brief, a neural network comprises an orientated weighted graph the nodes of which symbolize neurons. The network is constructed from sub-population measurement values (in this case R versus NR) and is then used to determine to which class (in this case R or NR) a new element (in this case a test patient p) belongs.

Neural network models were constructed as described by Intrator and Intrator 1993, Riedmiller and Braun 1993, Riedmiller 1994, Anastasiadis et al. 2005 using the measurement values obtained in §1 above for the R and NR sub-populations; see http://cran.r-project.org/web/packages/neuralnet/index.html.

To this end, R software which is freely available from http://www.r-project.org/, was used (version 1.3 of Neuralnet, written by Stefan Fritsch and Frauke Guenther, following the work by Marc Suling).

The following computation options were used:
"NumberOfHiddenNodes=1 and 2
WeightDecayFactor=0.001
Cross Validate=True
Cross ValidationFolds=5
MaxNumberIterations=2000
MaxNumberWeights=2000".

For each of the combinations, the confusion matrix was extracted in the following format:
"Cross-validation results (5-fold):

| Nodes | Decay | ROC | Score Best |
|---|---|---|---|
| 1 | 1 | | |
| 2 | 2 | | *** |

Contingency Table (best CV model):

| | Predicted | |
|---|---|---|
| Actual | R | NR |
| R | TN | FP |
| NR | FN | TP |

In this example, it will be observed that the best model is model 2, indicated by "***" in the "ScoreBest" column.

These output data directly indicate the values for the parameters TP (number of NR patients who have been classified as NR), FP (number of R patients who have been classified as NR), TN (number of R patients who have been classified as R) and FN (number of NR patients who have been classified as R).

The following parameters were evaluated: the sensitivity (Se), the specificity (Spe), the positive predictive value (PPV) and the negative predictive value (NPV) (see formulae for Se, Spe, PPV and NPV above).

The ROC score was extracted directly from the output file on the line identified by "***" which corresponded to the best model. The error was calculated by the following formula:

$$\text{Class\_err}=(FP+FN)/(FP+TP+FN+TN).$$

The neural network models constructed thereby were then used to determine whether a test subject had a high probability of responding or, in contrast, of not responding to anti-HCV treatment. The measurement values for the levels of expression of the genes of these test subjects were entered into a neural network model which generated output data as presented above and classified the test subject into the "R sub-population" or "NR sub-population" class.

3. Examples of Classification Models Obtained:

The inventors have thus identified the genes for which the levels of expression constitute biomarkers which, when taken in combination, are pertinent to determining the status of "responder" (R) or "non-responder" (NR) of a subject.

These genes are the following seventeen genes MBL2, LGALS3BP and IL8, G1P2, CXCL10, CCL21, AFP, CRP, CXCL11, CXCL6, CXCL9, FGF7, MDK, MMP2, SFN, TGFB2 and VEGFD.

Particularly advantageously, it may be observed that these seventeen genes are all genes coding for non-membrane proteins, i.e. genes which code for a protein with an intracellular and/or extracellular location and which is thus susceptible of being detected in a biological fluid of the subject such as the blood, the serum or the plasma.

The inventors have further identified that the most pertinent combinations comprise:
at least one gene from among MBL2, LGALS3BP and IL8; and
at least one gene from among G1P2, CCL21 and CXCL10; and
optionally, at least one gene from among AFP, CRP, CXCL11, CXCL6, CXCL9, FGF7, MDK, MMP2, SFN, TGFB2 and VEGFD.

By way of illustration, examples of appropriate combinations of biomarkers in particular comprise combinations of two, three or five biomarkers (combinations of the levels of expression of two, three or five genes) presented in Tables 2, 7 and 12 above, in the description section.

Examples of classification models which may be used with these combinations of biomarkers are presented in:
Tables 3 and 4 to 6 above (combination of the levels of translation of two selected genes in accordance with the invention),
Tables 8 and 9 to 11 above (combination of the levels of translation of three selected genes in accordance with the invention),
Tables 13 and 14 to 16 above (combination of the levels of RNA transcripts of selected genes in accordance with the invention),
Tables 17 and 18 to 20 above (combination of the levels of translation of selected genes in accordance with the invention),
Tables 21 and 22 to 24 above (combination of the levels of RNA transcripts of selected genes in accordance with the invention, further combined with other factors),
Tables 25 and 26 to 28 above (combination of the levels of translation of selected genes in accordance with the invention, further combined with other factors);
see also the Examples below.

The predictive combinations of the invention are combinations of the levels of gene expression selected as indicated above.

However, it may be elected to involve one or more factors in these combinations other than the levels of expression of these genes, in order to combine this or these other factors and the levels of expression of the selected genes into one decision rule.

This or these other factors are preferably selected so as to construct a classification model the predictive power of which is further improved compared with the model which did not comprise this or these other factors.

This or these other factors may, for example, be clinical, biological, or virological factors, for example:
one or more clinical factors, such as sex (feminine F or masculine M), age at the date of sampling (for example, age at the date of HBP, age at the date of hepatic cytopuncture, age at the date of sampling blood, serum, plasma or urine), age at the date of contamination, age at the treatment start date, body mass index (BMI), insulin sensitivity index (HOMA), diabetes, alcohol consumption, degree of steatosis, mode of contamination, Metavir activity, or hepatic fibrosis score measured using the Metavir system (Metavir F score) or using the Ishak system, and/or
- one or more biological factors other than the levels of expression of said selected genes, such as concentration of haptoglobin (Hapto), concentration of apolipoprotein A1 (ApoA1), total quantity of bilirubin (BLT), concentration of gamma glutamyl transpeptidase (GGT), concentration of aspartate aminotransferase (AST), concentration of alanine aminotransferase (ALT), platelet count (PLQ), quantity of prothrombin (TP), quantity of HDL cholesterol (Chol-HDL), total quantity of cholesterol, concentration of ferritin (Ferritin), level of glycaemia (glycaemia), concentration of peptide C, quantity of insulin (insulinaemia), concentration of triglycerides (TG), quantity of albumin, transferrin saturation (TSAT), or concentration of alkaline phosphatase (ALP);

and/or
- one or more virological factors, such as viral genotype, duration of infection, viral load before treatment (VL-beforeTTT), viral load assayed for the patient at the treatment start date (viral load at D0), viral load assayed for the patient at the date of sampling (viral load at HBP, viral load at the date of hepatic cytopuncture, or viral load at the date of sampling blood, serum, plasma or urine).

Example 2

RNA from Hepatic Biopsy Puncture (HBP)/Applications to Test Patients

2a) Example of Application of the Combination of the Levels of Expression (RNA) of the Genes MBL2, G1P2, LGALS3BP, TGFB2 and CRP (Combination No. 1 in Table 12 Above):

Using the WKNN method (see Example 1 above), the LOOCV error associated with the combination of the levels of transcription (RNA) of the genes MBL2, G1P2, LGALS3BP, TGFB2 and CRP (combination No. 1 in Table 12 above) is 12 (see Table 13 above).

The best performances for this combination using the WKNN method (computed over the population of responders (R) and non-responders (NR) of Example 1 (n=107 patients; see Table 33 above)) are as follows:

sensitivity (Se)=82%; specificity (Sp)=92% (see Table 13 above).

The model parameters used for the WKNN method were as follows:
Kernel (K): biweight
Parameter of Minkowski distance (D): 2
Number of neighbours (k): 3

Using this model, 71% of responder-relapsers (RR) were classified as responders (R) and 29% as non-responders (NR).

An example of a prediction over 20 subjects (human patients) is given in Table 37 below, which presents the measurement values for the levels of expression of the selected genes (BMK values obtained by the $2^{-\Delta Ct}$ method; see Example 1 above).

One or more clinical, biological and virological factors may be combined with the five biomarkers indicated above (levels of expression of five genes), and give rise to a decision rule the predictive power of which is even better than that of the rule presented above.

The following Tables 38 to 40 present Examples of such clinical, biological and virological factors, as well as their values for the test subjects of Table 37.

ND=not determined

TABLE 37

Example of application of a classification model based on the combination of the levels of expression of the genes MBL2, G1P2, LGALS3BP, TGFB2 and CRP (combination No. 1 of Table 12 above)

| No. of test subject | MBL2 | G1P2 | LGALS3BP | TGFB2 | CRP | WKNN model (kernel = biweighted; parameter of Minkowski distance = 2; k = 3) WKNN prediction | Status, R or NR, as determined after treatment |
|---|---|---|---|---|---|---|---|
| 59 | 0.99 | 0.88 | 0.04 | 1.74 | 1.39 | R | R |
| 65 | 2.30 | 1.61 | 0.05 | 0.23 | 0.87 | R | R |
| 75 | 5.48 | 8.66 | 0.27 | 1.40 | 0.11 | NR | NR |
| 83 | 0.01 | 6.17 | 0.16 | 1.17 | 0.64 | NR | NR |
| 90 | 2.02 | 1.91 | 0.05 | 0.52 | 0.63 | R | R |
| 91 | 0.89 | 0.66 | 0.02 | 2.18 | 0.60 | R | R |
| 92 | 0.62 | 0.05 | 0.01 | 0.28 | 1.75 | R | R |
| 125 | 1.42 | 1.26 | 0.01 | 0.64 | 0.20 | R | R |
| 167 | 0.53 | 5.05 | 0.10 | 3.22 | 3.81 | NR | NR |
| 308 | 1.19 | 6.66 | 0.25 | 1.57 | 1.64 | NR | NR |
| 346 | 4.00 | 0.60 | 0.13 | 1.89 | 337.77 | R | R |
| 366 | 2.90 | 0.16 | 0.01 | 1.00 | 2.92 | R | R |
| 501 | 1.22 | 1.42 | 0.03 | 0.14 | 3.86 | R | R |
| 503 | 1.32 | 0.76 | 0.02 | 0.30 | 2.85 | R | R |
| 509 | 0.02 | 6.13 | 0.04 | 1.24 | 0.26 | NR | NR |
| 521 | 0.00 | 4.36 | 0.58 | 12.17 | 0.34 | NR | NR |
| 526 | 3.14 | 5.26 | 0.13 | 1.28 | 2.13 | NR | NR |
| 527 | 1.22 | 9.32 | 0.46 | 1.62 | 1.31 | NR | NR |
| 573 | 4.50 | 6.89 | 0.13 | 1.31 | 0.35 | NR | NR |
| 574 | 4.23 | 4.96 | 0.24 | 3.82 | 1.99 | NR | NR |

TABLE 38

(Clinical data):

| No. of subject | Sex | age at HBP | BMI (kg/m²) | Insulin sensitivity index (HOMA) | Diabetes | Alcohol consumption (g/day) | degree of steatosis | Mode of contamination | Metavir activity | Ishak fibrosis score | Metavir fibrosis score | Age at start of treatment (yrs) |
|---|---|---|---|---|---|---|---|---|---|---|---|---|
| 59 | F | 50.9 | 23.7 | 1.5 | No | 0 | 0 | Transfusion | 1 | 2 | 1 | 51.3 |
| 65 | M | 35.6 | 29.6 | 3.9 | No | 0 | 0 | Endemic area | 1 | 2 | 1 | 35.7 |
| 75 | F | 53.0 | 27.9 | ND | No | 0 | 0 | ND | 2 | 2 | 2 | 53.3 |
| 83 | F | 51.4 | 25.7 | ND | No | ND | 2 | ND | 1 | 2 | 1 | 52.0 |
| 90 | F | 58.7 | 25.2 | ND | No | 0 | 2 | Transfusion | 1 | 3 | 2 | 59.0 |
| 91 | F | 47.8 | 21.4 | ND | No | 0 | 0 | ND | 1 | 2 | 1 | 48.0 |
| 92 | M | 35.1 | 28.7 | ND | No | 0 | 0 | Toxicomania | 1 | 3 | 2 | 35.8 |
| 125 | M | 27.4 | 22.6 | 1.4 | No | 0 | 0 | ND | 1 | 1 | 1 | 27.6 |
| 167 | F | 48.6 | 37.8 | 2.3 | No | ND | 0 | Transfusion | 2 | 2 | 1 | 48.8 |
| 308 | M | 34.9 | 27.7 | ND | No | 0 | 0 | Endemic area | 1 | 1 | 1 | 35.4 |
| 346 | F | 50.4 | 17.8 | ND | No | 30 | 0 | ND | 1 | 3 | 2 | 50.6 |
| 366 | M | 42.8 | 28.6 | ND | No | 10 | 1 | Toxicomania | 1 | 3 | 2 | 43.6 |
| 501 | M | 47.7 | 33.1 | 4.8 | No | 0 | 2 | Endemic area | 1 | 4 | 2 | 47.8 |
| 503 | F | 55.0 | 21.6 | 1.0 | No | 0 | 0 | Transfusion | 0 | 4 | 2 | 55.1 |
| 509 | F | 48.2 | 20.8 | 1.4 | No | ND | 0 | Transfusion | 1 | 4 | 3 | 48.4 |
| 521 | M | 58.4 | 23.8 | ND | No | 30 | 0 | Transfusion | 1 | 4 | 3 | 58.9 |
| 526 | F | 73.0 | 24.8 | ND | No | 0 | 1 | Transfusion | 2 | 6 | 4 | 73.2 |
| 527 | M | 47.4 | 37.3 | ND | No | 20 | 1 | Toxicomania | 1 | 5 | 3 | 48.2 |
| 573 | M | 46.6 | 25.5 | ND | No | 0 | 2 | Toxicomania | 2 | 2 | 1 | 47.7 |
| 574 | M | 58.3 | 23.6 | ND | No | 0 | 1 | Nosocomial | 1 | 3 | 2 | 60.0 |

TABLE 39

(Virological data):

| Patient No. | Viral genotype | Duration of infection (years) | viral load at HBP (copies/mL ·10³) | viral load at start of treatment (copies/mL ·10³) |
|---|---|---|---|---|
| 59 | 5 | 26.8 | 524 | 1120 |
| 65 | 4 | ND | 1135 | 450 |
| 75 | 1 | ND | 3276 | 2347 |
| 83 | 1 | ND | 1579 | 3928 |
| 90 | 1 | ND | 515 | 515 |
| 91 | 1 | ND | 3902 | 3902 |
| 92 | 1 | 16.1 | 3.2 | 3.2 |
| 125 | 4 | ND | 695 | 695 |
| 167 | 4 | ND | 12616 | 12616 |
| 308 | 4 | ND | 423 | 423 |
| 346 | 3 | ND | 6 | 6 |
| 366 | 4 | 25.0 | 4700 | 7573 |
| 501 | 4 | ND | 750 | 750 |
| 503 | 1 | 24.0 | 566 | 843 |
| 509 | 1 | 49.1 | 8779 | 8779 |
| 521 | 1 | 34.8 | 14654 | 14432 |
| 526 | 1 | 38.4 | 778 | 778 |
| 527 | 1 | 20.4 | ND | 3457 |
| 573 | 1 | 25.9 | ND | 8419 |
| 574 | 1 | 47.0 | ND | 13034 |

TABLE 40

(Biological data):

| Subject No. | A2M (g/L) | Hapto (g/L) | Apo A1 (g/L) | BLT (μmol/L) | GGT (U/L) | AST (U/L) | ALT (U/L) | PLQ (×10³/mm³) | PT (%) | Chol-HDL (mmole/L) |
|---|---|---|---|---|---|---|---|---|---|---|
| 59 | 2.3 | 0.97 | 2.04 | 20 | 18 | 49 | 80 | 239 | 100 | 2.13 |
| 65 | 4.07 | 1.15 | 1.17 | 8 | 46 | 61 | 152 | 210 | 92 | 0.72 |
| 75 | ND | ND | ND | 12 | 135 | 64 | 50 | 233 | 100 | 2.15 |
| 83 | ND | ND | ND | 13 | 82 | 78 | 95 | 232 | 101 | ND |
| 90 | ND | ND | ND | 11 | 21 | 61 | 119 | 359 | 100 | ND |
| 91 | ND | ND | ND | 9 | 39 | 64 | 79 | 353 | 99 | ND |
| 92 | ND | ND | ND | 12 | 92 | 29 | 128 | 355 | 106 | 0.9 |
| 125 | 1.15 | 0.64 | 1.45 | 16 | 47 | 23 | 47 | 229 | 99 | 1.16 |
| 167 | 2.9 | 0.54 | 1.64 | 15 | 378 | 163 | 144 | 183 | 78 | 1.28 |
| 308 | ND | ND | ND | 16 | 246 | 30 | 36 | 214 | 100 | ND |
| 346 | ND | ND | ND | 12 | 23 | 27 | 41 | 217 | 95 | 1.32 |

TABLE 40-continued

| (Biological data): | | | | | | | | | |
|---|---|---|---|---|---|---|---|---|---|
| 366 | 1.31 | 0.37 | 1.06 | 15 | 29 | 40 | 105 | 226 | 98 | ND |
| 501 | 3.29 | 1.02 | 1.18 | 13 | 49 | 82 | 185 | 195 | 100 | 0.98 |
| 503 | 4.05 | 0.48 | 1.62 | 9 | 16 | 81 | 100 | 200 | 81 | 1.38 |
| 509 | 4.24 | 0.39 | 1.89 | 13 | 43 | 154 | 243 | 121 | 86 | 1.88 |
| 521 | ND | ND | ND | 11 | 127 | 83 | 166 | 189 | 100 | 1.62 |
| 526 | ND | ND | ND | 17 | 172 | 128 | 210 | 187 | 77 | ND |
| 527 | ND | ND | ND | 16 | 127 | 35 | 80 | 182 | 100 | ND |
| 573 | ND | ND | ND | 21 | 249 | 61 | 88 | 157 | 100 | ND |
| 574 | ND | ND | ND | 13 | 67 | 62 | 87 | 215 | 100 | ND |

| Subject No. | ferritin (µg/L) | glycaemia (mmole/L) | peptide C (ng/mL) | insulin (µUI/mL) | TG (mmole/L) | albumin (g/L) | TSAT (%) | Total cholesterol (mmole/L) | ALP (U/L) |
|---|---|---|---|---|---|---|---|---|---|
| 59 | 30 | 5 | 2.18 | 6.65 | 0.71 | 46 | 27 | 5.46 | 77 |
| 65 | 147 | 5.2 | 3.31 | 17.07 | 1.09 | 46 | 43 | 3.82 | 49 |
| 75 | 271 | 5.4 | ND | ND | 0.69 | 44 | 40 | 4.72 | 149 |
| 83 | 71 | 5.6 | ND | ND | 0.76 | 44 | 37 | 3.68 | 97 |
| 90 | 137 | 4.2 | ND | ND | 0.88 | 48 | 42 | 5.4 | 52 |
| 91 | 206 | 4.7 | ND | ND | 1 | 43 | 36 | 4.5 | 72 |
| 92 | 133 | 5.4 | ND | ND | 0.81 | 48 | 22 | 4.26 | 68 |
| 125 | 97 | 5.2 | 1.67 | 5.91 | 0.57 | 48 | 33 | 4.14 | 43 |
| 167 | 702 | 5.22 | 2.3 | 9.82 | 0.62 | 43 | 70 | 4.58 | 114 |
| 308 | 455 | 5.1 | ND | ND | 1.13 | 48 | 46 | 4.81 | 73 |
| 346 | ND | 5.28 | ND | ND | 0.51 | 39 | 4 | 5.47 | 43 |
| 366 | 166 | 5.4 | ND | ND | 1.21 | 47 | 36 | 5.81 | 54 |
| 501 | 583 | 5.5 | 3.17 | 19.7 | 0.75 | 48 | 26 | 3.84 | 60 |
| 503 | 140 | 4.8 | 1.39 | 4.55 | 0.78 | ND | 46 | 5.43 | 53 |
| 509 | 179 | 4.3 | 2.8 | 7.5 | 0.56 | 48 | 32 | 4.02 | 56 |
| 521 | 514 | 6.2 | ND | ND | 1.76 | 47 | 32 | 4.62 | 62 |
| 526 | 320 | 4.4 | ND | ND | 0.7 | 41 | 35 | 4.33 | 108 |
| 527 | 148 | 5.7 | ND | ND | 0.68 | 48 | 16 | 3.67 | 67 |
| 573 | 296 | 5.5 | ND | ND | 0.96 | 47 | 43 | 4.97 | 40 |
| 574 | 337 | ND | ND | ND |  | 47 | 27 | ND | 67 |

2b) Example of Application of the Combination of the Levels of Expression (RNA) of the Genes MDK, LGALS3BP, CXCL10, IL8 and CCL21 (Combination No. 24 in Table 12 Above):

The AUC relative to the combination of the levels of expression of the genes MDK, LGALS3BP, CXCL10, IL8 and CCL21 (combination No. 24 in Table 12 above) calculated for the population of responders (R) and non-responders (NR) of Example 1 (n=107 patients; see Table 33 above) is 0.771 (see Table 16 above).

Using the mROC method (see Example 1), the maximizing threshold of the Youden's index ($\delta$) for this combination is −2.309 (see Table 14 above).

For this choice of threshold, the performances of the combination are as follows:
Sensitivity (Se)=73%; specificity (Spe)=74% (see Table 13 above).
The following rule is an example of a decision rule:

$$Z = 0.359 \times CCL21^t + 0.028 \times CXCL10^t + 0.055 \times IL8 + 0.107 \times LGALS3BP^t + 0.22 \times MDK^t$$

(Function Z24ARN; see Table 14 above), where:
MDK, LGALS3BP, CXCL10, IL8 and CCL21 are the measurement values for the levels of expression of the indicated genes (values obtained by the $2^{-\Delta Ct}$ method; see Example 1 above), and
where
the exponent t (carried here by CCL21, CXCL10, LGALS3BP and MDK) indicates that the value to be applied in the decision rule is the Box-Cox transformation (Box and Cox, 1964) of the measurement value (BMK) of the level of expression of the gene under consideration in order to normalize it using the following formula:

$$BMK^t = (BMK^\lambda - 1)/\lambda.$$

If Z≥−2.309: the diagnostic test is positive (mROC prediction=1), the subject is declared "NR" (subject predicted to be a non-responder to treatment).

If Z<−2.309: the test is negative (mROC prediction=0), the subject is declared "R" (subject predicted to be a responder to treatment).

In accordance with this model, 62% of the responders-relapsers (RR) were classified among the responders (R) and 38% were classified among the non-responders (NR).

An example of a prediction over 20 subjects (human patients) is given in Table 41 below, which presents the measurement values for the levels of expression of the selected genes (BMK values obtained by the $2^{-\Delta Ct}$ method; see Example 1 above).

One or more clinical, biological and virological factors may be combined with the five markers indicated above (levels of expression of five genes), and lead to a decision rule the predictive power of which is even better than that of the rule presented above.

Tables 38 to 40 above present Examples of such clinical, biological and virological factors, as well as their values for the test patients of Table 41.

TABLE 41

Example of application of a classification model based on the combination of the levels of expression of the genes MDK, LGALS3BP, CXCL10, IL8 and CCL21 (combination No. 24 of Table 12 above)

| No. of test subject | mROC model (function Z24ARN; δ = −2.309) | | | | | | mROC prediction | Status, R or NR, as determined after treatment |
|---|---|---|---|---|---|---|---|---|
| | MDK | LGALS3BP | CXCL10 | IL8 | CCL21 | Z | | |
| 59 | 0.090 | 0.045 | 0.010 | 0.329 | 0.006 | −2.625 | R | R |
| 65 | 0.105 | 0.048 | 0.060 | 0.168 | 0.012 | −2.370 | R | R |
| 75 | 1.248 | 0.265 | 0.550 | 0.908 | 0.033 | −1.246 | NR | NR |
| 83 | 0.476 | 0.164 | 0.180 | 0.231 | 0.073 | −1.303 | NR | NR |
| 90 | 0.115 | 0.048 | 0.080 | 0.089 | 0.012 | −2.359 | R | R |
| 91 | 0.051 | 0.023 | 0.110 | 0.040 | 0.008 | −2.717 | R | R |
| 92 | 0.001 | 0.008 | 0.030 | 0.087 | 0.005 | −3.496 | R | R |
| 125 | 0.058 | 0.012 | 0.020 | 0.000 | 0.005 | −2.962 | R | R |
| 167 | 0.521 | 0.099 | 0.080 | 0.923 | 0.018 | −1.801 | NR | NR |
| 308 | 0.446 | 0.251 | 0.070 | 0.853 | 0.022 | −1.650 | NR | NR |
| 346 | 0.032 | 0.133 | 0.020 | 0.182 | 0.004 | −2.800 | R | R |
| 366 | 0.012 | 0.015 | 0.050 | 0.179 | 0.009 | −2.927 | R | R |
| 501 | 0.046 | 0.032 | 0.130 | 0.601 | 0.016 | −2.411 | R | R |
| 503 | 0.014 | 0.024 | 0.010 | 0.109 | 0.004 | −3.144 | R | R |
| 509 | 0.172 | 0.045 | 0.220 | 1.157 | 0.025 | −1.964 | NR | NR |
| 521 | 1.676 | 0.576 | 0.490 | 3.732 | 0.052 | −0.784 | NR | NR |
| 526 | 0.189 | 0.130 | 0.170 | 2.370 | 0.028 | −1.716 | NR | NR |
| 527 | 0.276 | 0.457 | 0.070 | 0.657 | 0.045 | −1.453 | NR | NR |
| 573 | 0.047 | 0.134 | 0.400 | 0.323 | 0.028 | −2.037 | NR | NR |
| 574 | 0.191 | 0.241 | 1.040 | 5.756 | 0.031 | −1.378 | NR | NR |

2c) Combination of the Levels of Expression (RNA) of the Genes MDK, LGALS3BP, CXCL10, IL8 and CCL21 (Combination No. 24 in Table No. 12 Above), Further Combined with Clinical Factors and/or to Other Biological Factors and/or Virological Factors:

One or more clinical factors and/or one or more biological factors and/or one or more virological factors may be combined with the levels of expression of the genes selected in accordance with the invention (in fact, levels of RNA transcription assayed in a HBP sample), and thus lead to a decision rule the predictive power of which is even better than that of just the combination of said levels of expression.

For example, the combination:
of the levels of expression (RNA) of the genes MDK, LGALS3BP, CXCL10, IL8 and CCL21 (combination No. 24 in Table 12 above; see Example 2b above), and
of the value for another biological factor, namely the concentration of alkaline phosphatase (ALP), and
of a virological factor value, namely the viral load before the start of treatment (VLbeforeTTT),
leads to a decision rule the area under the ROC curve (AUC) of which, calculated over the set of patients of the study population of Example 1 for whom the data for ALP and VLbeforeTTT were available (n=97 patients), is 0.827 (see Table 24 above), while it is 0.771 (see Table 16 above), when the combination of the levels of expression of the genes MDK, LGALS3BP, CXCL10, IL8 and CCL21 is used alone, without being combined with this biological factor and this virological factor.

Using the mROC method (see Example 1), the maximizing threshold of the Youden's index for this combination is 5.454 (see Table 22 above).

For this choice of threshold, the performances of the combination are as follows:

Sensitivity (Se)=81%; specificity (Spe)=71% (see Table 21 above).

The following rule is an example of a decision rule:

$$Z = -0.051 \times CXCL10^t + 0.032 \times IL8^t + 0.357 \times CCL21^t + 0.189 \times MDK^t + 0.182 \times LGALS3BP^t + 0.052 \times VLbeforeTTT^t + 2.644 \times PAL^t$$

(function Z24ARNsupp; see Table 22 above), where:
MDK, LGALS3BP, CXCL10, IL8, CCL21 are the measurement values for the levels of expression of the indicated genes (values obtained by the $2^{-\Delta Ct}$ method; see Example 1 above), VLbeforeTTT and ALP are the values for the virological factor and the biological factor indicated above (viral load VLbeforeTTT in copies/mL·$10^3$, and concentration, ALP, in IU/mL), and where the exponent t (carried here by CXCL10, CCL21, LGALS3BP, MDK, VLbeforeTTT and ALP) indicates that the value to be applied in the decision rule (function Z24ARNsupp) is the Box-Cox transformation (Box and Cox, 1964) of the measurement value for the biomarker BMK under consideration, in order to normalize it using the following formula:

$$BMK^t = (BMK^\lambda - 1)/\lambda.$$

In the example of the decision rule indicated above, the parameters λ are 0.04 for CXCL10; 0.02 for CCL21; −0.07 for LGALS3BP; 0.15 for MDK; 0.2 for VLbeforeTTT; and −0.26 for ALP (see Table 13 above).

If Z≥5.454: the diagnostic test is positive (mROC prediction=1), the subject is declared "NR".

If Z<5.454: the test is negative (mROC prediction=0), the subject is declared "R".

Using this model, 56% of the responder-relapsers (RR) were classified among the responders (R) and 44% were classified among the non-responders (NR).

Example 3

Seric Proteins (Combination of the Levels of Expression of 5 Genes)

The levels of expression of the proteins CXCL10, LGALS3BP, IL8, CCL21 and MDK (combination No. 24 in Table 12 above) were measured in the serum of 167 patients. Protein measurements were carried out as described in Example 1 and Table 44 above.

This group of 167 patients was constituted as follows:
67 patients, for whom a serum sample was available, were selected using the same inclusion and exclusion criteria as the 140 patients described in Table 30 above and were added to this group of 140 patients;
From among the 207 patients thus collected together, patients responding to treatment (status R) or patients not responding to treatment (status NR) were selected for whom all clinical, biological and virological data were available,
which resulted in a group of 167 patients (see Table 45 above).

From among these 167 patients:
90 of them were shown to be responders to treatment (status R);
77 of them were shown to be non-responders to treatment (status NR).

Using the mROC method (see Example 1), the maximizing threshold of the Youden's index ($\delta$) for this combination is 2.231 (see Table 18 above).

For this choice of threshold, the performances of the combination are as follows:
Sensitivity (Se)=82%; specificity (Spe)=74% (see Table 17 above).

The following rule is an example of a decision rule:

$$Z = 0.025*CXCL10^t + 0.071*IL8^t + 0.465*LGALS3BP^t - 0.001*CCL21^t - 0.341*MDK$$

(Function Z24PROT; see Table 18 above), where CXCL10, LGALS3BP, IL8, CCL21 and MDK are the measurement values for the biomarkers BMK, i.e. the measurement values for the levels of expression of the indicated genes (in fact, seric protein concentration), and where the exponent t (carried here by CXCL10, LGALS3BP, IL8 and CCL21) indicates that the value to be applied in the decision rule is the Box-Cox transformation (Box and Cox, 1964) of the mea-

TABLE 45

Clinical, biological and virological data

| Clinical, biological and virological data | Patients | NR patients | R patients |
|---|---|---|---|
| n | 167 | 77 | 90 |
| Sex: male (%)/female (%) | 107 (64)/60 (36) | 51 (66)/26 (34) | 56 (62)/34 (38) |
| Age [mean ± standard deviation (range)] | 48.1 ± 9.5 (27-73) | 48.7 ± 8.9 (32-73) | 47.5 ± 10 (27-71) |
| Source of infection [n (%)] | | | |
| blood transfusion | 27 (16.2) | 9 (11.7) | 18 (20) |
| intravenous administration of a drug | 58 (34.7) | 30 (38.4) | 28 (31.1) |
| unknown | 82 (49.1) | 38 (49.9) | 44 (48.9) |
| Alanine aminotransferase (ALT) IU/L [mean ± standard deviation (range)] | 124 ± 92 (20-520) | 120 ± 78 (20-397) | 127 ± 103 (20-520) |
| HCV genotypes [n (%)] | | | |
| 1 | 98 (58.7) | 63 (81.8) | 35 (38.9) |
| 2 | 13 (7.8) | 0 (0) | 13 (14.4) |
| 3 | 21 (12.6) | 2 (2.6) | 19 (21.1) |
| 4 | 34 (20.3) | 12 (15.6) | 22 (24.4) |
| 5 | 1 (0.6) | 0 (0) | 1 (1.1) |
| Fibrosis score (Metavir F score) [n (%)] | | | |
| 0 | 2 (1.2) | 1 (1.29) | 1 (1.1) |
| 1 | 50 (29.94) | 14 (18.18) | 36 (40) |
| 2 | 58 (34.73) | 25 (32.47) | 33 (36.7) |
| 3 | 26 (15.57) | 15 (19.48) | 11 (12.2) |
| 4 | 29 (17.37) | 20 (25.97) | 9 (10) |
| unknown | 2 (1.2) | 2 (2.6) | 0 (0) |

Figure 1B:
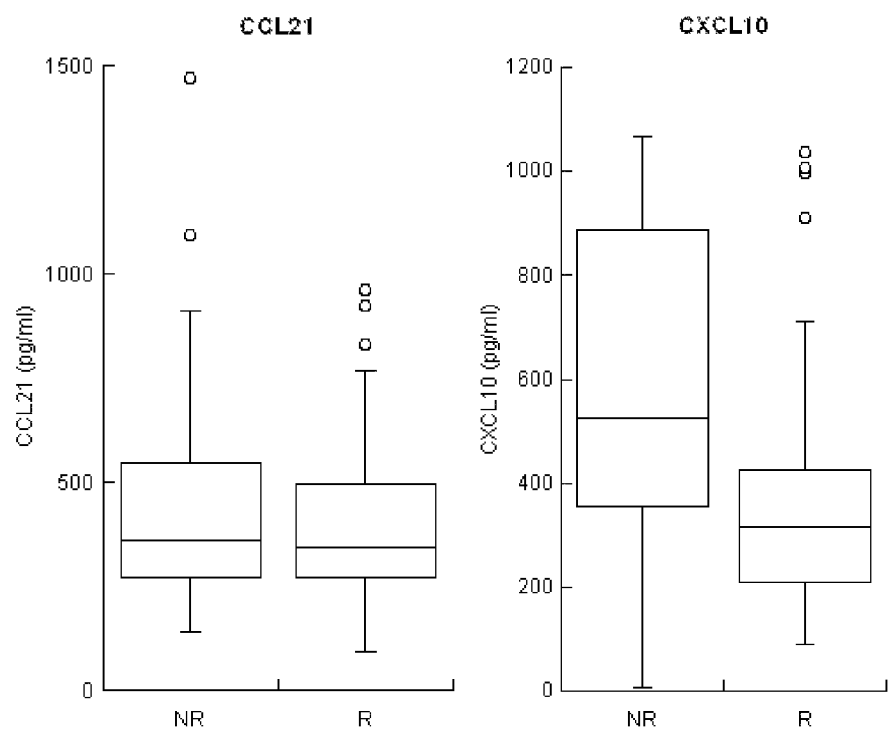

The distribution of the seric concentrations of the proteins CXCL10, LGALS3BP, IL8, CCL21 and MDK as a function of the status, R or NR, of the patient is presented in FIGS. 1A and 1B.

3a) Example of a Multivariate Classification Model Starting from the Combination of the Levels of Seric Expression of the Proteins CXCL10, LGALS3BP, IL8, CCL21 and MDK (Combination No. 24 in Table 12 Above):

The AUC relative to the combination of the levels of expression of the genes CXCL10, LGALS3BP, IL8, CCL21 and MDK (combination No. 24 in Table 12 above) calculated for the complete study population of Example 3 (n=167 patients) is 0.838 (see Table 20 above).

surement value of the level of expression of the gene under consideration, in order to normalize it using the following formula:

$$BMK^t = (BMK^\lambda - 1)/\lambda.$$

In the example of the decision rule indicated above, the parameters $\lambda$ are 0.41 for CXCL10, 0.33 for LGALS3BP, 0.23 for IL8 and −0.01 for CCL21 (see Table 19 above).

If $Z \geq 2.231$: the diagnostic test is positive (mROC prediction=1), the subject is declared "NR" (subject predicted to be a non-responder to treatment), If $Z < 2.231$: the test is negative (mROC prediction=0), the subject is declared "R" (subject predicted to be a responder to treatment).

An example of a prediction for 20 subjects (human patients) is given in Table 42 below, which presents the measurement values (BMK) of the levels of seric expression of the selected genes.

One or more clinical factors and/or one or more biological factors and/or one or more virological factors may be combined with the levels of seric expression of the selected proteins in accordance with the invention, and lead to a decision rule the predictive power of which may be even better than that for the above rule (see Example 1; see Example 3b below).

TABLE 42

Example of application of a classification model based on the combination of the levels of seric expression of the genes CXCL10, LGALS3BP, IL8, CCL21 and MDK (combination No. 24 of Table 12 above)

| No. of test subject | MDK (ng/mL) | IL8 (pg/mL) | LGALS3BP (µg/mL) | CXCL10 (ng/mL) | CCL21 (pg/mL) | Z score | mROC prediction | Status, R or NR, as determined after treatment |
|---|---|---|---|---|---|---|---|---|
| 6 | 0.096 | 8.6 | 16.84 | 573.0 | 720.6 | 3.090 | NR | NR |
| 45 | 0.080 | 13.8 | 2.09 | 268.3 | 581.7 | 1.154 | R | R |
| 58 | 1.351 | 9.5 | 14.77 | 437.7 | 585.1 | 2.437 | NR | NR |
| 59 | 0.188 | 14.9 | 5.15 | 137.9 | 346.0 | 1.605 | R | R |
| 62 | 0.665 | 7.1 | 8.87 | 422.0 | 507.2 | 2.097 | R | R |
| 65 | 0.325 | 14.8 | 5.24 | 711.2 | 368.8 | 2.014 | R | R |
| 66 | 0.398 | 23.3 | 3.07 | 560.7 | 305.3 | 1.575 | R | R |
| 73 | 0.217 | 13.5 | 4.15 | 330.1 | 391.5 | 1.613 | R | R |
| 75 | 1.018 | 31.0 | 23.76 | 1036.3 | 372.8 | 3.608 | NR | NR |
| 80 | 0.137 | 10.3 | 11.73 | 1068.4 | 283.7 | 2.936 | NR | NR |
| 83 | 0.184 | 17.4 | 13.11 | 1036.3 | 384.1 | 3.093 | NR | NR |
| 86 | 1.110 | 8.4 | 8.99 | 174.8 | 373.2 | 1.756 | R | R |
| 90 | 0.399 | 1.9 | 6.6 | 393.1 | 285.0 | 1.771 | R | R |
| 91 | 0.956 | 20.6 | 3.04 | 399.2 | 443.0 | 1.252 | R | R |
| 92 | 0.145 | 7.5 | 1.88 | 168.9 | 387.3 | 0.893 | R | R |
| 145 | 0.313 | 9.8 | 11.61 | 203.4 | 578.8 | 2.333 | NR | NR |
| 167 | 0.245 | 13.7 | 10.73 | 708.4 | 498.2 | 2.677 | NR | NR |
| 308 | 0.489 | 14.2 | 10.63 | 304.7 | 306.4 | 2.327 | NR | NR |
| 509 | 0.145 | 41.8 | 15.45 | 911.4 | 665.8 | 3.368 | NR | NR |
| 512 | 0.392 | 25.1 | 6.82 | 911.4 | 548.1 | 2.381 | NR | NR |

3b) Combination of Levels of Expression in the Serum of the Genes CXCL10, IL8, LGALS3BP, CCL21 and MDK (Combination No. 24 in Table 12 Above), Further Combined with a Clinical Factor and Biological Factors:

One or more clinical factors and/or one or more biological factors (other than the level of expression of genes selected in accordance with the invention) and/or one or more virological factors may be combined with the levels of seric expression of genes selected in accordance with the invention (seric proteins), and thus lead to a decision rule the predictive power of which is even better than that of a combination of said levels of seric expression alone.

As an example, the combination:
of the levels of seric translation of the genes CXCL10, IL8, LGALS3BP, CCL21 and MDK (see Example 3a below; combination No. 24 in Table 12 above), and
of the values for the following (other) biological factors:
concentration of gamma glutamyl transpeptidase (GGT),
concentration of alkaline phosphatase (ALP); and
of the value for the following virological factor:
viral load before treatment (VLbeforeTTT),
leads to a decision rule the area under the ROC curve (AUC) of which, computed for the complete study population of Example 3 (n=167 patients), is 0.872 (see Table 28 above), while it is 0.838 (see Table 20 above) when the combination of the levels of expression of the genes MDK, LGALS3BP, CXCL10, CCL21 and IL8 is used alone, without being combined with the (other) biological factors and/or virological factor indicated above.

Using the mROC method (see Example 1), the maximizing threshold of the Youden's index for this combination is 4.516 (see Table 26 above).

For this choice of threshold, the performances of the combination are as follows:

Sensitivity (Se)=82%; specificity (Spe)=77% (see Table 25 above).

The following rule is an example of a decision rule:

$$Z = -0.353 \times MDK + 0.059 \times IL8^t + 0.456 \times LGALS3BP^t + 0.010 \times CXCL10^t - 0.118 \times CCL21^t + 0.058 \times VLbeforeTTT^t + 0.227 \times GGT^t + 0.408 \times PAL^t$$

(function Z24PROTsupp; see Table 26 above), where:
MDK, LGALS3BP, CXCL10, CCL21 and IL8 are the measurement values, BMK, of the biomarkers, i.e. the measurement values for the levels of expression of the indicated genes (in fact, seric protein concentration),
VLbeforeTTT, GGT and ALP are the values for the virological factor and the biological factors indicated above, and
the exponent t (carried here by IL8, CXCL10, LGALS3BP, CCL21, VLbeforeTTT, GGT and ALP) indicates that the value to be applied in the decision rule is the Box-Cox transformation (Box and Cox, 1964) of the value of the biomarker under consideration, in order to normalize it using the following formula:

$$BMK^t = (BMK^\lambda - 1)/\lambda.$$

In the example of the decision rule indicated above, the parameters λ are 0.23 for IL8, 0.41 for CXCL10, 0.33 for LGALS3BP, −0.01 for CCL21, 0.20 for VLbeforeTTT, −0.01 for GGT and −0.11 for ALP (see Table 27 above).

If Z≥4.516, the diagnostic test is positive (mROC prediction=1), the subject is declared "NR",
If Z<4.516, the test is negative (mROC prediction=0), the subject is declared "R".

An example of a prediction for 20 subjects (human patients) is given in Table 43 below, which presents the measurement values (BMK) of the selected biomarkers (levels of seric expression of five selected genes in accordance with the invention, and the value for the virological factor VLbeforeTTT, and values for the biological factors GGT and ALP). These were the same 20 patients as those in Example 3a above.

values for the levels of expression of the indicated genes (in fact, seric protein concentration), the exponent t (carried here by CXCL10 and LGALS3BP) indicates that the value to be applied in the decision rule is the Box-Cox transformation (Box and Cox, 1964) of the measurement value of the level of expression of the gene under consideration, in order to normalize it using the following formula:

TABLE 43

Example of application of a classification model based on the combination of the levels of seric expression of the genes CXCL10, LGALS3BP, IL8, CCL21 and MDK (combination No. 24 of Table 12 above), further combined with other factors

| No. of test subject | MDK (ng/mL) | IL8 (pg/mL) | LGALS3BP (µg/mL) | CXCL10 (ng/mL) | CCL21 (pg/mL) | VLbeforeTTT | GGT | ALP | Z score | mROC prediction | Status, R or NR, as determined after treatment |
|---|---|---|---|---|---|---|---|---|---|---|---|
| 6 | 0.096 | 8.6 | 16.84 | 573.0 | 720.6 | 10450 | 78 | 40 | 5.571 | NR | NR |
| 45 | 0.080 | 13.8 | 2.09 | 268.3 | 581.7 | 3645 | 34 | 63 | 3.404 | R | R |
| 58 | 1.351 | 9.5 | 14.77 | 437.7 | 585.1 | 5079 | 162 | 51 | 4.954 | NR | NR |
| 59 | 0.188 | 14.9 | 5.15 | 137.9 | 346.0 | 1120 | 18 | 77 | 3.581 | R | R |
| 62 | 0.665 | 7.1 | 8.87 | 422.0 | 507.2 | 185 | 46 | 52 | 3.618 | R | R |
| 65 | 0.325 | 14.8 | 5.24 | 711.2 | 368.8 | 450 | 46 | 49 | 3.608 | R | R |
| 66 | 0.398 | 23.3 | 3.07 | 560.7 | 305.3 | 8132 | 65 | 83 | 4.220 | R | R |
| 73 | 0.217 | 13.5 | 4.15 | 330.1 | 391.5 | 7611 | 31 | 61 | 4.074 | R | R |
| 75 | 1.018 | 31.0 | 23.76 | 1036.3 | 372.8 | 2347 | 135 | 149 | 5.952 | NR | NR |
| 80 | 0.137 | 10.3 | 11.73 | 1068.4 | 283.7 | 12932 | 132 | 100 | 5.811 | NR | NR |
| 83 | 0.184 | 17.4 | 13.11 | 1036.3 | 384.1 | 3928 | 82 | 97 | 5.410 | NR | NR |
| 86 | 1.110 | 8.4 | 8.99 | 174.8 | 373.2 | 57 | 287 | 77 | 3.759 | R | R |
| 90 | 0.399 | 1.9 | 6.6 | 393.1 | 285.0 | 515 | 21 | 52 | 3.414 | R | R |
| 91 | 0.956 | 20.6 | 3.04 | 399.2 | 443.0 | 3902 | 39 | 72 | 3.529 | R | R |
| 92 | 0.145 | 7.5 | 1.88 | 168.9 | 387.3 | 3.2 | 92 | 68 | 2.371 | R | R |
| 145 | 0.313 | 9.8 | 11.61 | 203.4 | 578.8 | 18304 | 133 | 48 | 5.396 | NR | NR |
| 167 | 0.245 | 13.7 | 10.73 | 708.4 | 498.2 | 12616 | 378 | 114 | 5.833 | NR | NR |
| 308 | 0.489 | 14.2 | 10.63 | 304.7 | 306.4 | 423 | 246 | 73 | 4.542 | NR | NR |
| 509 | 0.145 | 41.8 | 15.45 | 911.4 | 665.8 | 8779 | 43 | 56 | 5.615 | NR | NR |
| 512 | 0.392 | 25.1 | 6.82 | 911.4 | 548.1 | 12460 | 323 | 62 | 5.268 | NR | NR |

Example 4

Seric Proteins (Combination of Levels of Expression of 3 Genes)

The AUC relating to the combination of the levels of expression of the genes MDK, LGALS3BP and CXCL10 (combination No. 9 in the Table 7 above) calculated for the complete study population of Example 3 (n=167 patients) is 0.836 (see Table 11 above). Measurements of the protein concentrations were carried out as described in Example 1 and Table 44 above. Using the mROC method, the maximizing threshold of the Youden's index (δ) for this combination is 2.164 (see Table 9 above). For this choice of threshold, the performances of the combination are as follows:

Sensitivity (Se)=82%; specificity (Spe)=74% (see Table 8 above).

The following rule is an example of a decision rule:

$$Z = 0.029 \times CXCL10^t + 0.472 \times LGALS3BP^t - 0.319 \times MDK$$

(function Z9PROT; see Table 9 above), where:
CXCL10, LGALS3BP and MDK are the measurement values for the biomarkers BMK, i.e. the measurement $$BMK^t = (BMK^\lambda - 1)/\lambda.$$

In the example of the decision rule indicated above, the parameters λ are 0.41 for CXCL10 and 0.33 for LGALS3BP.

If Z≥2.164: the diagnostic test is positive (mROC prediction=1), the subject is declared "NR" (subject predicted to be a non-responder to treatment), If Z<2.164: the test is negative (mROC prediction=0), the subject is declared "R" (subject predicted to be a responder to treatment).

An example of a prediction for 20 subjects (human patients) is given in Table 46 below, which presents the measurement values (BMK) of the levels of seric expression of the selected genes. These were the same 20 patients as those in Example 2 above.

One or more clinical factors and/or one or more biological factors and/or one or more virological factors may be combined with the levels of seric expression of the selected proteins in accordance with the invention, and lead to a decision rule the predictive power of which may be even better than that for the above rule (see Example 1 above).

TABLE 46

Example of application of a classification model based on the combination of the levels of seric expression of the genes CXCL10, LGALS3BP and MDK (combination No. 9 in Table 7 above)

| No. of test subject | mROC model $\delta = 2.164$ | | | | | Status, R or NR, as determined after treatment |
|---|---|---|---|---|---|---|
| | CXCL10 (ng/mL) | LGALS3BP (µg/mL) | MDK (ng/mL) | Z | mROC prediction | |
| 59 | 137.9 | 5.2 | 0.188 | 1.428 | R | R |
| 65 | 711.2 | 5.2 | 0.325 | 1.911 | R | R |
| 75 | 1036.3 | 23.8 | 1.018 | 3.462 | NR | NR |
| 83 | 1036.3 | 13.1 | 0.184 | 3.003 | NR | NR |
| 90 | 393.1 | 6.6 | 0.399 | 1.857 | R | R |
| 91 | 399.2 | 3.0 | 0.956 | 1.082 | R | R |
| 92 | 168.9 | 1.9 | 0.145 | 0.795 | R | R |
| 125 | 123.9 | 4.5 | 0.596 | 1.164 | R | R |
| 167 | 708.4 | 10.7 | 0.245 | 2.594 | NR | NR |
| 308 | 304.7 | 10.6 | 0.489 | 2.201 | NR | NR |
| 346 | 156.0 | 5.7 | 0.104 | 1.573 | R | R |
| 366 | 261.4 | 2.2 | 0.626 | 0.849 | R | R |
| 501 | 535.8 | 6.2 | 0.021 | 2.034 | R | R |
| 503 | 374.2 | 6.1 | 0.072 | 1.874 | R | R |
| 509 | 911.4 | 15.5 | 0.145 | 3.139 | NR | NR |
| 521 | 659.6 | 18.1 | 0.610 | 3.035 | NR | NR |
| 526 | 665.5 | 10.3 | 0.451 | 2.461 | NR | NR |
| 527 | 315.9 | 17.7 | 0.295 | 2.844 | NR | NR |
| 573 | 580.9 | 14.7 | 0.068 | 2.912 | NR | NR |
| 574 | 998.3 | 34.9 | 0.196 | 4.257 | NR | NR |

Example 5

Seric Proteins (Combination of Levels of Expression of 2 Genes)

The AUC relative to the combination of the levels of expression of the genes LGALS3BP and CXCL10 (combination No. 15 in the Table 2 above), computed for the complete study population of Example 3 (n=167 patients), is 0.831 (see Table 6 above).

Measurements of the protein concentrations were carried out as described in Example 1 and Table 44 above.

Using the mROC method, the maximizing threshold of the Youden's index ($\delta$) for this combination is 2.169 (see Table 4 above).

For this choice of threshold, the performances of the combination are as follows:
Sensitivity (Se)=82%; specificity (Spe)=72% (see Table 3 above).

The following rule is an example of a decision rule:

$$Z = 0.030 \times CXCL10^t + 0.447 \times LGALS3BP^t$$

(function Z15PROT, see Table 4 above), where:
CXCL10 and LGALS3BP are the measurement values for the biomarkers BMK, i.e. the measurement values for the levels of expression of the indicated genes (in fact, seric protein concentration),
the exponent t (carried here by CXCL10 and LGALS3BP) indicates that the value to be applied in the decision rule is the Box-Cox transformation (Box and Cox, 1964) of the measurement value of the level of expression of the gene under consideration, in order to normalize it using the following formula:

$$BMK^t = (BMK^\lambda - 1)/\lambda.$$

In the example of the decision rule indicated above, the parameters $\lambda$ are 0.41 for CXCL10 and 0.33 for LGALS3BP (see Table 5 above).

If $Z \geq 2.169$: the diagnostic test is positive (mROC prediction=1), the subject is declared "NR" (subject predicted to be a non-responder to treatment), If $Z < 2.169$: the test is negative (mROC prediction=0), the subject is declared "R" (subject predicted to be a responder to treatment).

An example of a prediction for 20 subjects (human patients) is given in Table 47 below, which presents the measurement values (BMK) for the levels of seric expression of the selected genes. These were the same 20 patients as those of Example 2 above.

One or more clinical factors and/or one or more biological factors and/or one or more virological factors may be combined with the levels of seric expression of the selected proteins in accordance with the invention, and lead to a decision rule the predictive power of which may be even better than that for the above rule.

TABLE 47

Example of application of a classification model based on the combination of the levels of seric expression of the genes CXCL10 and LGALS3BP (combination No. 15 in Table 2 above)

| No. of test subject | mROC model $\delta = 2.169$ | | | | Status, R or NR, as determined after treatment |
|---|---|---|---|---|---|
| | CXCL10 (ng/mL) | LGALS3BP (µg/mL) | Z | mROC prediction | |
| 59 | 137.9 | 5.2 | 1.450 | R | R |
| 65 | 711.2 | 5.2 | 1.993 | R | R |
| 75 | 1036.3 | 23.8 | 3.687 | NR | NR |
| 83 | 1036.3 | 13.1 | 3.000 | NR | NR |
| 90 | 393.1 | 6.6 | 1.944 | R | R |
| 91 | 399.2 | 3.0 | 1.379 | R | R |
| 92 | 168.9 | 1.9 | 0.841 | R | R |
| 125 | 123.9 | 4.5 | 1.321 | R | R |
| 167 | 708.4 | 10.7 | 2.615 | NR | NR |
| 308 | 304.7 | 10.6 | 2.291 | NR | NR |
| 346 | 156.0 | 5.7 | 1.564 | R | R |
| 366 | 261.4 | 2.2 | 1.048 | R | R |

TABLE 47-continued

Example of application of a classification model based on the combination
of the levels of seric expression of the genes CXCL10 and LGALS3BP
(combination No. 15 in Table 2 above)

| No. of test subject | CXCL10 (ng/mL) | LGALS3BP (µg/mL) | mROC model δ = 2.169 Z | mROC prediction | Status, R or NR, as determined after treatment |
|---|---|---|---|---|---|
| 501 | 535.8 | 6.2 | 2.008 | R | R |
| 503 | 374.2 | 6.1 | 1.861 | R | R |
| 509 | 911.4 | 15.5 | 3.111 | NR | NR |
| 521 | 659.6 | 18.1 | 3.141 | NR | NR |
| 526 | 665.5 | 10.3 | 2.550 | NR | NR |
| 527 | 315.9 | 17.7 | 2.841 | NR | NR |
| 573 | 580.9 | 14.7 | 2.856 | NR | NR |
| 574 | 998.3 | 34.9 | 4.190 | NR | NR |

Example 6

Combination of Levels of Expression in the Serum of Two Genes (LGALS3BP and CXCL10) (Combination No. 15 in the Table 2 Above), Further Combined with Clinical Factors and/or Biological Factors and/or Virological Factors One or more clinical factors and/or one or more biological factors and/or one or more virological factors may be combined with the levels of seric expression of the selected proteins of the invention, and lead to a decision rule the predictive power of which may be even better than that for the above rule (see Example 5).

6a) Combination of Levels of Expression in the Serum of the Genes LGALS3BP and CXCL10 (Combination No. 15 in the Table 2 Above), Combined with the "Age at the Date of Sampling", "Viral Load Before Treatment" and "Concentration of Alanine Aminotransferase" Factors.

As an example, the combination:
of the levels of seric translation of the genes LGALS3BP and CXCL10 (Table 47 above; see Example 5 above), and
of the value of the following clinical factor:
age at the date of sampling, in fact age at the date of serum sampling (Age), and
of the value for the following virological factor:
viral load before treatment (VLbeforeTTT), and
of the value for the following biological factor:
concentration of alanine aminotransferase (ALT; protein concentration in the serum),
leads to a decision rule the area under the ROC curve (AUC) of which, computed for the complete study population of Example 3 (n=167 patients), is 0.877 (see Table 28 above), while it is 0.831 (see Example 5 above) when the combination of the levels of expression of the genes LGALS3BP and CXCL10 is used alone, without being combined with the other clinical factors and/or biological factors and/or virological factors indicated above.

Using the mROC method (see Example 1), the maximizing threshold of the Youden's index for this combination is −2.345 (see Table 26 above).

For this choice of threshold, the performances of the combination are as follows:
Sensitivity (Se)=82%, specificity (Spe)=77% (see Table 25 above).

The following rule is an example of a decision rule:

$$Z=0.569 \times LGALS3BP^t + 0.033 \times CXCL10^t + 0.059 \times VLbeforeTTT^t - 0.899 \times Age^t - 0.538 \times ALT^t$$

(function Z15PROTsupp1; see Table 26 above) where:
LGALS3BP and CXCL10 are the measurement values, BMK, of the biomarkers, i.e. the measurement values for the levels of expression of the indicated genes (in fact, seric protein concentration),
VLbeforeTTT, Age and ALT are the values for the factor "viral load before treatment", for the factor "age at the date of sampling" and for the factor "concentration of alanine aminotransferase" indicated above and where
the exponent t (carried here by LGALS3BP, CXCL10, VLbeforeTTT, Age and ALT) indicate the value to be applied in the decision rule is the Box-Cox transformation (Box and Cox, 1964) of the measurement value of the biomarker BMK under consideration, in order to normalize it using the following formula:

$$BMK^t = (BMK^\lambda - 1)/\lambda.$$

In the example of the decision rule indicated above, the parameters $\lambda$, are 0.41 for CXCL10, 0.33 for LGALS3BP, 0.09 for Age, 0.2 for VLbeforeTTT and −0.09 for ALT (see Table 27 above).

If $Z \geq -2.345$: the diagnostic test is positive (mROC prediction=1), the subject is declared "NR" (subject predicted to be a non-responder to treatment), If $Z < -2.345$: the test is negative (mROC prediction=0), the subject is declared "R" (subject predicted to be a responder to treatment).

An example of a prediction for 20 subjects (human patients) is given in Table 48 below, which presents measurement values (BMK) for the levels of seric expression of the selected genes.

6b) Combinations of the Levels of Expression in the Serum of the Genes LGALS3BP, CXCL10 (Combination No. 15 in the Table 2 Above), Combined with the Factors "Age at the Date of Sampling", "Viral Load Before Treatment" and "Concentration of Gamma-Glutamyl-Transpeptidase".

As an example, the combination:
of the levels of seric translation of the genes LGALS3BP and CXCL10 (Table 47 above; see Example 5 above) and
of the value of the following clinical factor:
age at the date of sampling, in fact age at the date of serum sampling (Age), and
of the value for the following virological factor:
viral load before treatment(VLbeforeTTT), and
of the value for the following biological factor:
concentration of gamma glutamyl transpeptidase (GGT; protein concentration in the serum),
leads to a decision rule the area under the ROC curve (AUC) of which, computed for the complete study population of Example 3 (n=167 patients) is 0.872 (see Table 28 above), while it is 0.831 (see Example 5 above) when the combination of the levels of expression of the genes LGALS3BP and CXCL10 is used alone, without being combined with the other clinical factors and/or biological factors and/or virological factors indicated above.

Using the mROC method (see Example 1), the maximizing threshold of the Youden's index for this combination is 0.696 (see Table 26 above).

For this choice of threshold, the performances of the combination are as follows:
Sensitivity (Se)=83%, specificity (Spe)=74% (see Table 25 above).

The following rule is an example of a decision rule:

$$Z=0.492 \times LGALS3BP^t+0.018 \times CXCL10^t-0.701 \times Age^t+0.058 \times VLbeforeTTT^t+0.202 \times GGT^t$$

(function Z15PROTsupp2; see Table 26 above) where:
LGALS3BP and CXCL10 are the measurement values, BMK, of the biomarkers, i.e. the measurement values for the levels of expression of the indicated genes (in fact, seric protein concentration),
VLbeforeTTT, Age and GGT are the values for the factor "viral load before treatment", for the factor "age at the date of sampling" and for the factor "concentration of gamma glutamyl transpeptidase" indicated, above and where
the exponent t (carried here by LGALS3BP, CXCL10, VLbeforeTTT, Age, GGT) indicates that the value to be applied in the decision rule is the Box-Cox transformation (Box and Cox, 1964) of the measurement value of the biomarker BMK under consideration, in order to normalize it using the following formula:

$$BMK^t=(BMK^\lambda-1)/\lambda.$$

In the example of the decision rule indicated above, the parameters $\lambda$, are 0.41 for CXCL10, 0.33 for LGALS3BP, 0.09 for Age, 0.2 for VLbeforeTTT and −0.01 for GGT (see Table 27 above).
If Z≥0.696: the diagnostic test is positive (mROC prediction=1), the subject is declared "NR" (subject predicted to be a non-responder to treatment),
If Z<0.696: the test is negative (mROC prediction=0), the subject is declared "R" (subject predicted to be a responder to treatment).
An example of a prediction for 20 subjects (human patients) is given in Table 49 below, which presents measurement values (BMK) for the levels of seric expression of the selected genes.
6c) Combinations of the Levels of Expression in the Serum of the Genes LGALS3BP, CXCL10 (Combination No. 15 in the Table 2 Above), Combined with the Factors "Viral Load Before Treatment", "Concentration of Aspartate Aminotransferase" and "Concentration of Alkaline Phosphatase"
As an example, the combination:
of the levels of seric translation of the genes LGALS3BP and CXCL10 (Table 47 above; see Example 5 above), and
of the value for the virological factor:
viral load before treatment (VLbeforeTTT), and
of the values for the following (other) biological factors:
"concentration of aspartate aminotransferase" (AST; protein concentration in the serum),
"concentration of alkaline phosphatase" (ALP, protein concentration in the serum)
leads to a decision rule the area under the ROC curve (AUC) of which, computed for the complete study population of Example 3 (n=167 patients), is 0.869 (see Table 28 above), while it is 0.831 (see Example 5 above) when the combination of the levels of expression of the genes LGALS3BP and CXCL10 was used alone, without being combined with the other biological factors and/or virological factors indicated above.
Using the mROC method (see Example 1), the maximizing threshold of the Youden's index for this combination is 3.862 (see Table 26 above).
For this choice of threshold, the performances of the combination are as follows:
Sensitivity (Se)=86%, specificity (Spe)=77% (see Table 25 above).

The following rule is an example of a decision rule:

$$Z=0.499 \times LGALS3BP^t+0.028 \times CXCL10^t+0.06 \times VLbeforeTTT^t-1.147 \times AST^t+0.931 \times PAL^t,$$

(function Z15PROTsupp3; see Table 26 above) where:
LGALS3BP and CXCL10 are the measurement values, BMK, of the biomarkers, i.e. the measurement values for the levels of expression of the indicated genes (in fact, seric protein concentration)
VLbeforeTTT, AST and ALP are the values for the factor "viral load before treatment", for the factor "concentration of aspartate aminotransferase" and for the factor "concentration alkaline phosphatase" indicated above, and where
the exponent t (carried here by LGALS3BP and CXCL10) indicates that the value to be applied in the decision rule is the Box-Cox transformation (Box and Cox, 1964) of the measurement value of the biomarker BMK under consideration, in order to normalize it using the following formula:

$$BMK^t=(BMK^\lambda-1)/\lambda.$$

In the example of the decision rule indicated above, the parameters $\lambda$, are 0.41 for CXCL10, 0.33 for LGALS3BP, 0.2 for VLbeforeTTT, −0.3 for AST and −0.11 for ALP (see Table 27 above).
If Z≥3.862: the diagnostic test is positive (mROC prediction=1), the subject is declared "NR" (subject predicted to be a non-responder to treatment),
If Z<3.862: the test is negative (mROC prediction=0), the subject is declared "R" (subject predicted to be a responder to treatment).
An example of a prediction for 20 subjects (human patients) is given in Table 50 below, which presents measurement values (BMK) for the levels of seric expression of the selected genes.
6d) Combinations of the Levels of Expression in Serum of the Genes LGALS3BP, CXCL10 (Combination No. 15 in the Table 2 Above), Combined with the Clinical Factor "Body Mass Index".
As an example, the combination:
of the levels of seric translation of the genes LGALS3BP, CXCL10 (Table 47 above; see Example 5 above), and
of the value for the clinical factor
body mass index (BMI),
leads to a decision rule the area under the ROC curve (AUC) of which, computed for the complete study population of Example 3 (n=167 patients), is 0.834 (see Table 28 above), while it was 0.831 (see Example 5 above) when the combination of the levels of expression of the genes LGALS3BP and CXCL10 is used alone, without being combined with the clinical factor indicated above.
Using the mROC method (see Example 1), the maximizing threshold of the Youden's index for this combination is 0.375 (see Table 26 above).
For this choice of threshold, the performances of the combination are as follows:
Sensitivity (Se)=81%, specificity (Spe)=78% (see Table 25 above).
The following rule is an example of a decision rule:

$$Z=0.451 \times LGALS3BP^t+0.033 \times CXCL10^t-0.535 \times IMC^t,$$

(function Z15PROTsupp4; see Table 26 above) where:
LGALS3BP and CXCL10 are the measurement values, BMK, of the biomarkers, i.e. the measurement values for the levels of expression of the indicated genes (in fact, seric protein concentration).

BMI is the value for the factor body mass index, and where the exponent t (carried here by LGALS3BP and CXCL10) indicates that the value to be applied in the decision rule is the Box-Cox transformation (Box and Cox, 1964) of the measurement value of the biomarker BMK under consideration, in order to normalize it using the following formula:

$$BMK^t = (BMK^\lambda - 1)/\lambda.$$

In the example of the decision rule indicated above, the parameters $\lambda$, are 0.41 for CXCL10, 0.33 for LGALS3BP, 0.08 for BMI (see Table 27 above).

If $Z \geq 0.375$: the diagnostic test is positive (mROC prediction=1), the subject is declared "NR" (subject predicted to be a non-responder to treatment), If $Z < 0.375$: the test is negative (mROC prediction=0), the subject is declared "R" (subject predicted to be a responder to treatment).

An example of a prediction for 20 subjects (human patients) is given in Table 51 below, which presents measurement values (BMK) for the levels of seric expression of the selected genes.

TABLE 48

Example of application of a classification model based on the combination of the levels of seric expression of the genes CXCL10 and LGALS3BP and for the clinical factor "age at the date of sampling" (Age), for the virological factor "viral load before treatment" (VLbeforeTTT)) and for the biological factor "concentration of alanine aminotransferase" (ALT), (Example 6a).

| | | | | mROC model $\delta = -2.345$ | | | | Status, R or NR, as determined |
|---|---|---|---|---|---|---|---|---|
| No. of test subject | CXCL10 (ng/mL) | LGALS3BP (µg/mL) | Age | VLbeforeTTT (copies/mL · 10³) | ALT (U/L) | Z | mROC prediction | after treatment |
| 6 | 573.0 | 16.8 | 59 | 10450 | 69 | −1.078 | NR | NR |
| 45 | 268.3 | 2.1 | 44 | 3645 | 458 | −4.177 | R | R |
| 58 | 437.7 | 14.8 | 48 | 5079 | 93 | −1.475 | NR | NR |
| 59 | 137.9 | 5.1 | 51 | 1120 | 80 | −3.516 | R | R |
| 62 | 422.0 | 8.9 | 62 | 185 | 47 | −2.993 | R | R |
| 65 | 711.2 | 5.2 | 35 | 450 | 152 | −2.885 | R | R |
| 66 | 560.7 | 3.1 | 43 | 8132 | 71 | −2.655 | R | R |
| 73 | 330.1 | 4.1 | 55 | 7611 | 101 | −3.087 | R | R |
| 75 | 1036.3 | 23.8 | 53 | 2347 | 50 | −0.483 | NR | NR |
| 80 | 1068.4 | 11.7 | 37 | 12932 | 67 | −0.555 | NR | NR |
| 83 | 1036.3 | 13.1 | 51 | 3928 | 95 | −1.398 | NR | NR |
| 86 | 174.8 | 9.0 | 50 | 57 | 105 | −3.467 | R | R |
| 90 | 393.1 | 6.6 | 59 | 515 | 119 | −3.437 | R | R |
| 91 | 399.2 | 3.0 | 48 | 3902 | 79 | −3.232 | R | R |
| 92 | 168.9 | 1.9 | 35 | 3 | 128 | −4.828 | R | R |
| 167 | 708.4 | 10.7 | 49 | 12616 | 144 | −1.523 | NR | NR |
| 509 | 911.4 | 15.4 | 48 | 8779 | 243 | −1.216 | NR | NR |
| 517 | 911.4 | 15.8 | 48 | 11114 | 147 | −0.906 | NR | NR |
| 521 | 659.6 | 18.1 | 58 | 14432 | 166 | −1.081 | NR | NR |
| 527 | 315.9 | 17.7 | 47 | 3457 | 80 | −1.390 | NR | NR |

TABLE 49

Example of application of a classification model based on the combination of the levels of seric expression of the genes CXCL10 and LGALS3BP and for the clinical factor "age at the date of sampling" (Age), for the virological factor "viral load before treatment" (VLbeforeTTT) and for the biological factor "concentration of gamma-glutamyl-transpeptidase" (GGT), (Example 6b).

| | | | | mROC model $\delta = 0.696$ | | | | Status, R or NR, as determined |
|---|---|---|---|---|---|---|---|---|
| No. of test subject | CXCL10 (ng/mL) | LGALS3BP (µg/mL) | Age | VLbeforeTTT (copies/mL · 10³) | GGT (U/L) | Z | mROC prediction | after treatment |
| 6 | 573.0 | 16.8 | 59 | 10450 | 78 | 1.808 | NR | NR |
| 45 | 268.3 | 2.1 | 44 | 3645 | 34 | −0.459 | R | R |
| 58 | 437.7 | 14.8 | 48 | 5079 | 162 | 1.684 | NR | NR |
| 59 | 137.9 | 5.1 | 51 | 1120 | 18 | −0.481 | R | R |
| 62 | 422.0 | 8.9 | 62 | 185 | 46 | −0.151 | R | R |
| 65 | 711.2 | 5.2 | 35 | 450 | 46 | 0.195 | R | R |
| 66 | 560.7 | 3.1 | 43 | 8132 | 65 | 0.376 | R | R |
| 73 | 330.1 | 4.1 | 55 | 7611 | 31 | 0.060 | R | R |
| 75 | 1036.3 | 23.8 | 53 | 2347 | 135 | 2.161 | NR | NR |
| 80 | 1068.4 | 11.7 | 37 | 12932 | 132 | 2.210 | NR | NR |

TABLE 49-continued

Example of application of a classification model based on the combination of the levels of seric expression of the genes CXCL10 and LGALS3BP and for the clinical factor "age at the date of sampling" (Age), for the virological factor "viral load before treatment" (VLbeforeTTT) and for the biological factor "concentration of gamma-glutamyl-transpeptidase" (GGT), (Example 6b).

| | | | | | | mROC model $\delta = 0.696$ | | | Status, R or NR, as determined |
|---|---|---|---|---|---|---|---|---|---|
| No. of test subject | CXCL10 (ng/mL) | LGALS3BP (µg/mL) | Age | VLbeforeTTT (copies/mL · $10^3$) | GGT (U/L) | Z | mROC prediction | after treatment | |
| 83 | 1036.3 | 13.1 | 51 | 3928 | 82 | 1.492 | NR | NR |
| 86 | 174.8 | 9.0 | 50 | 57 | 287 | 0.096 | R | R |
| 90 | 393.1 | 6.6 | 59 | 515 | 21 | −0.369 | R | R |
| 91 | 399.2 | 3.0 | 48 | 3902 | 39 | −0.161 | R | R |
| 92 | 168.9 | 1.9 | 35 | 3 | 92 | −1.308 | R | R |
| 167 | 708.4 | 10.7 | 49 | 12616 | 378 | 1.909 | NR | NR |
| 509 | 911.4 | 15.4 | 48 | 8779 | 43 | 1.850 | NR | NR |
| 517 | 911.4 | 15.8 | 48 | 11114 | 266 | 2.332 | NR | NR |
| 521 | 659.6 | 18.1 | 58 | 14432 | 127 | 2.161 | NR | NR |
| 527 | 315.9 | 17.7 | 47 | 3457 | 127 | 1.687 | NR | NR |

TABLE 50

Example of application of a classification model based on the combination of the levels of seric expression of the genes CXCL10 and LGALS3BP, for the virological factor "viral load before treatment" (VLbeforeTTT) and for the biological factors "concentration of aspartate aminotransferase" (AST) and "concentration of alkaline phosphatase" (ALP), (Example 6c).

| | | | | | | mROC model $\delta = 3.862$ | | | Status, R or NR, as determined |
|---|---|---|---|---|---|---|---|---|---|
| No. of test subject | CXCL10 (ng/mL) | LGALS3BP (µg/mL) | VLbeforeTTT (copies/mL · $10^3$) | AST (U/L) | ALP (U/L) | Z | mROC prediction | after treatment | |
| 6 | 573.0 | 16.8 | 10450 | 50 | 40 | 4.973 | NR | NR |
| 45 | 268.3 | 2.1 | 3645 | 152 | 63 | 2.393 | R | R |
| 58 | 437.7 | 14.8 | 5079 | 62 | 51 | 4.533 | NR | NR |
| 59 | 137.9 | 5.1 | 1120 | 49 | 77 | 3.034 | R | R |
| 62 | 422.0 | 8.9 | 185 | 34 | 52 | 3.381 | R | R |
| 65 | 711.2 | 5.2 | 450 | 61 | 49 | 2.997 | R | R |
| 66 | 560.7 | 3.1 | 8132 | 39 | 83 | 3.750 | R | R |
| 73 | 330.1 | 4.1 | 7611 | 78 | 61 | 3.356 | R | R |
| 75 | 1036.3 | 23.8 | 2347 | 64 | 149 | 5.872 | NR | NR |
| 80 | 1068.4 | 11.7 | 12932 | 44 | 100 | 5.481 | NR | NR |
| 83 | 1036.3 | 13.1 | 3928 | 78 | 97 | 4.960 | NR | NR |
| 86 | 174.8 | 9.0 | 57 | 53 | 77 | 3.035 | R | R |
| 90 | 393.1 | 6.6 | 515 | 61 | 52 | 3.049 | R | R |
| 91 | 399.2 | 3.0 | 3902 | 64 | 72 | 3.116 | R | R |
| 92 | 168.9 | 1.9 | 3 | 29 | 68 | 1.633 | R | R |
| 167 | 708.4 | 10.7 | 12616 | 163 | 114 | 4.861 | NR | NR |
| 509 | 911.4 | 15.4 | 8779 | 154 | 56 | 4.860 | NR | NR |
| 517 | 911.4 | 15.8 | 11114 | 103 | 65 | 5.177 | NR | NR |
| 521 | 659.6 | 18.1 | 14432 | 83 | 62 | 5.345 | NR | NR |
| 527 | 315.9 | 17.7 | 3457 | 35 | 67 | 4.901 | NR | NR |

TABLE 51

Example of application of a classification model based on the combination of the levels of seric expression of the genes CXCL10 and LGALS3BP and for the clinical factor "body mass index" (BMI) (Example 6d).

| No. of test subject | mROC model $\delta = 0.375$ | | | | Status, R or NR, |
|---|---|---|---|---|---|
| | CXCL10 (ng/mL) | LGALS3BP (µg/mL) | BMI | Z | mROC prediction | as determined after treatment |
| 6 | 573.0 | 16.8 | 19.6 | 1.314 | NR | NR |
| 45 | 268.3 | 2.1 | 22.0 | −0.784 | R | R |
| 58 | 437.7 | 14.8 | 25.2 | 0.879 | NR | NR |
| 59 | 137.9 | 5.1 | 23.7 | −0.421 | R | R |
| 62 | 422.0 | 8.9 | 27.4 | 0.293 | R | R |
| 65 | 711.2 | 5.2 | 29.6 | 0.022 | R | R |
| 66 | 560.7 | 3.1 | 19.4 | −0.179 | R | R |
| 73 | 330.1 | 4.1 | 23.4 | −0.312 | R | R |
| 75 | 1036.3 | 23.8 | 27.9 | 1.789 | NR | NR |
| 80 | 1068.4 | 11.7 | 31.6 | 0.908 | NR | NR |
| 83 | 1036.3 | 13.1 | 25.7 | 1.152 | NR | NR |
| 86 | 174.8 | 9.0 | 28.4 | −0.010 | R | R |
| 90 | 393.1 | 6.6 | 25.2 | 0.064 | R | R |
| 91 | 399.2 | 3.0 | 21.4 | −0.393 | R | R |
| 92 | 168.9 | 1.9 | 28.7 | −1.163 | R | R |
| 167 | 708.4 | 10.7 | 37.8 | 0.475 | NR | NR |
| 509 | 911.4 | 15.4 | 20.8 | 1.405 | NR | NR |
| 517 | 911.4 | 15.8 | 23.3 | 1.356 | NR | NR |
| 521 | 659.6 | 18.1 | 23.8 | 1.328 | NR | NR |
| 527 | 315.9 | 17.7 | 37.3 | 0.685 | NR | NR |

REFERENCES

Anastasiadis et al. 2005; New globally convergent training scheme based on the resilient propagation algorithm. Neurocomputing 64: 253-270.

Asselah et al. 2008; "Liver gene expression signature to predict response to pegylated interferon plus ribavirin combination therapy in patients with chronic hepatitis C"; Gut 57: 516-524.

Box and Cox 1964; An analysis of transformations. Journal of the Royal Statistical Society, Series B 26: 211-243.

Breiman 2001; Random Forests. Machine Learning 45: 5-32.

Chambers 2008; Software for data analysis: programming with R. Springer, New York, ISBN 978-0-387-75935-7.

Chen et al. 2005; Gastroenterology 128: 1437-1444.

Chen et al. 2010; Gastroenterology 138: 1123-1133.

Cole et al. 1983; Proc. Natl. Acad. Sci. USA 80: 2026-2030.

Cole et al. 1985; Monoclonal Antibodies And Cancer Therapy, Alan R. Liss, Inc., pp. 77-96.

Falissard 2005; Comprendre et utiliser les statistiques dans les sciences de la vie [Understanding and using statistics in the life sciences], Masson.

Hastie, Tibishirani and Friedman, 2009; "The Elements of Statistical Learning: Data Mining, Inference and Prediction", $2^{nd}$ Edition, Springer.

Hidetsugu Saito et al. 2010; "On-treatment predictions of success in peg-interferon/ribavirin treatment using a novel formula"; World J. Gastroenterol. 16(1): 89-97.

Intrator and Intrator 1993; Using Neural Nets for Interpretation of Nonlinear Models. Proceedings of the Statistical Computing Section, San Francisco: American Statistical Society (eds), pages 244-249.

Köhler and Milstein 1975; Nature 256: 495-497.

Kosbor et al. 1983; Immunology Today 4: 72.

Kramar et al. 1999; Critères ROC généralisés pour l'évaluation de plusieurs marqueurs tumoraux [Generalized ROC criteria for the evaluation of a number of tumour markers]. Revue d'Epidemiologie and Santé Publique 47:376-383.

Kramar et al. 2001; mROC: a computer program for combining tumour markers in predicting disease states. Computer methods and programs in biomedicine 66: 199-207.

Liaw and Wiener 2002; Classification and regression by Random Forest. R. News 2.3: 18-22.

Livak and Schmittgen 2001; Analysis of relative gene expression data using real-time quantitative PCR and the 2(-Delta C(T)) Method. Methods 25: 402-408.

Reiser and Faraggi 1997; Confidence intervals for the generalized ROC criterion. Biometrics 53: 644-652.

Riedmiller 1994; Rprop—Description and Implementation Details. Technical Report. University of Karlsruhe.

Riedmiller and Braun 1993; A direct adaptive method for faster backpropagation learning: the RPROP algorithm. Proceedings of the IEEE International Conference on Neural Networks (ICNN), San Francisco, pages 586-591.

Schmitten and Livak 2008; Analyzing real-time PCR data by the comparative Ct method. Nature Protocols 3(6): 1101-1108.

Shapiro 1999; The interpretation of diagnostic tests. Statistical Methods in Medical Research, 8: 113-134.

Su and Liu 1993; Linear combinations of multiple diagnostic markers. Journal of the American Statistical Association 88: 1350-1355.

Swets 1988; Measuring the accuracy of diagnostic systems. Science 240, 1285-1293.

Theodoridis and Koutroumbos 2009; Pattern Recognition. Academic Press, Elsevier.

U.S. Pat. No. 4,376,110 (in the name of Hybritech Inc.).

Wahba, 1990; "Splines Models for Observational Data"; SIAM—Society for Industrial and Applied Mathematics.

Wahba and Wold, 1975; "A completely automatic French curve: Fitting spline functions by cross-validation"; Communications in Statistics, 4:1-17, 1975.

The invention claimed is:

1. An in vitro method for predicting, prior to treatment, whether a subject infected with one or more HCVs has a high probability of being a responder or a non-responder to an anti-HCV treatment comprising interferon and ribavirin or a prodrug thereof, said method comprising the following steps:

i) in a sample which has already been obtained from said subject, measuring the levels to which a group of 2, 3, 4, or 5 selected genes have been transcribed or translated, wherein said selected genes consist of:

at least one gene selected from the group consisting of MBL2, LGALS3BP and IL8, and at least one gene selected from the group consisting of G1P2, CCL21 and CXCL10, and none or at least one gene selected from the group consisting of AFP, CRP, CXCL11, CXCL6, CXCL9, FGF7, MDK, MMP2, SFN, TGFB2 and VEGFD, measuring or determining, for said subject, the value of one or more clinical factors comprising a hepatic fibrosis score measured by the Metavir system (Metavir F score) or the Ishak system and of zero, virological factors consisting of viral genotype, and viral load before treatment and/or of zero, one or more biological factors other than the levels of expression of genes selected from MBL2, LGALS3BP, IL8, G1P2, CXCL10, CCL21, AFP, CRP, CXCL11, CXCL6, CXCL9, FGF7, MDK, MMP2, SFN, TGFB2 and VEGFD, ii) comparing the values for the measurements obtained for said subject in step i) with their values, or the distribution of their values, in reference cohorts which have been pre-established as a function of their status of responder or non-responder to anti-HCV treatment, in order to classify said subject into that of those reference cohorts to which it has the highest probability of belonging, said method being further characterized in that the total number of mammalian genes the level of expression of which is measured is from 2 to 9, and wherein the classification of said subject into that of said reference cohorts to which it has the highest probability of belonging is made with a sensitivity (Se) of at least 75%; and/or with a specificity (Sp) of at least 92%.

2. The method according to claim 1, characterized in that it is carried out before said anti-HCV treatment has commenced.

3. The method according to claim 1, in which the total number of said other clinical, virological and biological factors, the value of which is measured or determined in step i), is 0 to 4.

4. The method according to claim 1, in which the comparison of step ii) is carried out by combining the measurement values obtained for said subject in step i) into a multivariate classification model which compares those values with their values, or the distribution of their values, in reference cohorts which have been pre-established as a function of their status of responder or non-responder, in order to classify said subject into that of those reference cohorts to which it has the highest probability of belonging.

5. The method according to claim 1, in which the comparison of step ii) is made by combining measurement values obtained for said subject in step i) into a pre-constructed multivariate classification model as follows:
a) for a population of individuals who are of the same species as said subject, and who are infected with one or more HCVs, determining for each of those individuals whether or not that individual responds to an anti-HCV treatment which comprises the administration of interferon and of ribavirin, and classifying those individuals into distinct sub-populations as a function of whether they are responders or whether they are non-responders to that treatment, thus constituting reference cohorts established as a function of the response or non-response of those individuals to anti-HCV treatment;
b) in at least one sample which has previously been obtained from each of said individuals, the nature of which is identical to that of the sample from said subject, making the same measurements as those carried out for said subject in said step i);
c) making an inter-cohort comparison of the values for the measurements obtained in step b), or of the distribution of those values, in order to construct a multivariate classification model which infers a status of responder to anti-HCV treatment or a status of non-responder to that treatment, starting from the combination of said values for the measurements obtained in step b).

6. The method according to claim 1, in which the comparison of step ii) is made by combining said measurement values obtained in step i) into a mathematical function in order to obtain an output value which is indicative of the status of responder or of non-responder of said subject.

7. The method according to claim 1, in which the comparison of step ii) is made by combining said values obtained in step i) into a multivariate machine learning model in order to obtain an output value which is indicative of the status of responder or of non-responder of said subject.

8. The method according to claim 1, in which the classification of said subject into that of said reference cohorts to which it has the highest probability of belonging is made with:
a sensitivity (Se) of at least 76%,
a negative predictive value (NPV) of at least 78%; and/or with
a positive predictive value (PPV) of at least 63%.

9. The method according to claim 1, in which said multivariate classification model has:
an area under the ROC curve (AUC) of at least 0.76, and/or
a LOOCV error of at most 18%.

10. The method according to claim 1 in which, in step i), said genes selected from:
at least one gene selected from the group consisting of MBL2, LGALS3BP and IL8, and
at least one gene selected from the group consisting of G1P2, CCL21 and CXCL10, and
none or, at least one gene selected from the group consisting of AFP, CRP, CXCL11, CXCL6, CXCL9, FGF7, MDK, MMP2, SFN, TGFB2 and VEGFD, are:
LGALS3BP and CXCL10 (combination No.15); or
LGALS3BP, CXCL10 and MDK (combination No.9); or
LGALS3BP, IL8, CXCL10, CCL21 and MDK (combination No.24); or
CRP, G1P2, LGALS3BP, MBL2 and TGFB2 (combination No.1); or
AFP, CXCL6, CXCL9, G1P2 and MBL2 (combination No.2); or
AFP, FGF7, G1P2, MBL2 and MMP2 (combination No.3); or
CXCL11, G1P2, IL8, MBL2 and TGFB2 (combination No.4); or
G1P2, IL8, MBL2, SFN and TGFB2 (combination No.5); or
CCL21, FGF7, IL8, LGALS3BP and MBL2 (combination No.6); or
G1P2, LGALS3BP, MBL2, MDK and TGFB2 (combination No.7); or
G1P2, LGALS3BP, MBL2, MMP2 and TGFB2 (combination No.8); or
G1P2, LGALS3BP, MBL2, SFN and TGFB2 (combination No.10); or
CXCL6, CXCL10, G1P2, MBL2 and MMP2 (combination No.11); or
CXCL6, CXCL11, G1P2, MBL2 and MMP2 (combination No.12); or
FGF7, G1P2, LGALS3BP, MBL2 and TGFB2 (combination No.13); or
AFP, CXCL6, G1P2, IL8 and MDK (combination No.14); or
CCL21, G1P2, LGALS3BP, MBL2 and SFN (combination No.16); or
CXCL10, G1P2, LGALS3BP, MBL2 and TGFB2 (combination No.17); or
CRP, CXCL6, G1P2, MBL2 and SFN (combination No.18); or
CXCL10, CXCL11, G1P2, MBL2 and MMP2 (combination No.19); or
CXCL11, G1P2, LGALS3BP, MBL2 and MDK (combination No.20); or
G1P2, IL8, LGALS3BP, MBL2 and TGFB2 (combination No.21); or
FGF7, G1P2, IL8, MDK and SFN (combination No.22); or
CCL21, FGF7, LGALS3BP, MBL2 and MDK (combination No.23); or
CCL21, CXCL6, 1L8, LGALS3BP and MDK (combination No.25); or
CCL21, FGF7, MBL2, MDK and VEGFD (combination No.26); or
CXCL6, IL8, CCL21, GIP2 and MDK (combination No.30); or
CXCL6, IL8, CXCL10, GIP2 and MDK (combination No.33); or
CCL21, CXCL10, GIP2, LGALS3BP and MDK (combination No.34); or
CXCL6, IL8, CCL21, GIP2 and LGALS3BP (combination No.35); or
IL8, CCL21, CXCL10. GIP2 and LGALS3BP (combination No.37); or
IL8, CXCL10, GIP2, LGALS3BP and MDK (combination No.38); or
CXCL6, IL8, GIP2, LGALS3BP and MDK (combination No.39); or
FGF7, G1P2, LGALS3BP, MBL2 and MDK (combination No.27); or CXCL10, FGF7, IL8, MDK and VEGFD (combination No.28); or CCL21, CXCL6, CXCL10, LGALS3BP and MDK (combination No.29); or IL8, CCL21, G1P2, LGALS3BP and MDK (combination No.31); or IL8, CCL21, CXCL10, G1P2 and MDK (combination No.32); or CXCL6, IL8, CXCL10, G1P2 and LGALS3BP (combination No.36); or CXCL6, IL8, CCL21, CXCL10 and G1P2 (combination No.40); or CXCL6, CXCL10, G1P2, LGALS3BP and MDK (combination No.41); or CXCL6, IL8, CCL21, CXCL10 and LGALS3BP (combination No.42); or CXCL6, CCL21, CXCL10, G1P2 and LGALS3BP (combination No.43).

11. The method according to claim 1 in which, in step i), the levels of translation of said selected genes are assayed.

12. The method according to claim 1, in which:
said clinical factor or factors are selected from the group consisting of: sex, age at the date of sampling, age of patient at the date of contamination, age of patient at the treatment start date, body mass index, insulin sensitivity index, diabetes, alcohol consumption, degree of steatosis, mode of contamination, and Metavir activity; and/or
said virological factor or factors are selected from the group consisting of: viral genotype, duration of infection, viral load before treatment, viral load assayed for the patient at the treatment start date, and viral load assayed for the patient at the date of sampling; and/or
said biological factor or factors other than the levels of expression of genes selected from MBL2, LGALS3BP, IL8, G1P2, CXCL10, CCL21, AFP, CRP, CXCL11, CXCL6, CXCL9, FGF7, MDK, MMP2, SFN, TGFB2 and VEGFD are selected from the group consisting of: concentration of haptoglobin, concentration of apolipoprotein Al, total quantity of bilirubin, concentration of gamma glutamyl transpeptidase, concentration of aspartate aminotransferase, concentration of alanine aminotransferase, platelet count, quantity of prothrombin, quantity of HDL cholesterol, total quantity of cholesterol, concentration of ferritin, level of glycaemia, concentration of peptide C, quantity of insulin, concentration of triglycerides, quantity of albumin, transferrin saturation, and concentration of alkaline phosphatase.

13. The method according to claim 1, in which:
said clinical factor or factors comprise the hepatic fibrosis score measured using the Metavir system (Metavir F score) or using the Ishak system, and/or age at the date of sampling (Age); and/or
said virological factor or factors comprise the viral genotype and/or the viral load before treatment; and/or
said biological factor or factors other than the levels of expression of genes selected from MBL2, LGALS3BP, IL8, G1P2, CXCL10, CCL21, AFP, CRP, CXCL11, CXCL6, CXCL9, FGF7, MDK, MMP2, SFN, TGFB2 and VEGFD comprise the concentration of gamma glutamyl transpeptidase and/or the concentration of alanine aminotransferase and/or the concentration of aspartate aminotransferase.

14. The method according to claim 1, which comprises:
determining whether the hepatic fibrosis score of said subject is a score which, in the Metavir score system, is at least F1; and/or
determining whether the HCV or HCVs with which said subject is infected comprises an HCV of genotype 1, 4, 5 or 6.

15. The method according to claim 1, in which said sample which has been obtained in advance from said subject is:
a sample of intracorporal biological fluid which has been taken from said subject, such as a sample of blood, serum or plasma, or a sample of urine from said subject, or
a sample containing proteins and/or polypeptides and/or peptides extracted or purified from said biological sample.

16. The in vitro method according to claim 1, wherein said biological factors consist of:
concentration of gamma glutamyl transpeptidase,
concentration of aspartate aminotransferase,
concentration of alanine aminotransferase, and
concentration of alkaline phosphatase.

17. The in vitro method according to claim 1, wherein said clinical factors consist of:
age at the date of sampling, and
body mass index.

18. The in vitro method according to claim 1, which does not comprise measuring or determining the value of any of said virological and biological factors.

19. The method according to claim 6, wherein the mathematical function is a linear or non-linear function.

20. The method according to claim 6, wherein the mathematical function is a linear function.

21. The method according to claim 7, wherein the multivariate machine learning model is a multivariate non-parametric classification model.

22. The method according to claim 7, wherein the multivariate machine learning model is a multivariate heuristic model.

23. The method according to claim 7, wherein the multivariate machine learning model is a multivariate probabilistic prediction model.

24. The method according to claim 1, the method further comprising administering an anti-HCV treatment comprising interferon and ribavirin.

25. A method of measuring the level of each protein in a combination of proteins in a sample obtained from a subject suffering from hepatitis C virus (HCV) infection, wherein the combination of proteins comprises 2, 3, 4, or 5 proteins, and wherein the combination of proteins consists of:
i) at least one protein selected from the group consisting of MBL2, LGALS3BP and IL8;
ii) at least one protein selected from the group consisting of G1P2, CCL21 and CXCL10; and
iii) none or at least one protein selected from the group consisting of AFP, CRP, CXCL11, CXCl6, CXCL9, FGF7, MDK, MMP2, SFN, TGFB2 and VEGFD,
wherein said measuring comprises the steps of:
i) obtaining the sample from the subject;
ii) contacting the sample with antibodies against each of the proteins in the combination of proteins measured;
iii) detecting the binding between each of the proteins and the corresponding antibody; and
iv) measuring the amount of each of the proteins in the combination of proteins.

26. The method of claim 25, the method further comprising:

determining, for said subject, the value of one or more clinical factors comprising a hepatic fibrosis score measured by the Metavir system (Metavir F score) or the Ishak system and of zero, one or more virological factors and/or of zero, one or more biological factors other than the levels of expression of genes selected from MBL2, LGALS3BP, IL8, G1P2, CXCL10, CCL21, AFP, CRP, CXCL11, CXCL6, CXCL9, FGF7, MDK, MMP2, SFN, TGFB2 and VEGFD.

* * * * *

UNITED STATES PATENT AND TRADEMARK OFFICE
CERTIFICATE OF CORRECTION

PATENT NO. : 9,879,320 B2  
APPLICATION NO. : 13/983405  
DATED : January 30, 2018  
INVENTOR(S) : Ivan Bieche et al.

Page 1 of 1

It is certified that error appears in the above-identified patent and that said Letters Patent is hereby corrected as shown below:

In the Claims

Claim 14, Line 5, "IICV" should be changed to --HCV--

Signed and Sealed this
Twenty-fourth Day of July, 2018

Andrei Iancu
*Director of the United States Patent and Trademark Office*